US011357622B2

(12) United States Patent
Lane et al.

(10) Patent No.: US 11,357,622 B2
(45) Date of Patent: *Jun. 14, 2022

(54) PROSTHETIC VALVE FOR AVOIDING OBSTRUCTION OF OUTFLOW

(71) Applicant: Neovasc Tiara Inc., Richmond (CA)

(72) Inventors: Randy Matthew Lane, Langley (CA); Karen Tsoek-Ji Wong, Richmond (CA); Ian Fraser Kerr, Vancouver (CA); Mark Segal, Vancouver (CA)

(73) Assignee: Neovase Tiara Inc., Richmond (CA)

( * ) Notice: Subject to any disclaimer, the term of this patent is extended or adjusted under 35 U.S.C. 154(b) by 279 days.

This patent is subject to a terminal disclaimer.

(21) Appl. No.: 16/559,169

(22) Filed: Sep. 3, 2019

(65) Prior Publication Data

US 2019/0388219 A1    Dec. 26, 2019

Related U.S. Application Data

(63) Continuation of application No. 15/418,511, filed on Jan. 27, 2017, now Pat. No. 10,433,952.

(60) Provisional application No. 62/288,987, filed on Jan. 29, 2016.

(51) Int. Cl.
*A61F 2/24*    (2006.01)

(52) U.S. Cl.
CPC ............ *A61F 2/2409* (2013.01); *A61F 2/243* (2013.01); *A61F 2/2412* (2013.01); *A61F 2/2418* (2013.01); *A61F 2/2436* (2013.01); *A61F 2220/0033* (2013.01);

(Continued)

(58) Field of Classification Search
CPC ........ A61F 2/24; A61F 2/2409; A61F 2/2466; A61F 2/243; A61F 2/2412; A61F 2/2418; A61F 2/2436; A61F 2/2427; A61F 2220/0033; A61F 2230/006; A61F 2230/0034; A61F 2230/0069
See application file for complete search history.

(56) References Cited

U.S. PATENT DOCUMENTS 2,967,856 A     1/1961   Coover, Jr. et al.
5,957,949 A *   9/1999   Leonhardt ............. A61F 2/2436
                                                          623/1.24

(Continued)

FOREIGN PATENT DOCUMENTS

AU    2011250606 B2    3/2014
AU    2014203064 A1    7/2014

(Continued)

OTHER PUBLICATIONS

"Chinese Application Serial No. 201780021798.X, Response filed Sep. 30, 2020 to Office Action dated Jul. 16, 20", with machine translation, 12 pgs.

(Continued)

*Primary Examiner* — Vi X Nguyen
(74) *Attorney, Agent, or Firm* — Schwegman Lundberg & Woessner, P.A.

(57) ABSTRACT

A prosthetic mitral valve may be anchored in a native mitral valve. The prosthetic mitral valve preferably has a large anterior prosthetic leaflet that spans the entire width of the native anterior leaflet and the anterior prosthetic leaflet moves away from left ventricular outflow tract during systole to create a clear unobstructed outflow path.

9 Claims, 37 Drawing Sheets

(52) U.S. Cl.
CPC . *A61F 2230/006* (2013.01); *A61F 2230/0034* (2013.01); *A61F 2230/0069* (2013.01)

(56) References Cited

U.S. PATENT DOCUMENTS

| | | | |
|---|---|---|---|
| 6,425,916 B1 * | 7/2002 | Garrison | A61F 2/2418 623/1.26 |
| 7,273,493 B2 | 9/2007 | Ledergerber | |
| 7,771,467 B2 | 8/2010 | Svensson | |
| 7,871,435 B2 | 1/2011 | Carpentier et al. | |
| 8,579,964 B2 | 11/2013 | Lane et al. | |
| 2004/0117009 A1 | 6/2004 | Cali et al. | |
| 2004/0181238 A1 | 9/2004 | Zarbatany et al. | |
| 2006/0259136 A1 | 11/2006 | Nguyen et al. | |
| 2006/0282157 A1 | 12/2006 | Hill et al. | |
| 2006/0293745 A1 | 12/2006 | Carpentier et al. | |
| 2007/0050021 A1 | 3/2007 | Johnson | |
| 2011/0319989 A1 | 12/2011 | Lane et al. | |
| 2012/0239143 A1 | 9/2012 | Rankin et al. | |
| 2013/0211508 A1 | 8/2013 | Lane et al. | |
| 2014/0039611 A1 | 2/2014 | Lane et al. | |
| 2014/0052237 A1 | 2/2014 | Lane et al. | |
| 2014/0155990 A1 | 6/2014 | Nyuli et al. | |
| 2014/0257467 A1 | 9/2014 | Lane et al. | |
| 2014/0343669 A1 | 11/2014 | Lane et al. | |
| 2015/0216655 A1 | 8/2015 | Lane et al. | |
| 2015/0257878 A1 | 9/2015 | Lane et al. | |
| 2016/0113764 A1 | 4/2016 | Sheahan et al. | |
| 2016/0157999 A1 | 6/2016 | Lane et al. | |
| 2017/0165064 A1 | 6/2017 | Nyuli et al. | |
| 2017/0216023 A1 | 8/2017 | Lane et al. | |
| 2017/0231760 A1 | 8/2017 | Lane et al. | |
| 2017/0281336 A1 | 10/2017 | Lane et al. | |
| 2017/0003481 A1 | 12/2017 | Lane et al. | |
| 2018/0325703 A1 | 11/2018 | Shahriari | |
| 2019/0021839 A1 | 1/2019 | Kölbel | |
| 2019/0358032 A1 | 11/2019 | Lane et al. | |
| 2020/0015965 A1 | 1/2020 | Lane et al. | |
| 2020/0146818 A1 | 5/2020 | Lane et al. | |
| 2020/0323637 A1 | 10/2020 | Banai et al. | |

FOREIGN PATENT DOCUMENTS

| | | |
|---|---|---|
| CA | 2619080 A1 | 3/2007 |
| CA | 2797863 A1 | 11/2011 |
| CA | 3043737 A1 | 11/2011 |
| CA | 3007670 A1 | 8/2017 |
| CA | 2874219 C | 7/2020 |
| CN | 101262833 A | 9/2008 |
| CN | 102639179 A | 8/2012 |
| CN | 103079498 A | 5/2013 |
| CN | 105283149 A | 1/2016 |
| CN | 105287050 A | 2/2016 |
| CN | 108882981 A | 11/2018 |
| CN | 113633435 A | 11/2021 |
| DE | 10103955 B4 | 11/2001 |
| DE | 10033858 B4 | 1/2002 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 202011111106.0 U1 | 3/2020 |
| DE | 202011111107.9 U1 | 3/2020 |
| DE | 202017007326 U1 | 10/2020 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |

(56) References Cited

FOREIGN PATENT DOCUMENTS

| | | | |
|---|---|---|---|
| EP | 1212011 | B1 | 11/2006 |
| EP | 1261294 | B1 | 11/2006 |
| EP | 1318775 | B1 | 11/2006 |
| EP | 1429690 | B1 | 11/2006 |
| EP | 1173111 | B1 | 12/2006 |
| EP | 1239795 | B1 | 12/2006 |
| EP | 1299049 | B1 | 12/2006 |
| EP | 1487382 | B1 | 12/2006 |
| EP | 1112044 | B1 | 1/2007 |
| EP | 1482997 | B1 | 1/2007 |
| EP | 1117352 | B1 | 2/2007 |
| EP | 1128849 | B1 | 2/2007 |
| EP | 1392666 | B1 | 2/2007 |
| EP | 1474077 | B1 | 2/2007 |
| EP | 1251805 | B1 | 3/2007 |
| EP | 1117334 | B1 | 4/2007 |
| EP | 1263484 | B1 | 5/2007 |
| EP | 1313410 | B1 | 5/2007 |
| EP | 1370200 | B1 | 5/2007 |
| EP | 1560526 | B1 | 6/2007 |
| EP | 1173117 | B1 | 7/2007 |
| EP | 1434615 | B1 | 7/2007 |
| EP | 1465546 | B1 | 7/2007 |
| EP | 1499366 | B1 | 7/2007 |
| EP | 1225948 | B1 | 8/2007 |
| EP | 1519962 | B1 | 9/2007 |
| EP | 1337285 | B1 | 10/2007 |
| EP | 1112042 | B1 | 11/2007 |
| EP | 1148821 | B1 | 11/2007 |
| EP | 1143882 | B1 | 12/2007 |
| EP | 1330189 | B1 | 12/2007 |
| EP | 1489996 | B1 | 12/2007 |
| EP | 1296618 | B1 | 1/2008 |
| EP | 1401356 | B1 | 1/2008 |
| EP | 1629795 | B1 | 1/2008 |
| EP | 1128786 | B1 | 2/2008 |
| EP | 1616532 | B1 | 2/2008 |
| EP | 1289447 | B1 | 3/2008 |
| EP | 1895942 | A2 | 3/2008 |
| EP | 1115353 | B1 | 5/2008 |
| EP | 1330190 | B1 | 5/2008 |
| EP | 1924223 | A1 | 5/2008 |
| EP | 1383448 | B1 | 6/2008 |
| EP | 1251804 | B1 | 7/2008 |
| EP | 1294310 | B1 | 7/2008 |
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1622548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 2040645 | A1 | 4/2009 |
| EP | 1250165 | B1 | 5/2009 |
| EP | 1842508 | B1 | 6/2009 |
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1472996 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511445 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |
| EP | 1968491 | B1 | 7/2010 |

(56) References Cited

FOREIGN PATENT DOCUMENTS

| | | | |
|---|---|---|---|
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |
| EP | 1768610 | B1 | 12/2010 |
| EP | 1827314 | B1 | 12/2010 |
| EP | 1940321 | B1 | 12/2010 |
| EP | 1964532 | B1 | 12/2010 |
| EP | 2078498 | B1 | 12/2010 |
| EP | 1600182 | B1 | 1/2011 |
| EP | 1617789 | B1 | 1/2011 |
| EP | 1663332 | B1 | 1/2011 |
| EP | 2147659 | B1 | 1/2011 |
| EP | 2268231 | A2 | 1/2011 |
| EP | 2273951 | A1 | 1/2011 |
| EP | 1187582 | B1 | 2/2011 |
| EP | 1450733 | B1 | 2/2011 |
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538883 | A1 | 1/2013 |

(56) References Cited

FOREIGN PATENT DOCUMENTS

| | | | |
|---|---|---|---|
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2566416 | A1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |
| EP | 2298237 | B1 | 7/2013 |
| EP | 2309949 | B1 | 7/2013 |
| EP | 2608741 | A2 | 7/2013 |
| EP | 2611389 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1804860 | B1 | 4/2014 |
| EP | 1926455 | B1 | 4/2014 |
| EP | 2081519 | B1 | 4/2014 |
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2258316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545884 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2779945 | A1 | 9/2014 |
| EP | 1853199 | B1 | 10/2014 |
| EP | 2133039 | B1 | 10/2014 |
| EP | 2549955 | B1 | 10/2014 |
| EP | 2549956 | B1 | 10/2014 |
| EP | 2651335 | B1 | 10/2014 |
| EP | 2785281 | A1 | 10/2014 |
| EP | 2793743 | A1 | 10/2014 |
| EP | 2793752 | A1 | 10/2014 |
| EP | 2049721 | B1 | 11/2014 |
| EP | 2142143 | B1 | 11/2014 |
| EP | 2229921 | B1 | 11/2014 |
| EP | 2288403 | B1 | 11/2014 |
| EP | 2415421 | B1 | 11/2014 |
| EP | 1551274 | B1 | 12/2014 |
| EP | 1768735 | B1 | 12/2014 |
| EP | 1959865 | B1 | 12/2014 |
| EP | 2077718 | B1 | 12/2014 |

(56) References Cited

FOREIGN PATENT DOCUMENTS

| | | | |
|---|---|---|---|
| EP | 2303185 B1 | 12/2014 |
| EP | 2334857 B1 | 12/2014 |
| EP | 2365840 B1 | 12/2014 |
| EP | 2420207 B1 | 12/2014 |
| EP | 2422750 B1 | 12/2014 |
| EP | 2707073 B1 | 12/2014 |
| EP | 1768630 B1 | 1/2015 |
| EP | 2254515 B1 | 1/2015 |
| EP | 2641569 B1 | 1/2015 |
| EP | 2709559 B1 | 1/2015 |
| EP | 2825203 A1 | 1/2015 |
| EP | 1903990 B1 | 2/2015 |
| EP | 2255753 B1 | 2/2015 |
| EP | 2335649 B1 | 2/2015 |
| EP | 2522308 B1 | 2/2015 |
| EP | 2591754 B1 | 2/2015 |
| EP | 2835112 A1 | 2/2015 |
| EP | 1861045 B1 | 3/2015 |
| EP | 2029057 B1 | 3/2015 |
| EP | 2193761 B1 | 3/2015 |
| EP | 2379010 B1 | 3/2015 |
| EP | 2416737 B1 | 3/2015 |
| EP | 1791495 B1 | 4/2015 |
| EP | 2298252 B1 | 4/2015 |
| EP | 2536359 B1 | 4/2015 |
| EP | 2538879 B1 | 4/2015 |
| EP | 2609894 B1 | 4/2015 |
| EP | 2693984 B1 | 4/2015 |
| EP | 2712633 B1 | 4/2015 |
| EP | 2747707 B1 | 4/2015 |
| EP | 2862546 A1 | 4/2015 |
| EP | 2863842 A1 | 4/2015 |
| EP | 1465555 B1 | 5/2015 |
| EP | 1924224 B1 | 5/2015 |
| EP | 1992369 B1 | 5/2015 |
| EP | 2410947 B1 | 5/2015 |
| EP | 2484311 B1 | 5/2015 |
| EP | 2654616 B1 | 5/2015 |
| EP | 2866741 A1 | 5/2015 |
| EP | 1646332 B1 | 6/2015 |
| EP | 2745805 B1 | 6/2015 |
| EP | 2749254 B1 | 6/2015 |
| EP | 2877123 A2 | 6/2015 |
| EP | 2882374 A1 | 6/2015 |
| EP | 2884906 A1 | 6/2015 |
| EP | 1729685 B1 | 7/2015 |
| EP | 1976439 B1 | 7/2015 |
| EP | 2068767 B1 | 7/2015 |
| EP | 2068769 B1 | 7/2015 |
| EP | 2444031 B1 | 7/2015 |
| EP | 2455041 B1 | 7/2015 |
| EP | 2498719 B1 | 7/2015 |
| EP | 2558030 B1 | 7/2015 |
| EP | 2752209 B1 | 7/2015 |
| EP | 2892467 A1 | 7/2015 |
| EP | 1702247 B1 | 8/2015 |
| EP | 1729688 B1 | 8/2015 |
| EP | 1887979 B1 | 8/2015 |
| EP | 2032079 B1 | 8/2015 |
| EP | 2219558 B1 | 8/2015 |
| EP | 2234657 B1 | 8/2015 |
| EP | 2250976 B1 | 8/2015 |
| EP | 2262447 B1 | 8/2015 |
| EP | 2303384 B1 | 8/2015 |
| EP | 2387365 B1 | 8/2015 |
| EP | 2560579 B1 | 8/2015 |
| EP | 2575621 B1 | 8/2015 |
| EP | 2590595 B1 | 8/2015 |
| EP | 2709560 B1 | 8/2015 |
| EP | 2755603 B1 | 8/2015 |
| EP | 2906147 A1 | 8/2015 |
| EP | 1534185 B1 | 9/2015 |
| EP | 1765225 B1 | 9/2015 |
| EP | 1778127 B1 | 9/2015 |
| EP | 2094194 B1 | 9/2015 |
| EP | 2201911 B1 | 9/2015 |
| EP | 2306934 B1 | 9/2015 |
| EP | 2397113 B1 | 9/2015 |
| EP | 2453843 B1 | 9/2015 |
| EP | 2459127 B1 | 9/2015 |
| EP | 2675396 B1 | 9/2015 |
| EP | 2675397 B1 | 9/2015 |
| EP | 2736454 B1 | 9/2015 |
| EP | 2754414 A4 | 9/2015 |
| EP | 2790609 B1 | 9/2015 |
| EP | 2805693 B1 | 9/2015 |
| EP | 2916781 A2 | 9/2015 |
| EP | 1734903 B1 | 10/2015 |
| EP | 1863546 B1 | 10/2015 |
| EP | 1900343 B1 | 10/2015 |
| EP | 2081515 B1 | 10/2015 |
| EP | 2191792 B1 | 10/2015 |
| EP | 2254513 B1 | 10/2015 |
| EP | 2381896 B1 | 10/2015 |
| EP | 2450008 B1 | 10/2015 |
| EP | 2544626 B1 | 10/2015 |
| EP | 2561830 B1 | 10/2015 |
| EP | 2600798 B1 | 10/2015 |
| EP | 2626039 B1 | 10/2015 |
| EP | 2647354 B1 | 10/2015 |
| EP | 2729093 B1 | 10/2015 |
| EP | 2836165 B1 | 10/2015 |
| EP | 1863545 B1 | 11/2015 |
| EP | 2303395 B1 | 11/2015 |
| EP | 2497446 B1 | 11/2015 |
| EP | 2772228 B1 | 11/2015 |
| EP | 1482869 B1 | 12/2015 |
| EP | 1551473 B1 | 12/2015 |
| EP | 1748745 B1 | 12/2015 |
| EP | 1755459 B1 | 12/2015 |
| EP | 1850796 B1 | 12/2015 |
| EP | 1922030 B1 | 12/2015 |
| EP | 1954212 B1 | 12/2015 |
| EP | 2424472 B1 | 12/2015 |
| EP | 2470120 B1 | 12/2015 |
| EP | 2542179 B1 | 12/2015 |
| EP | 2948100 A1 | 12/2015 |
| EP | 1991168 B1 | 1/2016 |
| EP | 2254512 B1 | 1/2016 |
| EP | 2422748 B1 | 1/2016 |
| EP | 2967700 A1 | 1/2016 |
| EP | 2967807 A2 | 1/2016 |
| EP | 2967834 A1 | 1/2016 |
| EP | 2967856 A1 | 1/2016 |
| EP | 2967860 A1 | 1/2016 |
| EP | 2967866 A2 | 1/2016 |
| EP | 2977026 A1 | 1/2016 |
| EP | 1754684 B1 | 2/2016 |
| EP | 1835948 B1 | 2/2016 |
| EP | 2012712 B1 | 2/2016 |
| EP | 2285318 B1 | 2/2016 |
| EP | 2731550 B1 | 2/2016 |
| EP | 2926766 B1 | 2/2016 |
| EP | 2982337 A1 | 2/2016 |
| EP | 1585463 B1 | 3/2016 |
| EP | 1638621 B1 | 3/2016 |
| EP | 1804726 B1 | 3/2016 |
| EP | 1865886 B1 | 3/2016 |
| EP | 1887982 B1 | 3/2016 |
| EP | 2150205 B1 | 3/2016 |
| EP | 2278944 B1 | 3/2016 |
| EP | 2291126 B1 | 3/2016 |
| EP | 2517674 B1 | 3/2016 |
| EP | 2520253 B1 | 3/2016 |
| EP | 2526897 B1 | 3/2016 |
| EP | 2670353 B1 | 3/2016 |
| EP | 2674130 B1 | 3/2016 |
| EP | 2780042 B1 | 3/2016 |
| EP | 2991584 A1 | 3/2016 |
| EP | 2991587 A2 | 3/2016 |
| EP | 2994072 A1 | 3/2016 |
| EP | 2994075 A1 | 3/2016 |
| EP | 2996632 A1 | 3/2016 |
| EP | 2996633 A1 | 3/2016 |

(56) References Cited

FOREIGN PATENT DOCUMENTS

| | | | |
|---|---|---|---|
| EP | 2996641 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2626040 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2934387 | B1 | 10/2016 |
| EP | 3076901 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |

(56) References Cited

FOREIGN PATENT DOCUMENTS

| | | | |
|---|---|---|---|
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |

(56) References Cited

FOREIGN PATENT DOCUMENTS

| | | | |
|---|---|---|---|
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277222 | A1 | 2/2018 |
| EP | 3281608 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |
| EP | 3298970 | A1 | 3/2018 |
| EP | 3298987 | A1 | 3/2018 |
| EP | 2209440 | B1 | 4/2018 |
| EP | 2536357 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |

(56) References Cited

FOREIGN PATENT DOCUMENTS

| | | |
|---|---|---|
| EP | 2900150 B1 | 4/2018 |
| EP | 2908779 B1 | 4/2018 |
| EP | 2922502 B1 | 4/2018 |
| EP | 2964441 B1 | 4/2018 |
| EP | 2967868 B1 | 4/2018 |
| EP | 2979665 B1 | 4/2018 |
| EP | 2994073 B1 | 4/2018 |
| EP | 3095394 B1 | 4/2018 |
| EP | 3128927 A4 | 4/2018 |
| EP | 3134033 B1 | 4/2018 |
| EP | 3137146 A4 | 4/2018 |
| EP | 3280482 A4 | 4/2018 |
| EP | 3302362 A1 | 4/2018 |
| EP | 3308745 A1 | 4/2018 |
| EP | 3310301 A1 | 4/2018 |
| EP | 1945112 B1 | 5/2018 |
| EP | 2007313 B1 | 5/2018 |
| EP | 2316381 B2 | 5/2018 |
| EP | 2377469 B1 | 5/2018 |
| EP | 2531115 B1 | 5/2018 |
| EP | 2561831 B1 | 5/2018 |
| EP | 2605724 B1 | 5/2018 |
| EP | 2723277 B1 | 5/2018 |
| EP | 2741711 B1 | 5/2018 |
| EP | 2755573 B1 | 5/2018 |
| EP | 2768429 B1 | 5/2018 |
| EP | 2819618 B1 | 5/2018 |
| EP | 2833836 B1 | 5/2018 |
| EP | 2886083 B1 | 5/2018 |
| EP | 2926840 B1 | 5/2018 |
| EP | 2943157 B1 | 5/2018 |
| EP | 2948099 B1 | 5/2018 |
| EP | 3000437 B1 | 5/2018 |
| EP | 3145448 B1 | 5/2018 |
| EP | 3154475 B1 | 5/2018 |
| EP | 3316819 A1 | 5/2018 |
| EP | 3316821 A1 | 5/2018 |
| EP | 3322381 A1 | 5/2018 |
| EP | 3323353 A1 | 5/2018 |
| EP | 3323439 A1 | 5/2018 |
| EP | 3324892 A1 | 5/2018 |
| EP | 3326584 A1 | 5/2018 |
| EP | 2150312 B1 | 6/2018 |
| EP | 2379322 B1 | 6/2018 |
| EP | 2400925 B1 | 6/2018 |
| EP | 2552355 B1 | 6/2018 |
| EP | 2560589 B1 | 6/2018 |
| EP | 2563277 B1 | 6/2018 |
| EP | 2661305 B1 | 6/2018 |
| EP | 2736456 B1 | 6/2018 |
| EP | 2782523 B1 | 6/2018 |
| EP | 3056170 B1 | 6/2018 |
| EP | 3062745 B1 | 6/2018 |
| EP | 3130320 B1 | 6/2018 |
| EP | 3187150 B1 | 6/2018 |
| EP | 3334380 A1 | 6/2018 |
| EP | 3334381 A1 | 6/2018 |
| EP | 3337412 A1 | 6/2018 |
| EP | 3337424 A1 | 6/2018 |
| EP | 2478872 B1 | 7/2018 |
| EP | 2563278 B1 | 7/2018 |
| EP | 2616004 B1 | 7/2018 |
| EP | 2779943 B1 | 7/2018 |
| EP | 2802290 B1 | 7/2018 |
| EP | 2816980 B1 | 7/2018 |
| EP | 2938293 B1 | 7/2018 |
| EP | 3107496 B1 | 7/2018 |
| EP | 3178450 B1 | 7/2018 |
| EP | 3212097 B1 | 7/2018 |
| EP | 3340936 A1 | 7/2018 |
| EP | 3342355 A1 | 7/2018 |
| EP | 3342377 A1 | 7/2018 |
| EP | 3348235 A1 | 7/2018 |
| EP | 2536354 B1 | 8/2018 |
| EP | 2616006 B1 | 8/2018 |
| EP | 2797556 B1 | 8/2018 |
| EP | 2822473 B1 | 8/2018 |
| EP | 2854711 B1 | 8/2018 |
| EP | 2866847 B1 | 8/2018 |
| EP | 2918246 B1 | 8/2018 |
| EP | 2967845 B1 | 8/2018 |
| EP | 2999436 B1 | 8/2018 |
| EP | 3013281 B1 | 8/2018 |
| EP | 3060170 B1 | 8/2018 |
| EP | 3104811 B1 | 8/2018 |
| EP | 3143944 B1 | 8/2018 |
| EP | 3157467 B1 | 8/2018 |
| EP | 3193791 B1 | 8/2018 |
| EP | 3241526 B1 | 8/2018 |
| EP | 3355800 A1 | 8/2018 |
| EP | 3360513 A1 | 8/2018 |
| EP | 3360514 A1 | 8/2018 |
| EP | 3361988 A1 | 8/2018 |
| EP | 2114305 B1 | 9/2018 |
| EP | 2155115 B1 | 9/2018 |
| EP | 2601910 B1 | 9/2018 |
| EP | 2617390 B1 | 9/2018 |
| EP | 2734157 B1 | 9/2018 |
| EP | 2968674 B1 | 9/2018 |
| EP | 2999415 B1 | 9/2018 |
| EP | 3106130 B1 | 9/2018 |
| EP | 3151763 B1 | 9/2018 |
| EP | 3213717 B1 | 9/2018 |
| EP | 3245985 B1 | 9/2018 |
| EP | 3367979 A1 | 9/2018 |
| EP | 1827256 B1 | 10/2018 |
| EP | 1850790 B1 | 10/2018 |
| EP | 2063823 B1 | 10/2018 |
| EP | 2124825 B1 | 10/2018 |
| EP | 2249746 B1 | 10/2018 |
| EP | 2254514 B1 | 10/2018 |
| EP | 2285309 B1 | 10/2018 |
| EP | 2455042 B1 | 10/2018 |
| EP | 2571561 B1 | 10/2018 |
| EP | 2616008 B1 | 10/2018 |
| EP | 2647393 B1 | 10/2018 |
| EP | 2739214 B1 | 10/2018 |
| EP | 2739247 B1 | 10/2018 |
| EP | 2776114 B1 | 10/2018 |
| EP | 2836171 B1 | 10/2018 |
| EP | 2842581 B1 | 10/2018 |
| EP | 2870946 B1 | 10/2018 |
| EP | 2923665 B1 | 10/2018 |
| EP | 2964277 B1 | 10/2018 |
| EP | 3001978 B1 | 10/2018 |
| EP | 3010562 B1 | 10/2018 |
| EP | 3072475 B1 | 10/2018 |
| EP | 3081161 B1 | 10/2018 |
| EP | 3081195 B1 | 10/2018 |
| EP | 3099345 B1 | 10/2018 |
| EP | 3120809 B1 | 10/2018 |
| EP | 3238663 B1 | 10/2018 |
| EP | 3275404 A4 | 10/2018 |
| EP | 3384879 A1 | 10/2018 |
| EP | 1708650 B1 | 11/2018 |
| EP | 1945143 B1 | 11/2018 |
| EP | 2205183 B1 | 11/2018 |
| EP | 2663258 B1 | 11/2018 |
| EP | 2790615 B1 | 11/2018 |
| EP | 2854709 B1 | 11/2018 |
| EP | 2898859 B1 | 11/2018 |
| EP | 2921139 B1 | 11/2018 |
| EP | 2928538 B1 | 11/2018 |
| EP | 3075354 B1 | 11/2018 |
| EP | 3082949 B1 | 11/2018 |
| EP | 3145452 B1 | 11/2018 |
| EP | 3216424 B1 | 11/2018 |
| EP | 3260084 B1 | 11/2018 |
| EP | 3400908 A1 | 11/2018 |
| EP | 3405139 A1 | 11/2018 |
| EP | 1858450 B1 | 12/2018 |
| EP | 2150208 B1 | 12/2018 |
| EP | 2326261 B1 | 12/2018 |
| EP | 2344075 B1 | 12/2018 |

(56) References Cited

FOREIGN PATENT DOCUMENTS

| | | | |
|---|---|---|---|
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3410987 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3332743 | B1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3435919 | A1 | 2/2019 |
| EP | 3441045 | A1 | 2/2019 |
| EP | 3442469 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3454785 | A1 | 3/2019 |
| EP | 3454786 | A1 | 3/2019 |
| EP | 3454794 | A1 | 3/2019 |
| EP | 3457987 | A1 | 3/2019 |
| EP | 3457988 | A1 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3479797 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |

(56) References Cited

FOREIGN PATENT DOCUMENTS

| | | | |
|---|---|---|---|
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 1861043 | B1 | 8/2019 |
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3348233 | B1 | 8/2019 |
| EP | 3366262 | B1 | 8/2019 |
| EP | 3527170 | A1 | 8/2019 |
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |
| EP | 3531975 | A1 | 9/2019 |
| EP | 3534840 | A1 | 9/2019 |
| EP | 3534845 | A2 | 9/2019 |
| EP | 3535010 | A1 | 9/2019 |
| EP | 3538027 | A1 | 9/2019 |
| EP | 3539508 | A1 | 9/2019 |
| EP | 3539509 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |
| EP | 2674174 | B1 | 10/2019 |
| EP | 2811923 | B1 | 10/2019 |
| EP | 2901967 | B1 | 10/2019 |
| EP | 3010431 | B1 | 10/2019 |
| EP | 3019091 | B1 | 10/2019 |
| EP | 3019123 | B1 | 10/2019 |
| EP | 3057522 | B1 | 10/2019 |
| EP | 3067075 | B1 | 10/2019 |
| EP | 3146937 | B1 | 10/2019 |
| EP | 3238777 | B1 | 10/2019 |
| EP | 3359211 | B1 | 10/2019 |
| EP | 3388026 | B1 | 10/2019 |
| EP | 3432806 | B1 | 10/2019 |
| EP | 3496626 | A4 | 10/2019 |
| EP | 3544548 | A1 | 10/2019 |
| EP | 3547936 | A1 | 10/2019 |
| EP | 3547966 | A1 | 10/2019 |
| EP | 3549555 | A1 | 10/2019 |
| EP | 3558165 | A1 | 10/2019 |
| EP | 3558168 | A1 | 10/2019 |
| EP | 3558169 | A2 | 10/2019 |
| EP | 2043559 | B1 | 11/2019 |
| EP | 2358308 | B1 | 11/2019 |
| EP | 2405863 | B1 | 11/2019 |
| EP | 2701633 | B1 | 11/2019 |
| EP | 2898857 | B1 | 11/2019 |
| EP | 2967853 | B1 | 11/2019 |
| EP | 3009104 | B1 | 11/2019 |
| EP | 3021792 | B1 | 11/2019 |
| EP | 3076900 | B1 | 11/2019 |
| EP | 3111889 | B1 | 11/2019 |
| EP | 3142607 | B1 | 11/2019 |
| EP | 3167850 | B1 | 11/2019 |
| EP | 3397205 | B1 | 11/2019 |
| EP | 3572117 | A1 | 11/2019 |
| EP | 3479800 | A4 | 12/2019 |
| EP | 3576677 | A1 | 12/2019 |
| EP | 3579761 | A2 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3600159 | A1 | 2/2020 |
| EP | 3606472 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3175822 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |

(56) References Cited

FOREIGN PATENT DOCUMENTS

| | | |
|---|---|---|
| EP | 3626208 A1 | 3/2020 |
| EP | 1667614 B2 | 4/2020 |
| EP | 2119417 B2 | 4/2020 |
| EP | 2155114 B1 | 4/2020 |
| EP | 2299937 B1 | 4/2020 |
| EP | 2331016 B1 | 4/2020 |
| EP | 2376013 B8 | 4/2020 |
| EP | 2413843 B1 | 4/2020 |
| EP | 2854705 B1 | 4/2020 |
| EP | 2918249 B1 | 4/2020 |
| EP | 2922593 B1 | 4/2020 |
| EP | 2950753 B1 | 4/2020 |
| EP | 2967810 B1 | 4/2020 |
| EP | 3110367 B1 | 4/2020 |
| EP | 3111888 B1 | 4/2020 |
| EP | 3128927 B1 | 4/2020 |
| EP | 3134032 B1 | 4/2020 |
| EP | 3142606 B1 | 4/2020 |
| EP | 3270825 B1 | 4/2020 |
| EP | 3300696 B1 | 4/2020 |
| EP | 3316823 B1 | 4/2020 |
| EP | 3334487 B1 | 4/2020 |
| EP | 3342355 B1 | 4/2020 |
| EP | 3373863 B1 | 4/2020 |
| EP | 3459498 B1 | 4/2020 |
| EP | 3470105 B1 | 4/2020 |
| EP | 3632338 A1 | 4/2020 |
| EP | 3636312 A1 | 4/2020 |
| EP | 3639792 A1 | 4/2020 |
| EP | 3639888 A1 | 4/2020 |
| EP | 3643273 A1 | 4/2020 |
| EP | 1895942 B1 | 5/2020 |
| EP | 2120821 B1 | 5/2020 |
| EP | 2437688 B1 | 5/2020 |
| EP | 2785281 B1 | 5/2020 |
| EP | 2852354 B1 | 5/2020 |
| EP | 2884906 B1 | 5/2020 |
| EP | 2999412 B1 | 5/2020 |
| EP | 3060174 B1 | 5/2020 |
| EP | 3071147 B1 | 5/2020 |
| EP | 3104812 B1 | 5/2020 |
| EP | 3139861 B1 | 5/2020 |
| EP | 3232989 B1 | 5/2020 |
| EP | 3294219 B1 | 5/2020 |
| EP | 3298970 B1 | 5/2020 |
| EP | 3302366 B1 | 5/2020 |
| EP | 3323389 B1 | 5/2020 |
| EP | 3332744 B1 | 5/2020 |
| EP | 3402440 B1 | 5/2020 |
| EP | 3417813 B1 | 5/2020 |
| EP | 3417831 B1 | 5/2020 |
| EP | 3457987 B1 | 5/2020 |
| EP | 3484413 B1 | 5/2020 |
| EP | 3531975 B1 | 5/2020 |
| EP | 3644866 A1 | 5/2020 |
| EP | 3646822 A1 | 5/2020 |
| EP | 3646824 A1 | 5/2020 |
| EP | 3646825 A1 | 5/2020 |
| EP | 3656354 A1 | 5/2020 |
| EP | 1648339 B2 | 6/2020 |
| EP | 2072027 B1 | 6/2020 |
| EP | 2331016 B8 | 6/2020 |
| EP | 2616007 B1 | 6/2020 |
| EP | 2967856 B1 | 6/2020 |
| EP | 3042635 B1 | 6/2020 |
| EP | 3060165 B1 | 6/2020 |
| EP | 3280338 B1 | 6/2020 |
| EP | 3283010 B1 | 6/2020 |
| EP | 3400908 B1 | 6/2020 |
| EP | 3494928 B1 | 6/2020 |
| EP | 3498225 B1 | 6/2020 |
| EP | 3583920 B1 | 6/2020 |
| EP | 3659553 A1 | 6/2020 |
| EP | 3668450 A1 | 6/2020 |
| EP | 3668452 A1 | 6/2020 |
| EP | 3669828 A1 | 6/2020 |
| EP | 3669829 A1 | 6/2020 |
| EP | 2271284 B1 | 7/2020 |
| EP | 2291145 B1 | 7/2020 |
| EP | 2512952 B1 | 7/2020 |
| EP | 2558029 B1 | 7/2020 |
| EP | 2693985 B1 | 7/2020 |
| EP | 2858708 B1 | 7/2020 |
| EP | 2862546 B1 | 7/2020 |
| EP | 2967807 B1 | 7/2020 |
| EP | 2967866 B1 | 7/2020 |
| EP | 3061421 B1 | 7/2020 |
| EP | 3107497 B1 | 7/2020 |
| EP | 3139862 B1 | 7/2020 |
| EP | 3423000 B1 | 7/2020 |
| EP | 3441045 B1 | 7/2020 |
| EP | 3451972 B1 | 7/2020 |
| EP | 3501454 B1 | 7/2020 |
| EP | 3512466 B1 | 7/2020 |
| EP | 3616652 B1 | 7/2020 |
| EP | 3672528 A1 | 7/2020 |
| EP | 3672529 A1 | 7/2020 |
| EP | 3673925 A1 | 7/2020 |
| EP | 3679894 A1 | 7/2020 |
| EP | 3681439 A1 | 7/2020 |
| EP | 3681441 A1 | 7/2020 |
| EP | 3682852 A1 | 7/2020 |
| EP | 3682854 A1 | 7/2020 |
| EP | 2367505 B1 | 8/2020 |
| EP | 2497445 B1 | 8/2020 |
| EP | 2537486 B1 | 8/2020 |
| EP | 2777616 B1 | 8/2020 |
| EP | 3007651 B1 | 8/2020 |
| EP | 3052053 B1 | 8/2020 |
| EP | 3237033 B1 | 8/2020 |
| EP | 3388005 B1 | 8/2020 |
| EP | 3410986 B1 | 8/2020 |
| EP | 3451974 B1 | 8/2020 |
| EP | 3463192 B1 | 8/2020 |
| EP | 3554423 B1 | 8/2020 |
| EP | 3568089 A4 | 8/2020 |
| EP | 3573544 B1 | 8/2020 |
| EP | 3634255 B1 | 8/2020 |
| EP | 3689299 A1 | 8/2020 |
| EP | 3691567 A1 | 8/2020 |
| EP | 3697346 A1 | 8/2020 |
| EP | 2485795 B1 | 9/2020 |
| EP | 3125777 B1 | 9/2020 |
| EP | 3182930 B1 | 9/2020 |
| EP | 3285690 B1 | 9/2020 |
| EP | 3459500 B1 | 9/2020 |
| EP | 3570782 B1 | 9/2020 |
| EP | 3700467 A1 | 9/2020 |
| EP | 3711711 A1 | 9/2020 |
| EP | 3714936 A1 | 9/2020 |
| EP | 2979667 B2 | 10/2020 |
| EP | 3193783 B1 | 10/2020 |
| EP | 3490501 B1 | 10/2020 |
| EP | 3720363 A1 | 10/2020 |
| EP | 2387973 B1 | 11/2020 |
| EP | 2427144 B1 | 11/2020 |
| EP | 2506777 B1 | 11/2020 |
| EP | 2793743 B1 | 11/2020 |
| EP | 2825203 B1 | 11/2020 |
| EP | 2863842 B1 | 11/2020 |
| EP | 2967700 B1 | 11/2020 |
| EP | 2977026 B1 | 11/2020 |
| EP | 3139864 B1 | 11/2020 |
| EP | 3145451 B1 | 11/2020 |
| EP | 3156007 B1 | 11/2020 |
| EP | 3244834 B1 | 11/2020 |
| EP | 3298987 B1 | 11/2020 |
| EP | 3302362 B1 | 11/2020 |
| EP | 3311777 B1 | 11/2020 |
| EP | 3316819 B1 | 11/2020 |
| EP | 3361988 B1 | 11/2020 |
| EP | 3503813 B1 | 11/2020 |
| EP | 3527170 B1 | 11/2020 |
| EP | 3530236 B1 | 11/2020 |

(56) References Cited

FOREIGN PATENT DOCUMENTS

| | | | |
|---|---|---|---|
| EP | 3590471 B1 | 11/2020 |
| EP | 3593762 B1 | 11/2020 |
| EP | 3740162 A1 | 11/2020 |
| EP | 2370138 B1 | 12/2020 |
| EP | 2445450 B1 | 12/2020 |
| EP | 2739250 B1 | 12/2020 |
| EP | 2877123 B1 | 12/2020 |
| EP | 2967834 B1 | 12/2020 |
| EP | 2996632 B1 | 12/2020 |
| EP | 3090703 B1 | 12/2020 |
| EP | 3191025 B1 | 12/2020 |
| EP | 3202371 B1 | 12/2020 |
| EP | 3316822 B1 | 12/2020 |
| EP | 3334382 B1 | 12/2020 |
| EP | 3337424 B1 | 12/2020 |
| EP | 3367896 B1 | 12/2020 |
| EP | 3368582 B1 | 12/2020 |
| EP | 3476366 B1 | 12/2020 |
| EP | 3481303 B1 | 12/2020 |
| EP | 3538028 B1 | 12/2020 |
| EP | 3539510 B1 | 12/2020 |
| EP | 3544548 B1 | 12/2020 |
| EP | 3545906 B1 | 12/2020 |
| EP | 3572117 B1 | 12/2020 |
| EP | 3593763 B1 | 12/2020 |
| EP | 3749254 A1 | 12/2020 |
| EP | 3753535 A1 | 12/2020 |
| EP | 339720881 | 12/2020 |
| EP | 1906883 B1 | 1/2021 |
| EP | 2334261 B1 | 1/2021 |
| EP | 2349096 B1 | 1/2021 |
| EP | 2568924 B1 | 1/2021 |
| EP | 2699202 B1 | 1/2021 |
| EP | 2713894 B1 | 1/2021 |
| EP | 2835112 B1 | 1/2021 |
| EP | 3040054 B1 | 1/2021 |
| EP | 3131502 B1 | 1/2021 |
| EP | 3197397 B1 | 1/2021 |
| EP | 3256178 B1 | 1/2021 |
| EP | 3290007 B1 | 1/2021 |
| EP | 3316821 B1 | 1/2021 |
| EP | 3337412 B1 | 1/2021 |
| EP | 3432834 B1 | 1/2021 |
| EP | 3454786 B1 | 1/2021 |
| EP | 3474778 B1 | 1/2021 |
| EP | 3528748 B1 | 1/2021 |
| EP | 3547966 B1 | 1/2021 |
| EP | 3603576 B1 | 1/2021 |
| EP | 3760164 A1 | 1/2021 |
| EP | 2273951 B1 | 2/2021 |
| EP | 2379008 B1 | 2/2021 |
| EP | 2996641 B1 | 2/2021 |
| EP | 3043747 B1 | 2/2021 |
| EP | 3340936 B1 | 2/2021 |
| EP | 3457985 B1 | 2/2021 |
| EP | 3503847 B1 | 2/2021 |
| EP | 3538027 B1 | 2/2021 |
| EP | 3558168 B1 | 2/2021 |
| EP | 3581232 B1 | 2/2021 |
| EP | 3656354 B1 | 2/2021 |
| EP | 3697324 B1 | 2/2021 |
| EP | 2299938 B1 | 3/2021 |
| EP | 2470121 B1 | 3/2021 |
| EP | 2564811 B1 | 3/2021 |
| EP | 2679198 B1 | 3/2021 |
| EP | 3068346 B1 | 3/2021 |
| EP | 3160394 B1 | 3/2021 |
| EP | 3169245 B1 | 3/2021 |
| EP | 3178443 B1 | 3/2021 |
| EP | 3184081 B1 | 3/2021 |
| EP | 3226956 B1 | 3/2021 |
| EP | 3324892 B1 | 3/2021 |
| EP | 3334354 B1 | 3/2021 |
| EP | 3402446 B1 | 3/2021 |
| EP | 3442469 B1 | 3/2021 |
| EP | 3503851 B1 | 3/2021 |
| EP | 3506855 B1 | 3/2021 |
| EP | 3531979 B1 | 3/2021 |
| EP | 3535010 B1 | 3/2021 |
| EP | 3581151 B1 | 3/2021 |
| EP | 3590472 B1 | 3/2021 |
| EP | 3593760 B1 | 3/2021 |
| EP | 3646825 B1 | 3/2021 |
| EP | 3649985 B1 | 3/2021 |
| EP | 3787561 A1 | 3/2021 |
| EP | 3791795 A1 | 3/2021 |
| EP | 1734872 B1 | 4/2021 |
| EP | 2594230 B1 | 4/2021 |
| EP | 2624785 B1 | 4/2021 |
| EP | 2670349 B1 | 4/2021 |
| EP | 2793752 B1 | 4/2021 |
| EP | 2823769 B1 | 4/2021 |
| EP | 2964152 B1 | 4/2021 |
| EP | 3253331 B1 | 4/2021 |
| EP | 3290004 B1 | 4/2021 |
| EP | 3311778 B1 | 4/2021 |
| EP | 3367979 B1 | 4/2021 |
| EP | 3454794 B1 | 4/2021 |
| EP | 3487420 B1 | 4/2021 |
| EP | 3558165 B1 | 4/2021 |
| EP | 3616651 B1 | 4/2021 |
| EP | 3619136 B1 | 4/2021 |
| EP | 3626208 B1 | 4/2021 |
| EP | 3632379 B1 | 4/2021 |
| EP | 3646823 B1 | 4/2021 |
| EP | 3646824 B1 | 4/2021 |
| EP | 3653173 B1 | 4/2021 |
| EP | 1951155 B1 | 5/2021 |
| EP | 2073755 B1 | 5/2021 |
| EP | 2948100 B1 | 5/2021 |
| EP | 3099270 B1 | 5/2021 |
| EP | 3150172 B1 | 5/2021 |
| EP | 3178445 B1 | 5/2021 |
| EP | 3310301 B1 | 5/2021 |
| EP | 3582697 B1 | 5/2021 |
| EP | 3592295 B1 | 5/2021 |
| EP | 3639888 B1 | 5/2021 |
| EP | 3669828 B1 | 5/2021 |
| EP | 2471492 B1 | 6/2021 |
| EP | 2486894 B1 | 6/2021 |
| EP | 2750630 B1 | 6/2021 |
| EP | 3247312 B1 | 6/2021 |
| EP | 3294215 B1 | 6/2021 |
| EP | 3323353 B1 | 6/2021 |
| EP | 3360513 B1 | 6/2021 |
| EP | 3488821 B1 | 6/2021 |
| EP | 3549555 B1 | 6/2021 |
| EP | 3576677 B1 | 6/2021 |
| EP | 3632338 B1 | 6/2021 |
| EP | 2381895 B1 | 7/2021 |
| EP | 2611389 B1 | 7/2021 |
| EP | 2779945 B1 | 7/2021 |
| EP | 3193740 B1 | 7/2021 |
| EP | 3206629 B1 | 7/2021 |
| EP | 3277222 B1 | 7/2021 |
| EP | 3400907 B1 | 7/2021 |
| EP | 3435919 B1 | 7/2021 |
| EP | 3522800 B1 | 7/2021 |
| EP | 3539508 B1 | 7/2021 |
| EP | 3539509 B1 | 7/2021 |
| EP | 3572044 B1 | 7/2021 |
| EP | 3592289 B1 | 7/2021 |
| EP | 3668450 B1 | 7/2021 |
| EP | 3681439 B1 | 7/2021 |
| EP | 3691567 B1 | 7/2021 |
| EP | 2558032 B1 | 8/2021 |
| EP | 2992857 B1 | 8/2021 |
| EP | 2994075 B1 | 8/2021 |
| EP | 3038539 B1 | 8/2021 |
| EP | 3287099 B1 | 8/2021 |
| EP | 3348235 B1 | 8/2021 |
| EP | 3643273 B1 | 8/2021 |
| EP | 3646822 B1 | 8/2021 |
| EP | 3658215 B1 | 8/2021 |

(56) References Cited

FOREIGN PATENT DOCUMENTS

| | | | |
|---|---|---|---|
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 367252881 | | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 2358307 | B1 | 12/2021 |
| EP | 2765954 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3749254 | B1 | 12/2021 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 2982763 | B1 | 7/2015 |
| FR | 2991162 | B1 | 7/2015 |
| FR | 3006582 | B1 | 7/2015 |
| FR | 3001121 | B1 | 1/2016 |
| FR | 2998166 | B1 | 2/2016 |
| FR | 3021862 | B1 | 5/2016 |
| FR | 3004917 | B1 | 6/2016 |
| FR | 3006884 | B1 | 6/2016 |
| FR | 3023704 | B1 | 8/2016 |
| FR | 3008885 | B1 | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 2407146 | B | 4/2006 |
| GB | 2398245 | B | 3/2007 |
| GB | 2433700 | B | 12/2007 |
| GB | 2478498 | B | 7/2012 |
| GB | 2530487 | B | 12/2016 |
| GB | 2517609 | B | 5/2017 |
| GB | 2538749 | B | 8/2017 |
| GB | 2538072 | B | 11/2017 |
| GB | 2536538 | B | 7/2018 |
| GB | 2548891 | B | 7/2018 |
| JP | 2009505731 | A | 2/2009 |
| JP | 2013525039 | A | 6/2013 |
| JP | 2013526388 | A | 6/2013 |
| JP | 2013539331 | A | 10/2013 |
| JP | 2016185404 | A | 10/2016 |
| JP | 2019069241 | A | 5/2019 |
| JP | 7006940 | B2 | 1/2022 |
| WO | WO-2007024755 | A1 | 3/2007 |
| WO | WO-2009134701 | A2 | 11/2009 |
| WO | WO-2011069048 | A2 | 6/2011 |
| WO | WO-2011137531 | A1 | 11/2011 |
| WO | WO-2016178126 | A1 | 11/2016 |
| WO | WO-2017127939 | A1 | 8/2017 |
| WO | WO-2020210652 | A1 | 10/2020 |

OTHER PUBLICATIONS

"International Application Serial No. PCT/US2020/027705, International Search Report dated Jul. 24, 2020", 2 pgs.

(56) References Cited

OTHER PUBLICATIONS

"International Application Serial No. PCT/US2020/027705, Written Opinion dated Jul. 24, 2020", 8 pgs.

"U.S. Appl. No. 16/845,870, Restriction Requirement dated Sep. 9, 2021", 7 pgs.

"Chinese Application Serial No. 201780021798.X, Office Action dated Oct. 29, 2019", with English translation of claims, 13 pgs.

"European Application Serial No. 17743534.4, Response filed Dec. 20, 2019 to Extended European Search Report dated May 24, 2019", 8 pgs.

"Chinese Application Serial No. 202110837427.7, Response filed Oct. 13, 2021", with machine translation, 180 pgs.

"Chinese Application Serial No. 201780021798.X, Response filed Apr. 9, 2021 to Office Action dated Feb. 10, 2021", with English claims, 14 pgs.

"Japanese Application Serial No. 2018-539080, Response filed Apr. 22, 2021 to Notification of Reasons for Refusal dated Jan. 22, 2021", with English claims, 10 pgs.

"U.S. Appl. No. 16/845,870, Non Final Office Action dated Dec. 8, 2021", 10 pgs.

"U.S. Appl. No. 15/418,511, Corrected Notice of Allowability dated Aug. 21, 2019", 3 pgs.

"U.S. Appl. No. 15/418,511, Non Final Office Action dated Mar. 8, 2019", 12 pgs.

"U.S. Appl. No. 15/418,511, Notice of Allowance dated May 30, 2019", 8 pgs.

"U.S. Appl. No. 15/418,511, Preliminary Amendment filed Mar. 7, 2017", 11 pgs.

"U.S. Appl. No. 15/418,511, Response filed Jan. 9, 2019 to Restriction Requirement dated Nov. 8, 2018", 11 pgs.

"U.S. Appl. No. 15/418,511, Response filed May 6, 2019 to Non Final Office Action dated Mar. 8, 2019", 9 pgs.

"U.S. Appl. No. 15/418,511, Restriction Requirement dated Nov. 8, 2018", 5 pgs.

"European Application Serial No. 17743534.4, Extended European Search Report dated May 24, 2019", 8 pgs.

"International Application Serial No. PCT/CA2017/050097, International Preliminary Report on Patentability dated Aug. 9, 2018", 9 pgs.

"International Application Serial No. PCT/CA2017/050097, International Search Report dated Jun. 12, 2017", 5 pgs.

"International Application Serial No. PCT/CA2017/050097, Written Opinion dated Jun. 12, 2017", 7 pgs.

"Chinese Application Serial No. 201780021798.X, Office Action dated Jul. 16, 2020", with English translation of claims, 14 pgs.

"Chinese Application Serial No. 201780021798.X, Response filed Mar. 12, 2020 to Office Action dated Oct. 29, 2019", w/English Claims, 15 pgs.

"Chinese Application Serial No. 201780021798.X, Office Action dated Feb. 10, 2021", with machine translation, 14 pgs.

"Japanese Application Serial No. 2018-539080, Notification of Reasons for Refusal dated Jan. 22, 2021", w/ English translation, 13 pgs.

"U.S. Appl. No. 16/845,870, Final Office Action dated Mar. 29, 2022", 12 pgs.

"U.S. Appl. No. 16/845,870, Response filed Mar. 4, 2022 to Non Final Office Action dated Dec. 8, 2021", 15 pgs.

"Chinese Application Serial No. 202110837427.7, Voluntary Amendment filed Feb. 18, 2022", w/ English Claims, 20 pgs.

\* cited by examiner

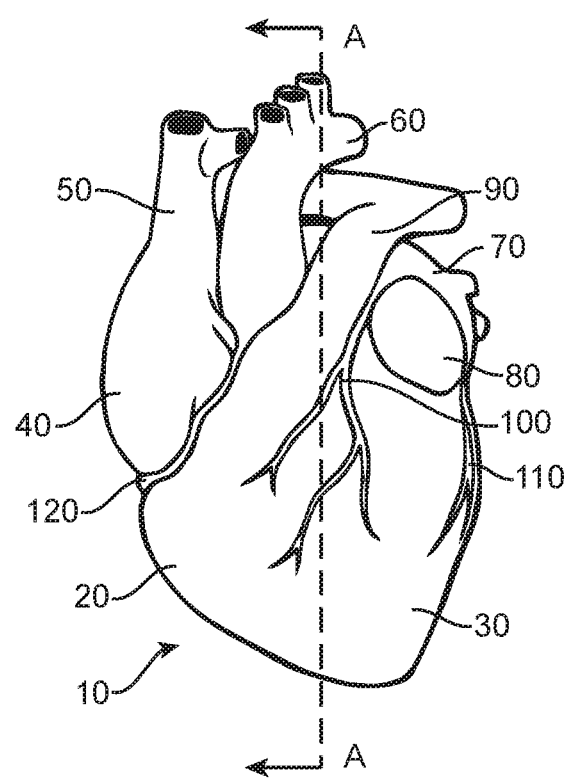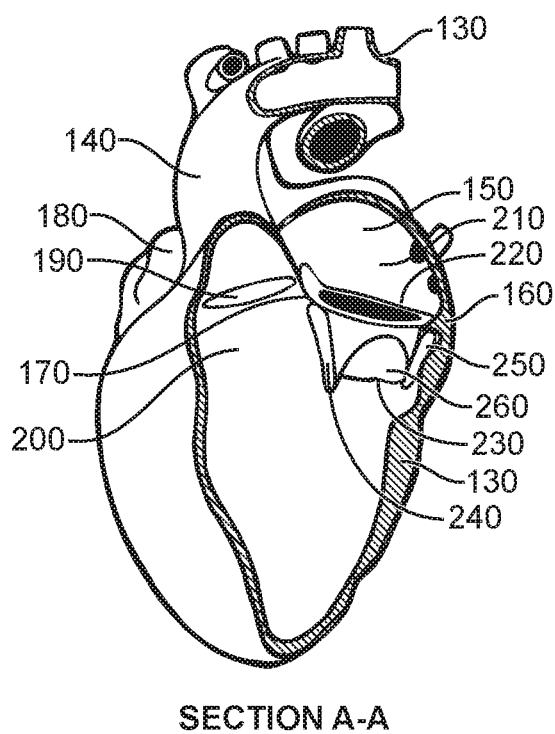
FIG. 1
FIG. 2

SECTION B-B

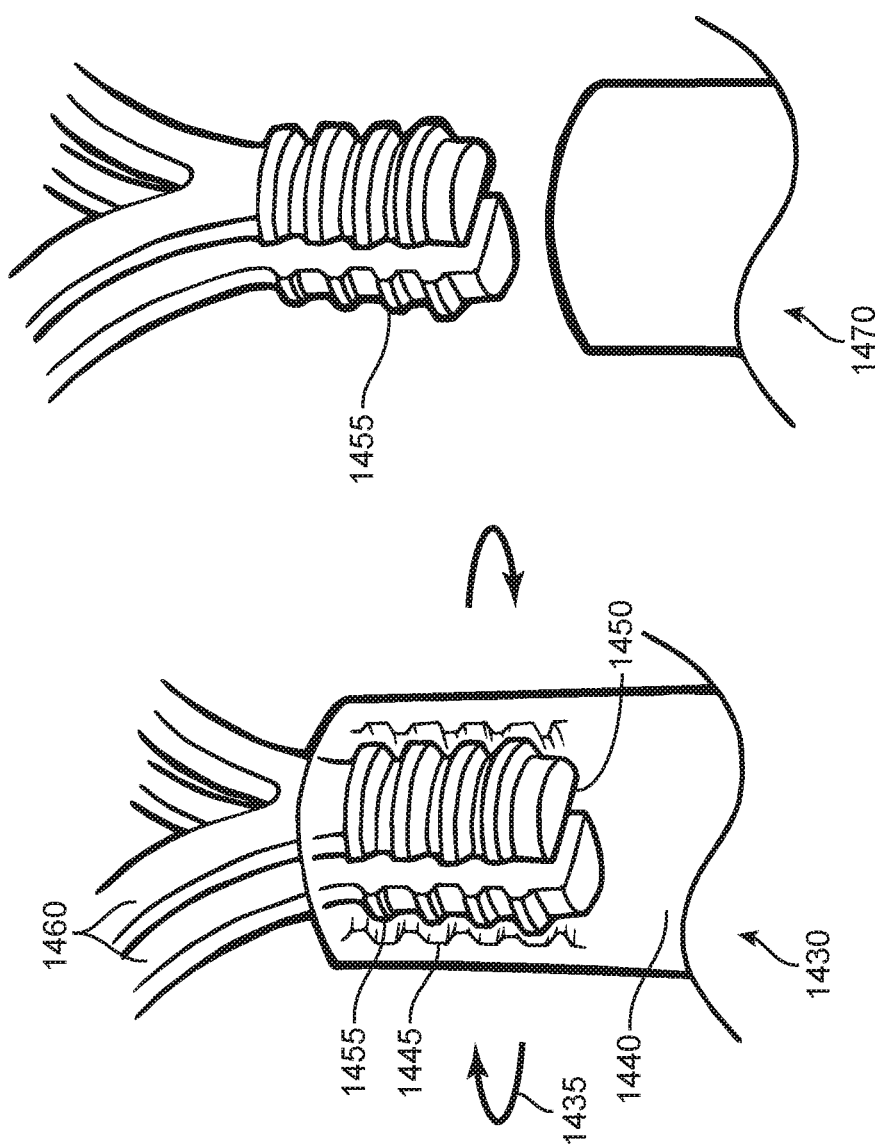

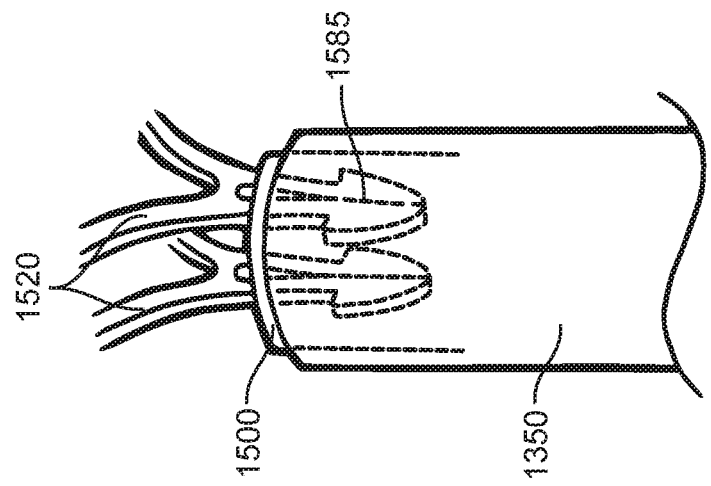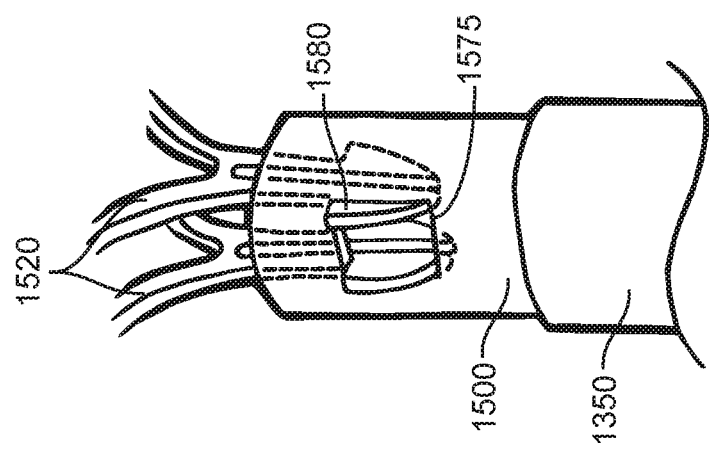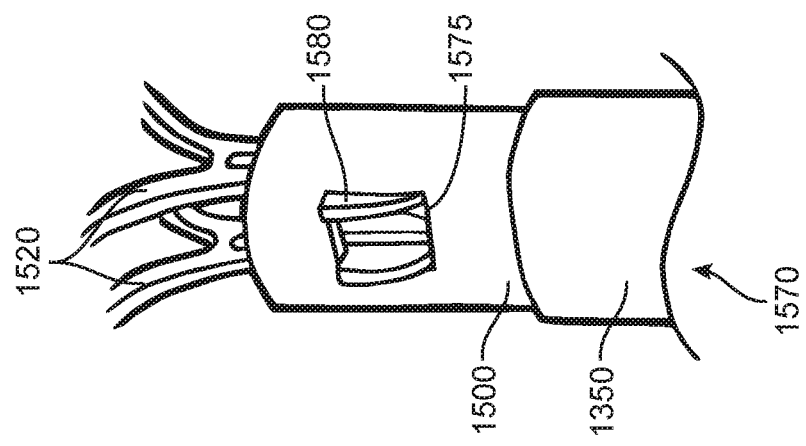

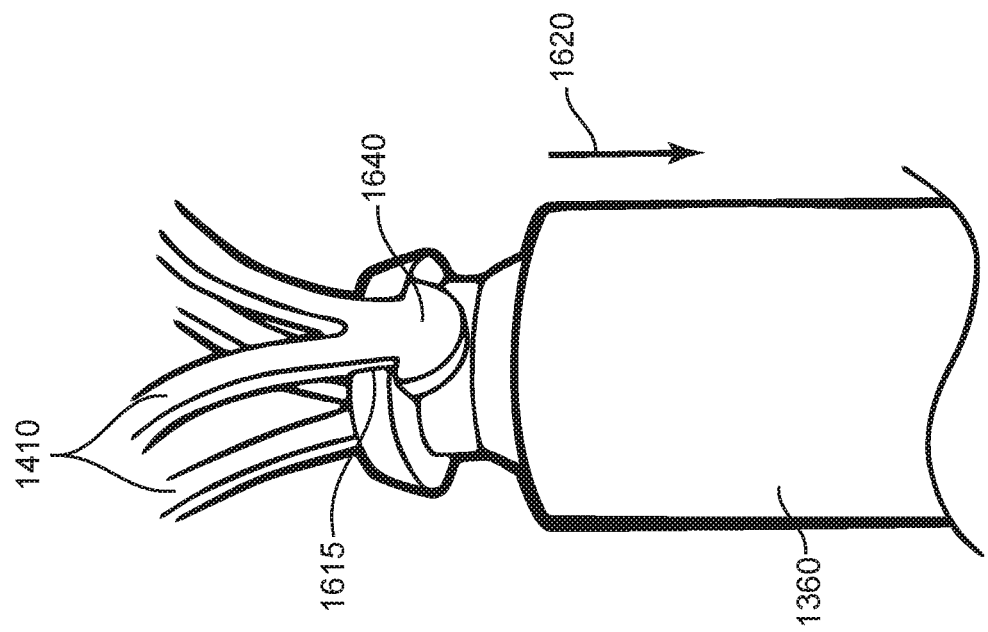
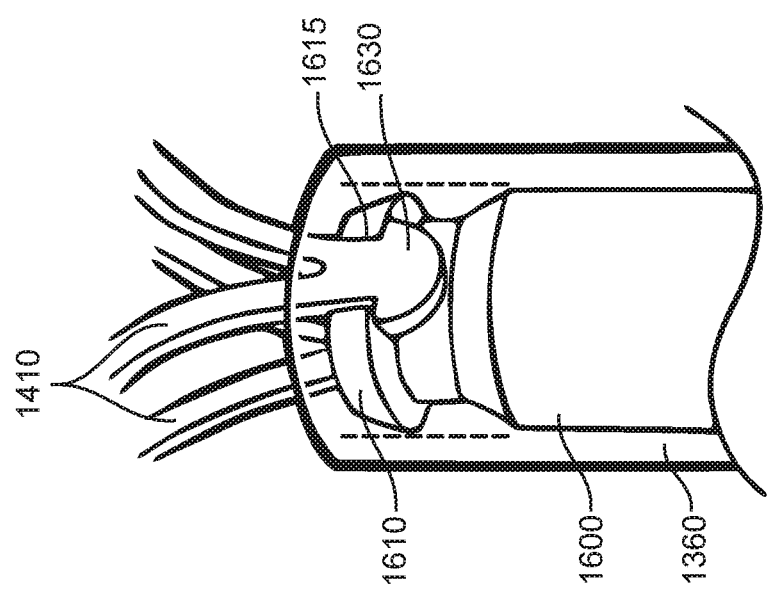

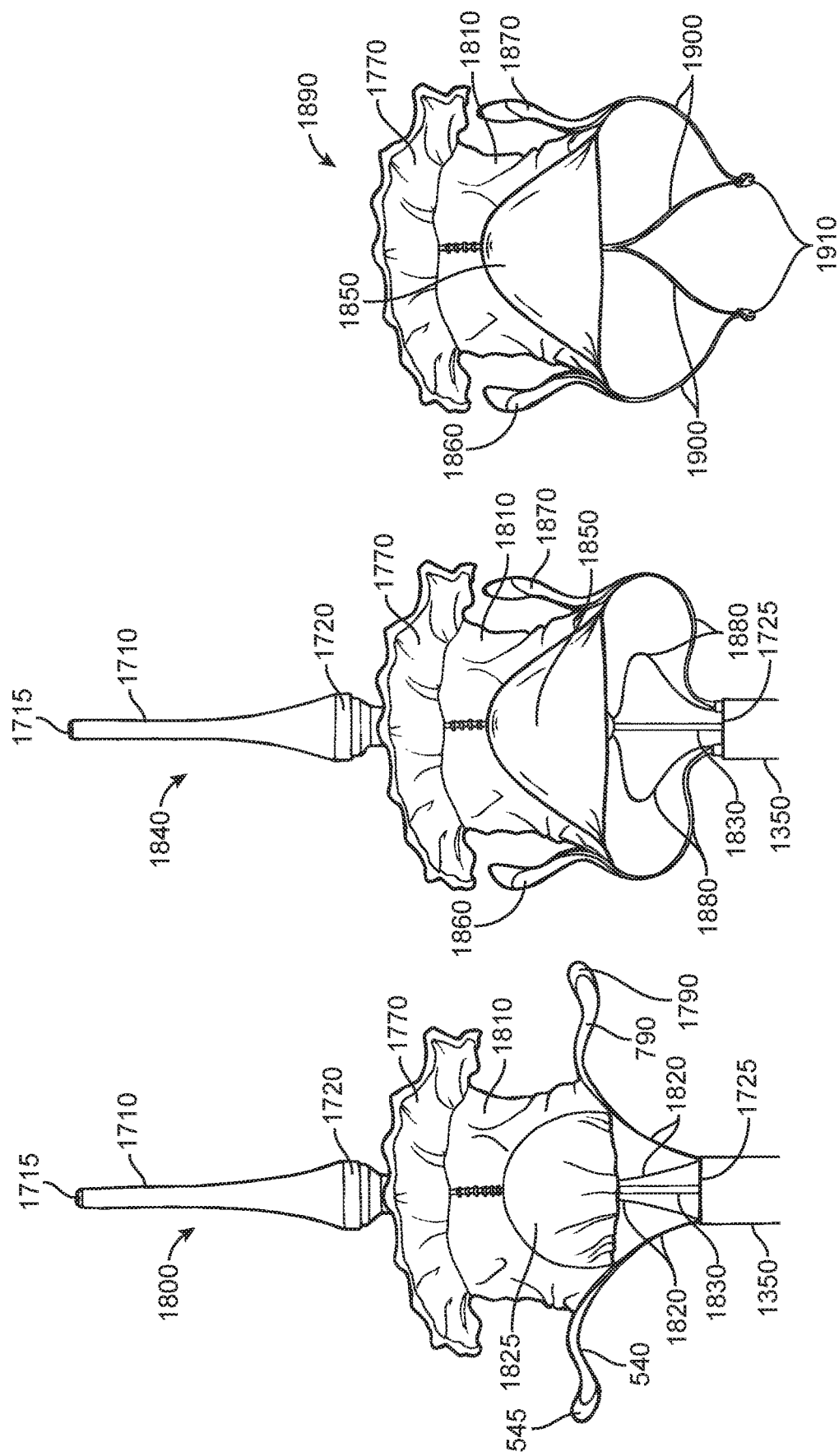

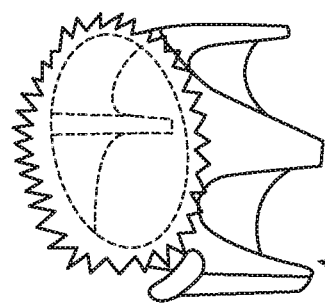
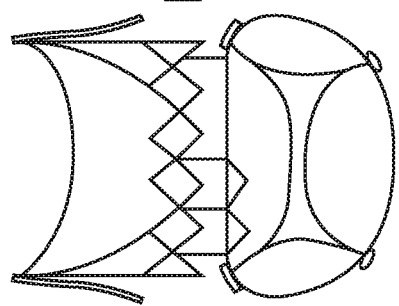
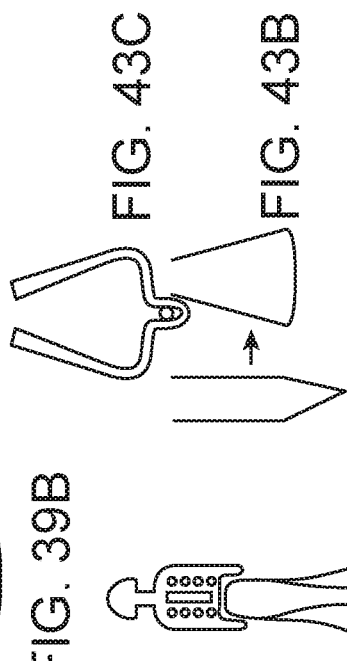
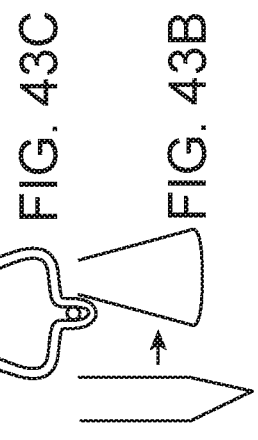
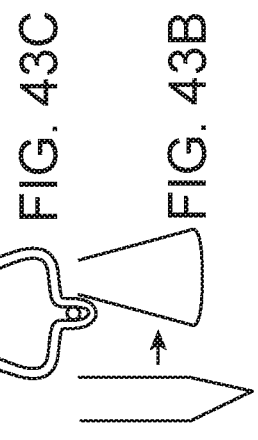
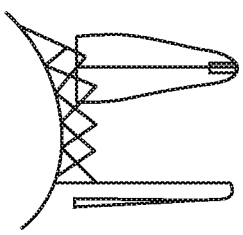
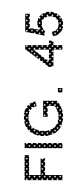
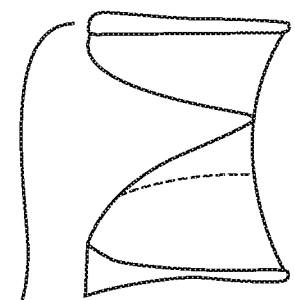
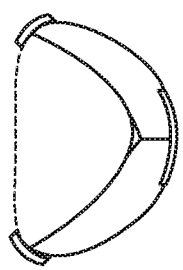
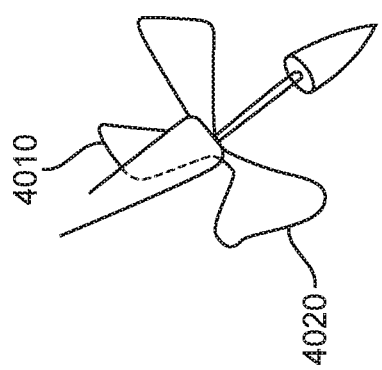

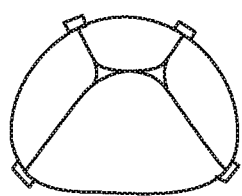
FIG. 46
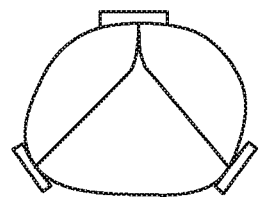
FIG. 47
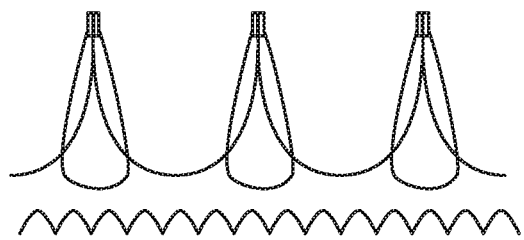
FIG. 48
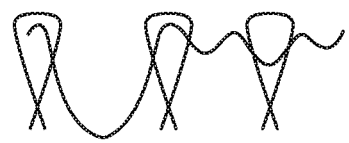
FIG. 49
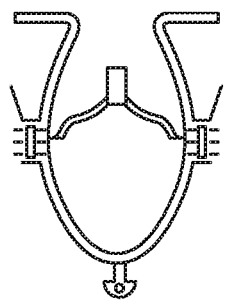
FIG. 50
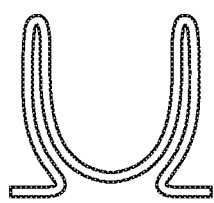
FIG. 51
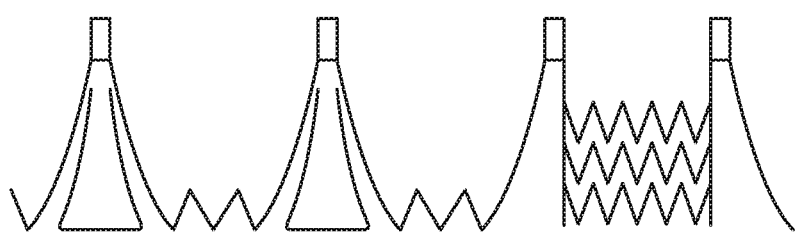
FIG. 52

PROSTHETIC VALVE FOR AVOIDING OBSTRUCTION OF OUTFLOW

CROSS-REFERENCE

The present application is a continuation of U.S. patent application Ser. No. 15/418,511, filed Jan. 27, 2017, which application claims priority to U.S. Provisional Patent Application No. 62/288,987, filed Jan. 29, 2016.

The present application is related to: U.S. Pat. No. 8,579,964, filed Apr. 28, 2011; US Patent Publication Number 2015/0216655, filed Apr. 13, 2015; United State Patent Publication Number 2015/0257878, filed Apr. 21, 2015; United States Patent Publication Number 2014/0039611, filed Oct. 4, 2013; United States Patent Publication Number 2013/0211508, filed Nov. 16, 2012; United States Patent Publication Number 2014/0052237, filed Feb. 8, 2013; United States Patent Publication Number 2014/0155990, filed May 5, 2013; United States Patent Publication Number 2014/0257467, filed Mar. 3, 2014; and United States Patent Publication Number 2014/0343669, filed Apr. 1, 2014; the entire contents which are incorporated herein by reference in their entireties for all purposes.

BACKGROUND OF THE INVENTION

Mitral regurgitation, also known as mitral insufficiency or mitral incompetence, is a heart condition in which the mitral valve does not close properly. This results in abnormal leakage of blood retrograde from the left ventricle through the mitral valve back upstream into the atrium. Persistent mitral regurgitation can result in congestive heart failure. Traditional surgical repair of the valve generally results in a good clinical outcome but requires open heart surgery and a lengthy and costly hospital stay with an extended recovery period. More recently, minimally invasive procedures have been developed to deliver a prosthetic heart valve percutaneously over a catheter through the patient's vasculature to the heart. Alternatively, a transapical procedure is used to introduce the prosthesis through the chest wall and through the apex of the heart. An exemplary prosthesis includes that described in U.S. Pat. No. 8,579,964, the entire contents of which are incorporated herein by reference in their entirety for all purposes. These prostheses and delivery procedures appear to be promising, but in certain circumstances they may obstruct blood flow, cause blood flow through the prosthesis to be turbulent, or disrupt the natural flow path, thereby potentially resulting in hemodynamic problems. Therefore, it would be desirable to provide improved devices, systems, and methods that avoid obstructing blood outflow and that maintain the natural flow path and natural hemodynamics. At least some of these objectives may be met by the exemplary embodiments described herein.

SUMMARY OF THE INVENTION

The present invention generally relates to medical systems, devices, and methods, and more particularly relates to prosthetic heart valves that may be used to repair a valve such as a mitral valve, a heart valve, or any other valve.

In a first aspect, a prosthetic heart valve for implantation in a native mitral valve of a patient comprises a radially expandable anchor frame having an expanded configuration and a collapsed configuration. The heart valve also comprises a prosthetic valve coupled to the anchor frame. The prosthetic valve comprises a plurality of prosthetic valve leaflets each having a free end and a fixed end, with the fixed end coupled to the anchor frame, and the free ends of the plurality of prosthetic valve leaflets have an open configuration and a closed configuration. In the open configuration, the free ends are disposed away from one another to allow antegrade blood flow therethrough, and in the closed configuration the free ends are disposed adjacent one another to substantially prevent retrograde blood flow therethrough. The prosthetic mitral valve is configured to direct blood flow passing through the prosthetic valve in a non-turbulent manner and circular direction along a posterior wall of the patient's left ventricle towards the apex of the heart and upward along a septal wall until it is ejected out the left ventricular outflow tract during systole.

The blood flow substantially maintains momentum and conserves energy as it flows through the prosthetic mitral valve and left ventricle and out the left ventricular outflow tract. The blood flow is indirectly directed to the apex of the heart or the septal wall.

The plurality of prosthetic valve leaflets may comprise an anterior prosthetic leaflet that is sized to span the entire width of the native anterior leaflet. In systole, the anterior prosthetic leaflet may deflect away from the left ventricular outflow tract to provide a clear unobstructed outflow path for the blood flow.

In another aspect, a prosthetic heart valve for implantation in a native mitral valve of a patient comprises a radially expandable anchor frame having an expanded configuration and a collapsed configuration. The prosthetic heart valve also comprises a prosthetic valve coupled to the anchor frame that comprises a plurality of prosthetic valve leaflets each having a free end and a fixed end. The fixed end is coupled to the anchor frame, and the free ends of the plurality of prosthetic valve leaflets have an open configuration and a closed configuration. In the open configuration the free ends are disposed away from one another to allow antegrade blood flow therethrough, and in the closed configuration the free ends are disposed adjacent one another to substantially prevent retrograde blood flow therethrough. The plurality of prosthetic valve leaflets comprise an anterior prosthetic leaflet sized to span the entire width of the native anterior leaflet. In systole, the anterior prosthetic leaflet deflects away from the left ventricular outflow tract to provide a clear unobstructed outflow path.

The prosthetic heart valve may be configured to direct blood flow through the prosthetic valve in a non-turbulent manner and blood flow is preferably directed in a circular direction along a posterior wall of the patient's left ventricle towards the apex of the heart and upward along a septal wall until it is ejected out the left ventricular outflow tract. The blood flow preferably substantially maintains momentum and conserves energy as it flows through the prosthetic heart valve and left ventricle and out the left ventricular outflow tract.

In any aspect, the anchor frame may comprise an anterior anchoring tab configured to anchor on a fibrous trigone of the native mitral valve or on any tissue anterior of the anterior native leaflet and adjacent thereto. The anchor frame may also comprise a second anterior anchoring tab that is configured to anchor on a second fibrous trigone of the native mitral valve or any tissue anterior of the anterior native leaflet and adjacent thereto. The anchor frame may comprise a D-shaped cross-section having a substantially flat anterior portion and a cylindrically shaped posterior portion. The flat anterior portion prevents impingement of the prosthetic heart valve on the left ventricular outflow tract, and the cylindrically shaped portion engages the posterior portion of the native mitral valve. The anchor frame may also comprise one or more commissure posts, and an anterior anchoring tab. The one or more commissure posts may have a free end and an opposite end coupled to the anchor frame. The plurality of commissure posts may be coupled to the plurality of prosthetic valve leaflets, and the anterior anchoring tab may be configured to anchor on a fibrous trigone of the native mitral valve or on any tissue anterior of the anterior native valve leaflet and adjacent thereto. The anterior anchoring tab and the one or more commissure posts may be nested in one another when the anchor frame is in the collapsed configuration. The anterior anchoring tab may originate from a circumferential position on the anchor frame, and the one or more commissure posts also may originate from the same circumferential position on the anchor frame as the anterior anchoring tab. The anterior anchoring tab may originate from the one or more commissure posts, or the one or more commissure posts may originate from the anchoring tab.

In another aspect, a method of treating a native mitral valve in a patient's heart comprises providing a prosthetic mitral valve, anchoring the prosthetic mitral valve in the native mitral valve, and directing blood flow in a non-turbulent manner. The blood flow is directed through the prosthetic mitral valve in a circular direction along a posterior wall of the patient's left ventricle towards the apex of the heart and upward along a septal wall until it is ejected out the left ventricular outflow tract.

The method may further comprise substantially maintaining momentum of the blood flow and conserving energy as the blood flows through the prosthetic mitral valve and left ventricle and out the left ventricular outflow tract. Directing the blood flow may comprise indirectly directing the blood flow to the apex of the heart or the septal wall. The prosthetic mitral valve may comprise an anterior prosthetic leaflet spanning the width of the native anterior valve leaflet, and the method may further comprise deflecting the anterior prosthetic leaflet away from the left ventricular outflow tract to provide a clear unobstructed outflow path during systole. Anchoring the prosthesis may comprise anchoring an anterior anchoring tab disposed on an anterior portion of the prosthetic valve to a fibrous trigone of the native mitral valve or to tissue anterior of the native anterior valve leaflet and adjacent thereto.

In yet another aspect, a method of treating a native mitral valve in a patient's heart comprises providing a prosthetic mitral valve having an anterior prosthetic leaflet that spans the width of the native anterior valve leaflet, anchoring the prosthetic mitral valve in the native mitral valve, and deflecting the prosthetic anterior leaflet in systole away from the left ventricular outflow tract during systole thereby creating an unobstructed outflow path.

The method may further comprise directing blood flow in a non-turbulent manner through the prosthetic mitral valve and in a circular direction along a posterior wall of the patient's left ventricle towards the apex of the heart and upward along a septal wall until it is ejected out the left ventricular outflow tract. Anchoring the prosthesis may comprise anchoring an anterior anchoring tab disposed on an anterior portion of the prosthetic valve to a fibrous trigone of the native mitral valve or to tissue anterior of the native anterior leaflet and adjacent thereto.

In another aspect, a prosthetic heart valve for implantation in a native mitral valve of a patient comprises a radially expandable anchor frame having an expanded configuration and a collapsed configuration; and a prosthetic valve coupled to the anchor frame. The prosthetic valve comprises a plurality of prosthetic valve leaflets each having a free end and a fixed end. The fixed end is coupled to the anchor frame and the free ends of the plurality of prosthetic valve leaflets have an open configuration and a closed configuration. In the open configuration the free ends are disposed away from one another to allow antegrade blood flow therethrough, and in the closed configuration the free ends are disposed adjacent one another to substantially prevent retrograde blood flow therethrough. The plurality of prosthetic valve leaflets comprise an anterior prosthetic leaflet sized to span the entire width of the native anterior leaflet. In systole, the anterior prosthetic leaflet deflects away from the left ventricular outflow tract to provide a clear unobstructed outflow path.

The anchor frame may comprise an anterior anchoring tab configured to anchor on an anterior portion of the native mitral valve and the anterior portion of the native mitral valve may comprise a fibrous trigone. The anchor frame may comprise a second anterior anchoring tab configured to anchor on a second anterior portion of the native mitral valve. In some embodiments, the anchor frame can comprise a D-shaped cross-section having a substantially flat anterior portion and a cylindrically shaped posterior portion, wherein the flat anterior portion prevents impingement of the prosthetic heart valve on the left ventricular outflow tract, and the cylindrically shaped posterior portion engages a posterior portion of the native mitral valve. In some examples, the anchor frame can comprise one or more commissure posts, and an anterior anchoring tab, the one or more commissure posts having a free end and an opposite end coupled to the anchor frame, the one or more commissure posts coupled to the plurality of prosthetic valve leaflets.

The anterior anchoring tab can be configured to anchor on an anterior portion of the native mitral valve. In some embodiments, the anterior anchoring tab and the one or more commissure posts can be nested in one another when the anchor frame is in the collapsed configuration. The anterior anchoring tab originates from a circumferential position on a circumference of the anchor frame, and wherein the one or more commissure posts also originate from the same circumferential position on the circumference of the anchor frame as the anterior anchoring tab. The anterior anchoring tab can originate from the one or more commissure posts, or the one or more commissure posts can originate from the anterior anchoring tab.

In some examples, the anchor frame can further comprise a plurality of chordal bumper struts originating from the one or more commissure posts. The plurality of chordal bumper struts can be configured to dispose native sub-valvular anatomy away from the LVOT. In some embodiments, the commissure posts can comprise an anchoring element adjacent a free end of the commissure post, the anchoring element configured to engage a delivery system. The anchor frame can further comprise a plurality of wishbone shaped struts originating from the one or more commissure posts. The plurality of wishbone shaped struts can be configured to arcuately span the distance between adjacent commissure posts. Each wishbone shaped strut can be comprised of an anchoring element disposed at an apex of the wishbone shaped strut or adjacent a free end of the wishbone shaped strut. The anchoring element can be configured to engage a delivery catheter. The plurality of wishbone shaped struts can be deformable members and can allow radial compression of the anchor frame upon retraction into the delivery catheter. The anchoring element can comprise a single threaded connector, a plurality of threaded connectors, a buckle connector, or a prong connector.

In another aspect, a prosthetic heart valve for implantation in a native mitral valve of a patient comprises a radially expandable anchor frame, an anterior anchoring tab coupled to the anchor frame, and a prosthetic valve coupled to the anchor frame. The radially expandable anchor frame has an expanded configuration and a collapsed configuration and an upstream end and a downstream end. The radially expandable anchor frame comprises one or more commissure posts having a free end and an opposite end coupled to the anchor frame adjacent the downstream end, and an anterior anchoring tab coupled to the anchor frame adjacent the downstream end. The anterior anchoring tab is configured to anchor on an anterior portion of the native mitral valve. The anterior anchoring tab and the one or more commissure posts are nested in one another when the anchor frame is in the collapsed configuration. The prosthetic valve comprises one or more prosthetic valve leaflets each having a free end and a fixed end, wherein the fixed end is coupled to the anchor frame. The one or more commissure posts are coupled to the one or more prosthetic valve leaflets.

In some embodiments, the free ends of the one or more prosthetic valve leaflets can have an open configuration and a closed configuration. In the open configuration the free ends can be disposed away from one another to allow antegrade blood flow therethrough, and in the closed configuration the free ends can be disposed adjacent one another to substantially prevent retrograde blood flow therethrough. The one or more prosthetic valve leaflets can comprise an anterior prosthetic leaflet sized to span a width of a native anterior valve leaflet between two native fibrous trigones. In systole, the anterior prosthetic leaflet can deflect away from the left ventricular outflow tract to provide a clear unobstructed outflow path. The anterior portion of the native mitral valve can comprise a fibrous trigone.

In some examples, the anchor frame can comprise a second anterior anchoring tab configured to anchor on a second anterior portion of the native mitral valve. Additionally or in the alternative, the anchor frame can comprise a D-shaped cross-section having a substantially flat anterior portion and a cylindrically shaped posterior portion. The flat anterior portion can prevent impingement of the prosthetic heart valve on the left ventricular outflow tract, and the cylindrically shaped portion can engage the posterior portion of the native mitral valve.

The anterior anchoring tab can originate from a circumferential position on a circumference of the anchor frame and the one or more commissure posts can also originate from the same circumferential position on the circumference of the anchor frame as the anterior anchoring tab. In some examples, the anterior anchoring tab can originate from the one or more commissure posts, or the one or more commissure posts can originate from the anterior anchoring tab.

In another aspect, a method of treating a native mitral valve in a patient's heart comprises: providing a prosthetic mitral valve having an anterior prosthetic leaflet that spans a width of a native anterior valve leaflet; anchoring the prosthetic mitral valve in the native mitral valve; and deflecting the prosthetic anterior leaflet in systole away from the left ventricular outflow tract during systole thereby creating an unobstructed outflow path. Anchoring the prosthetic mitral valve in the native mitral valve can comprise anchoring an anterior anchoring tab disposed on an anterior portion of the prosthetic valve to an anterior portion of the native mitral valve. In some examples, the anterior portion of the native mitral valve can comprise a fibrous trigone.

The method can comprise radially expanding the prosthetic mitral valve from a collapsed configuration to an expanded configuration, wherein radially expanding the prosthetic mitral valve can comprise expanding one or more anterior anchoring tabs away from nested positions within one or more commissure posts. The method can comprise radially expanding the prosthetic mitral valve from a collapsed configuration to an expanded configuration, wherein radially expanding can comprise expanding one or more posterior anchoring tabs away from nested positions within one or more commissure posts. In some examples, anchoring the prosthetic mitral valve can comprise actuating an actuator mechanism on a delivery system in a first direction, which can comprise moving a sheath catheter away from the prosthetic mitral valve to remove a constraint thereby allowing the prosthetic mitral valve to expand. The method can further comprise actuating the actuator mechanism in a second direction opposite the first direction, which can comprise moving a sheath catheter toward the prosthetic mitral valve to provide a constraint thereby forcing the prosthetic mitral valve to be compressed. In some examples, actuating the actuator mechanism in the first direction can comprise moving a bell catheter away from an anchoring catheter to remove a constraint thereby allowing a commissure anchor to be released. The commissure anchor can comprise an anchoring element that engages a frame of the prosthetic mitral valve to the delivery system. Actuating the actuator mechanism in the second direction can comprise moving the bell catheter toward the anchoring catheter to provide a constraint that captures or restrains the commissure anchor. Providing the constraint that captures or restrains the commissure anchor can comprise releasably sliding a retaining element over the commissure anchor. Moreover, actuating the actuator mechanism can comprise moving a sheath catheter over the anchoring catheter thereby applying a constraint, which can comprise allowing a commissure anchor to be compressed. The commissure anchor can comprise a flexible anchoring element that can engage the frame of the prosthetic mitral valve to the delivery system.

In another aspect, a method of treating a native mitral valve in a patient's heart comprises: providing a prosthetic mitral valve coupled to a radially expandable anchor frame having an upstream end and a downstream end, expanding the radially expandable anchor frame from a collapsed configuration to an expanded configuration, anchoring the prosthetic mitral valve in the native mitral valve, wherein the anterior anchoring tab anchors on an anterior portion of the native mitral valve, and radially expanding the anterior anchoring tab away from a nested position within the one or more commissure posts. The radially expandable anchor frame comprises one or more commissure posts having a free end and an opposite end coupled to the anchor frame adjacent the downstream end, and an anterior anchoring tab coupled to the anchor frame adjacent the downstream end. The anterior portion of the native mitral valve can comprise a fibrous trigone. In some examples, radially expanding the anchor frame can comprise expanding the one or more commissure posts away from a nested position within the anterior anchoring tab.

The prosthetic mitral valve can comprise an anterior prosthetic leaflet and the method can comprise spanning a width of a native anterior valve leaflet between two native fibrous trigones, deflecting the anterior prosthetic leaflet away from a left ventricular outflow tract, and creating an unobstructed outflow path by the deflection of the anterior prosthetic leaflet.

In another aspect, a delivery system for delivering a prosthesis to a target treatment area comprises: an inner guidewire catheter having a proximal end, a distal end, and a lumen extending therebetween, the lumen sized to slidably receive a guidewire; a flexible dilating tip coupled to the guidewire catheter, the dilating tip having a tapered and flexible self-dilating edge, a sheath catheter slidably disposed over the inner guidewire catheter, the sheath catheter having a proximal end and a distal end; an actuator mechanism operably coupled to the proximal end of the sheath catheter. Actuation of the actuator mechanism in a first direction moves the sheath catheter away from the dilator tip thereby removing a constraint from the prosthesis and allowing the prosthesis to expand. Moreover, actuation of the actuator mechanism in a second direction opposite the first direction moves the sheath catheter into engagement with the dilator tip thereby enclosing the prosthesis therein.

The system can comprise a stationary anchoring catheter fixedly disposed over the guidewire catheter, the anchoring catheter having an anchor element adjacent a distal end of the anchor catheter and configured to engage the prosthesis. In some examples, a bell catheter can be slidably disposed over the anchoring catheter. The bell catheter can have a bell element disposed adjacent a distal end of the bell catheter and the bell element can constrain the prosthesis into engagement with the anchor catheter. The anchoring catheter can have a flexible prong type anchor element adjacent the distal end of the anchor catheter, configured to engage the prosthesis. The sheath catheter can be slidably disposed over the anchoring catheter. In particular, an advancement of the distal end of the sheath catheter can collapse the flexible prong type anchor elements into engagement with the prosthesis.

In some embodiments, a stationary bell catheter can be fixedly disposed over the anchoring catheter. The bell catheter can have a bell element disposed adjacent a distal end of the bell catheter, and the bell element can disengage the prosthesis from the anchor catheter. In some embodiments, the system can comprise a bell catheter rotatably disposed over the guidewire catheter. The bell catheter can have an internally threaded bell element disposed adjacent a distal end of the bell catheter, and the threaded bell element can constrain the prosthesis into engagement. A second actuator mechanism can be operably coupled to a proximal end of the bell catheter. Actuation of the second actuator mechanism in a first direction can couple the prosthesis to the bell catheter, providing a constraint for the prosthesis, and actuation of the second actuator mechanism in a second direction opposite the first direction can de-couple the prosthesis from the bell catheter, removing the constraint from the prosthesis. The system can comprise a rotating torque catheter rotatably disposed over the guidewire catheter. The torque catheter can have a driving gear element adjacent a distal end of the torque catheter and configured to transmit torque. A plurality of rotating thread-connector catheters can be rotatably disposed adjacent the torque catheter. The thread-connector catheters can each have a driven gear element adjacent a distal end of each thread connector catheter, and a threaded socket adjacent to the distal end of each thread connector catheter. The driven gear elements can be sized to enmesh with the driving gear element and receive torque, and the threaded sockets can be configured to constrain the prosthesis into engagement. A second actuator mechanism can be operably coupled to a proximal end of the torque catheter. Actuation of the second actuator mechanism in a first direction can couple the prosthesis to the thread-connector catheters and actuation of the second actuator mechanism in a second direction opposite the first direction can de-couple the prosthesis from the thread-connector catheters.

In any of the aspects, the method may further comprise radially expanding the prosthetic mitral valve from a collapsed configuration to an expanded configuration. Radially expanding the prosthesis may comprise expanding an anterior anchoring tab away from a nested configuration with a commissure post.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts the anatomical heart in an anterior view.

FIG. 2 shows a cross-section of FIG. 1, and the interior anatomy of the heart, including the left ventricular outflow tract (LVOT) and a prosthetic mitral valve.

FIG. 16A shows an embodiment of a delivery system and wishbone shaped strut anchoring variation, with a split-threaded connector, connected.

FIG. 16B shows an embodiment of a delivery system and wishbone shaped strut anchoring variation, with a split-threaded connector, disconnected.

FIG. 18A shows an embodiment of a delivery system and wishbone shaped strut anchoring method, with a flexible buckle connector, connected.

FIG. 18B shows an embodiment of a delivery system and wishbone shaped strut anchoring method, with an internal view of a flexible buckle connector, connected.

FIG. 18C shows an embodiment of a delivery system and wishbone shaped strut anchoring method, with an internal view of a flexible buckle connector, disconnected.

FIG. 19A shows an embodiment of a delivery system and wishbone shaped strut anchoring method, with an internal view of an anchor shaped connector, connected.

FIG. 19B shows an embodiment of a delivery system and wishbone shaped strut anchoring method, with an anchor shaped connector, unconstrained to allow disconnection.

FIG. 20D depicts an embodiment of a delivery system in a substantially opened configuration, with a prosthetic mitral valve loaded and nearly released.

FIG. 20E depicts an embodiment of a delivery system in a fully opened configuration, with a prosthetic mitral valve loaded internally, just prior to final deployment.

FIG. 20F depicts an embodiment of a prosthetic mitral valve, post release.

FIG. 38 illustrates a perspective view of a prosthetic valve.

FIG. 39A illustrates an anterior view of a prosthetic valve.

FIG. 39B illustrates a top view of a prosthetic valve.

FIG. 40 illustrates deployment of a prosthetic valve.

FIG. 41 illustrates a side view of a prosthetic valve.

FIG. 42 illustrates a combined commissure post and anchor tab.

FIGS. 43A-43B illustrate an unexpanded and expanded anchor tab.

FIG. 43C illustrates a flat pattern for an expanded anchor tab.

FIG. 44 shows a D-shaped prosthesis.

FIG. 45 shows a side view of a prosthetic valve.

FIG. 46 shows a top view of a prosthetic valve with four leaflets and four anchors.

FIG. 47 shows a top view of a prosthetic valve with three leaflets and three anchors.

FIG. 48 shows a flat pattern of a prosthetic valve.

FIG. 49 shows native valve leaflets superimposed over anchor tabs.

FIG. 50 shows an inversion of the anchor tab with the commissure post nested within.

FIG. 51 shows an embodiment with two anchors located adjacent the native anterior leaflet and an expansion region void of similar anchors in the posterior portion.

FIG. 52 shows a flat pattern of a prosthetic valve.

DETAILED DESCRIPTION OF THE INVENTION

Figure 4:
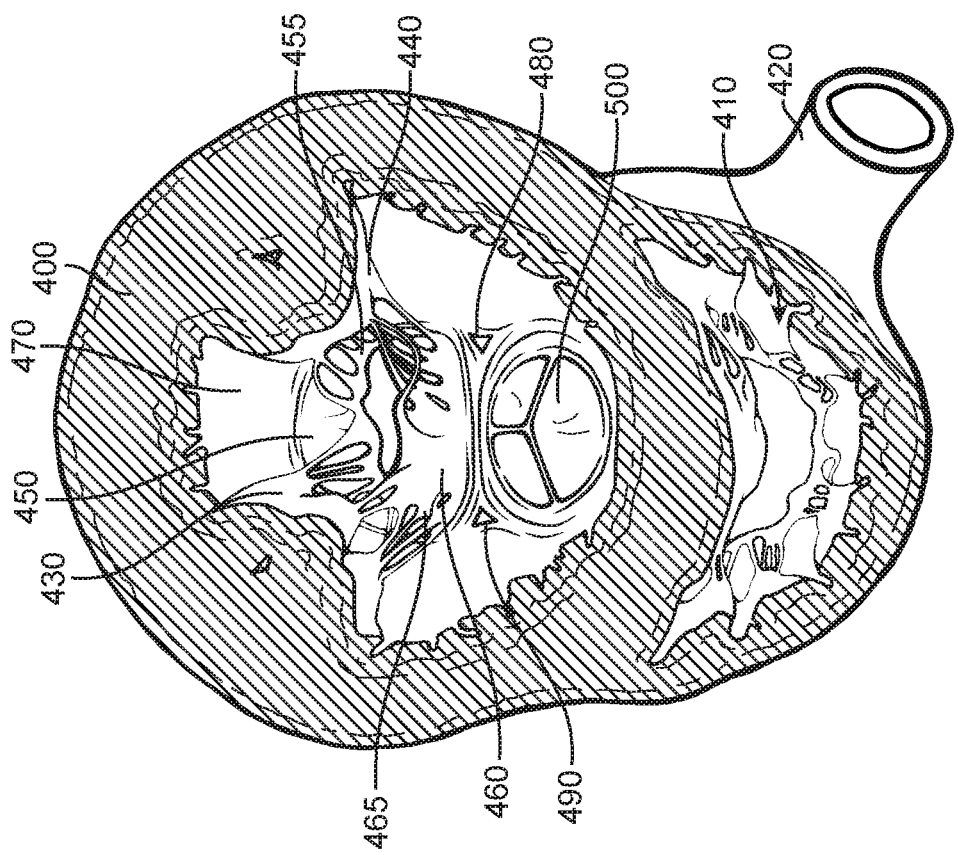
FIG. 4 shows a cross-section of FIG. 3, and the interior anatomy of the heart, particularly, the space inferior to the mitral and aortic valves.

Specific embodiments of the disclosed device, delivery system, and method will now be described with reference to the drawings. Nothing in this detailed description is intended to imply that any particular component, feature, or step is essential to the invention.

As used herein, like numbers refer to like elements.

FIG. 1 provides an illustration of the anatomical heart, herein represented by an anterior aspect 10 of the heart. Anterior views of various structures of the anatomical heart are also presented. The superior vena cava 50, right atrium 40, and right ventricle 20 are shown on the (viewer's) left side of said anterior aspect 10, with superior and inferior structures being separated by the right coronary artery 120. A cross-section line A-A divides the cardiac anatomy into side sections and is further discussed in FIG. 2. Moving to the (viewer's) right side of the heart, an anterior view of the aorta 60 can be seen in a superior position to the pulmonary trunk 90. Beneath the pulmonary trunk 90 are the left atrium 70 and left atrial appendage 80. Beneath and flanking to the (viewer's) left and right of the left atrial appendage 80 are the left anterior descending coronary artery 100 and the intermediate coronary artery 110, respectively. Finally, inferior to all previously mentioned elements is the left ventricle 30.

FIG. 2 shows the internal structures of the heart after sectioning the anterior aspect 10 (as shown in FIG. 1) of the heart along cross-section A-A. The cross-section A-A is bounded by a hatched zone 130 that represents the plane of sectioning. Beginning at the superior-most element, the aorta 140 is depicted in a posterior aspect. Below and behind the aorta 140 is the right atrium 180. An interior view of the left atrium 150 is shown, revealing where a prosthetic mitral valve 210 may be located after implantation. The inflow region 220 of the prosthetic mitral valve 210 and the outflow region 230 of the prosthetic mitral valve can also be seen. An anterior aspect 170 of the prosthetic mitral valve 210 may be adjacent to a zone 190 of the left ventricular outflow tract 200 (LVOT). An anterior anchoring tab 240 may be located in a position that avoids blockage of the LVOT 200. As systole occurs, and blood is shunted towards the LVOT 200 from beneath the prosthetic mitral valve 210, there may be a capacious channel leading directly to the aorta 140, due to the large area of the zone 190. This configuration may leave the LVOT 200 free of obstruction from extraneous prosthesis bulkage or projections.

The prosthetic mitral valve may comprise one or more tabs. The prosthetic mitral valve may comprise 1, 2, 3, 4, 5, 6, 7, 8, 9, 10, or more than 10 tabs. A posterior anchoring tab 250 may be located opposite the anterior anchoring tab 240 of the prosthetic mitral valve 210. The posterior anchoring tab 250 may abut the native anatomy and rest against a posterior ventricular shelf region 160, which is formed within the ventricle at the junction of the ventricle and posterior mitral annulus (see FIG. 4 for a clearer depiction). A third anchoring tab is hidden is the depiction of FIG. 2. A valve leaflet 260, typically constructed from chemically-preserved pericardial tissue harvested from various species such as bovine, porcine, or ovine species, may be located between the anterior anchoring tab 240 and the posterior anchoring tab 250. Further details relating to the prosthetic mitral valve 210 are provided beginning with FIG. 5.

Figure 3:
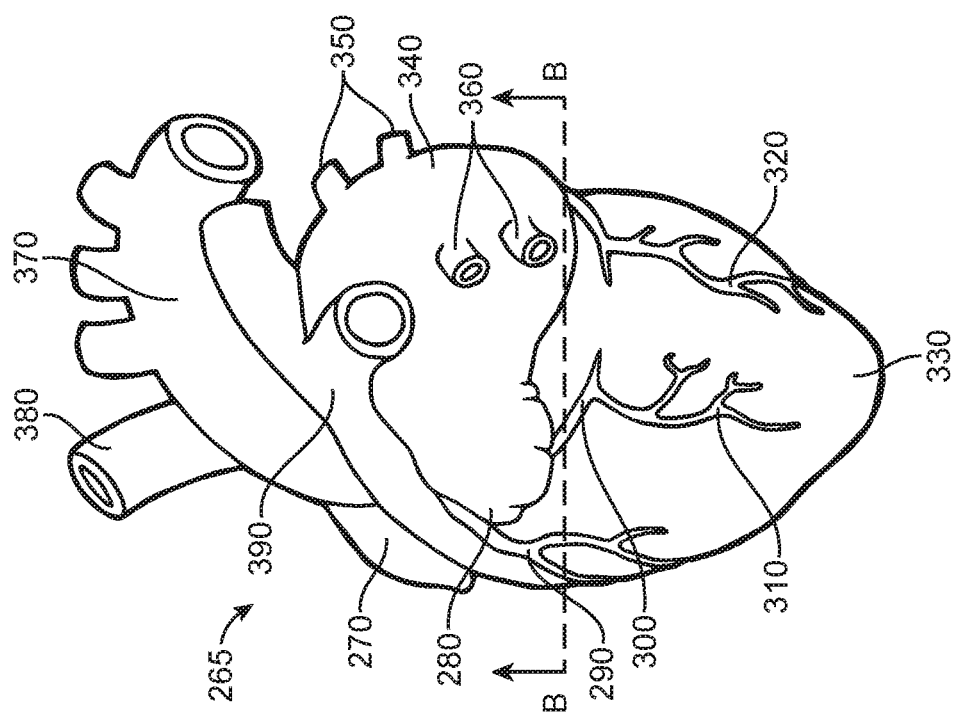
FIG. 3 depicts the anatomical heart in a posterior view.

FIG. 3 provides an illustration of the anatomical heart, herein represented by a posterior aspect 265 of the heart. Posterior views of various structures of the anatomical heart are also presented. Beginning with the most superior elements, a posterior aspect of the superior vena cava 380 is adjacent to a posterior aspect of the aorta 370 and above a posterior aspect of the pulmonary trunk 390. Further depicted posteriorly are the right atrium 270, the left atrial appendage 280 (appearing to the viewer's left), the left atrium 340, the right pulmonary veins 350, and the left pulmonary veins 360 (appearing to the viewer's right). A cross-section line B-B divides the presented cardiac anatomy into superior and inferior sections and is further discussed in FIG. 4. The coronary arteries and relevant branches include the left marginal branch 290, the circumflex branch 300, the posterior left ventricular branch 310 of the left coronary artery, and the posterior interventricular branch 320 of the right coronary artery. Finally, in the most inferior position of the elements is the apex of the heart 330.

FIG. 4 shows the internal structures of the heart after sectioning the posterior aspect 265 (as shown in FIG. 3) of the heart along cross-section B-B. The cross-section B-B is bounded by a hatched zone 400 that represents the plane of sectioning. Beginning at the top of the figure, the posterior ventricular shelf 470 is adjacent to and connected by tissue with the fixed end of the posterior mitral leaflet 450. This shelf may provide a location for a posterior anchoring tab of a prosthetic mitral valve, as described herein. An arcade of posterior chordae tendinae 455 are located adjacent to and connected by tissue with the posterior mitral leaflet 450, finding their insertion points along the free edge of the leaflet. The fixed ends of the chordae 455 find insertion points in both the antero-lateral papillary muscles 430 and postero-medial papillary muscles 440. The papillary muscles 430 and 440 act as muscular support bases for the tethering effect provided by said chordae, spanning the distance between leaflet free edge insertion and papillary muscle insertion while under dynamic tension. Directly opposing the posterior mitral leaflet 450 is an anterior mitral leaflet 460. During systole, the posterior mitral leaflet 450 and the anterior mitral leaflet 460 are brought into communication as their free edges shut against each other, in order to prevent retrograde blood flow into the left atrium. The free edge of the anterior leaflet 460 is also adjacent to and connected by tissue with an arcade of anterior chordae tendinae 465, which also find fixed end insertion points in both the antero-lateral 430 and postero-medial 440 papillary muscles, mirroring the chordal structure of the posterior leaflet.

The fixed end of the anterior leaflet 460 is directly adjacent and connected by tissue with the inflow of the aortic valve 500. This adjacency is commonly known as the aorto-mitral continuity. It is in this region that a risk for outflow tract obstruction presents itself, necessitating the present invention, which aims to minimize LVOT obstruction. Flanking the fixed end of the anterior leaflet 460 are regions of dense cartilaginous tissue known as the fibrous trigones, which act as skeletal-like structures for the heart-at-large. The antero-septal fibrous trigone 480 and the antero-lateral fibrous trigone 490 are represented by triangles, which demarcate landing zones on which the anterior anchoring tabs of the prosthetic mitral valve (not shown)

may abut during valve deployment. For reference, the tricuspid valve 410 and the aorta 420 are shown at the bottom of the figure.

Figure 5:
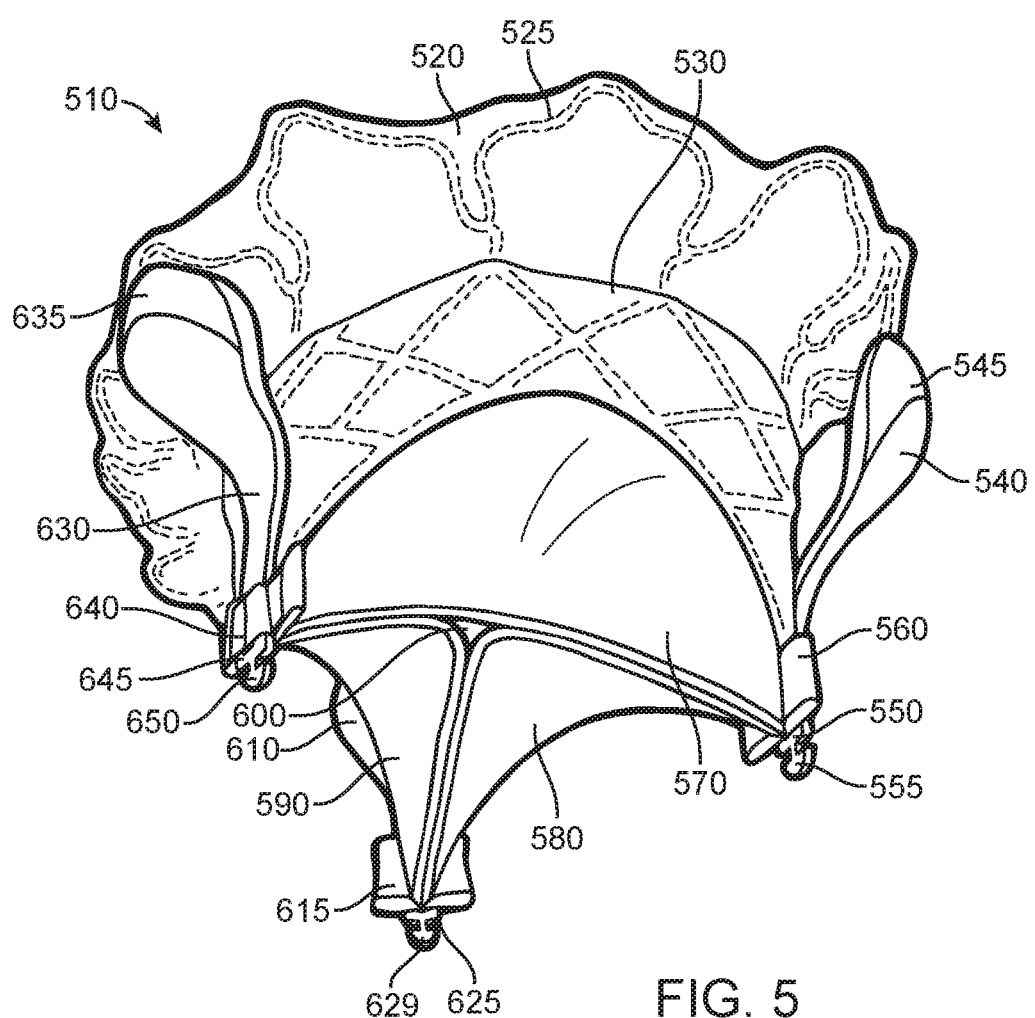
FIG. 5 illustrates an embodiment of a prosthetic mitral valve configured to avoid LVOT obstruction.

FIG. 5 illustrates the present invention in perspective, showing a prosthetic mitral valve 510 (210, as shown in FIG. 2) with a large anterior leaflet. The prosthesis may comprise an atrial region, an annular region, a valvular region, and an anchoring region. A frame 525 may provide the structural means on which the entirety of the prosthetic valve may be erected, and is shown by dashed lines in FIG. 5. The frame may be a nitinol frame. The frame 525 may be layered within various biocompatible fabrics that provide excellent sealing properties. The biocompatible fabrics may comprise polyester, nylon, or any other biocompatible fabric as is known to one having skill in the art. Medical grade suture may used to sew the various fabrics onto the frame 525 to construct the prosthesis. The atrial region of the prosthesis may comprise an atrial skirt 520 which acts as a flange and allows the inflow region of the valve (220, as shown in FIG. 2) to register and seal against the native mitral annulus, upon the floor of the left atrium. The atrial skirt 520 may traverse the entire circumference of the inflow region (220, as shown in FIG. 2) of the prosthetic valve, and may be in communication with and connected to an annular region 530 that also traverses the circumference of the prosthetic valve. In this representation, the anterior surface of the prosthetic valve is shown facing away and to the right, from the viewer. As such, an anterior leaflet 580 is shown facing away and to the right. One or more valve leaflets may form the valvular region of the prosthesis. The leaflets may comprise the anterior leaflet 580, a postero-septal leaflet 570, and a postero-lateral leaflet 590. The anterior leaflet 580 may comprise an anterior leaflet inflow surface, as described herein. The postero-septal leaflet 570 may comprise a postero-septal leaflet inflow surface, as described herein. The postero-lateral leaflet 590 may comprise a postero-lateral leaflet inflow surface, as described herein.

One or more of the plurality of leaflets may comprise chemically-preserved pericardial tissue. The chemically-preserved pericardial tissue may be treated with chemical preservatives that promote polymer cross-linking, render the tissue inert and biocompatible to humans, and/or prepare the tissue for further sterilization treatments. The leaflet tissue may be derived from bovine, porcine, or ovine sources, but shall not be limited to the aforementioned species. In the closed configuration, the free ends of each of the anterior leaflet 580, postero-septal leaflet 570, and postero-lateral leaflet 590 may meet at a triple-point of leaflet coaptation 600. Conversely, the fixed end of each leaflet may be sutured to both the annular region of the valve, and to the next adjacent leaflet at a specific location that provides increased structural resilience, as described herein. Although FIG. 5 shows three leaflets, the prosthetic mitral valve may comprise any number of leaflets. For instance, the prosthetic mitral valve may comprise 1, 2, 3, 4, 5, 6, 7, 8, 9, 10, or more than 10 leaflets.

Each leaflet may be successively joined to the next adjacent leaflet at a commissure attachment point, through a commissure suture pad. Thus, the prosthetic mitral valve may comprise one or more commissure attachment points and one or more commissure suture pads. Specifically, the postero-septal 570 and anterior 580 leaflets may be joined together and attached to an antero-septal commissure attachment point 550 through an antero-septal commissure suture pad 560, the anterior 580 and postero-lateral 590 leaflets may be joined together and attached to an antero-lateral commissure attachment point 625 through an antero-lateral commissure suture pad 615, and the postero-lateral 590 and postero-septal 570 leaflets may be joined together and attached to a posterior commissure attachment point 645 through a posterior commissure suture pad 640. Although FIG. 5 shows three commissure attachment points and three commissure suture pads, the prosthetic mitral valve may comprise any number of commissure attachment points. For instance, the prosthetic mitral valve may comprise 1, 2, 3, 4, 5, 6, 7, 8, 9, 10, or more than 10 commissure attachment points and 1, 2, 3, 4, 5, 6, 7, 8, 9, 10, or more than 10 commissure suture pads.

One or more commissure anchors may extend away from the valve and into free space from each of the commissure attachment points. For instance, an antero-septal commissure anchor 555 may extend from the antero-septal commissure attachment point 560, an antero-lateral commissure anchor 620 may extend from the antero-lateral commissure attachment point 625, and a posterior commissure anchor 650 may extend from the posterior commissure attachment point 645. Each of the commissure anchors may comprise the means through which the prosthesis may be anchored and connected to an appropriate delivery system, as described herein. The shape of each of the plurality of commissure anchors may generally resemble the shape of an anchor or half-moon, but those skilled in the art will recognize that any shapes that allow the plurality of commissure anchors to be anchored effectively to a potential delivery system may be implied by this element. Although FIG. 5 shows three commissure anchors, the prosthetic mitral valve may comprise any number of commissure anchors. For instance, the prosthetic mitral valve may comprise 1, 2, 3, 4, 5, 6, 7, 8, 9, 10, or more than 10 commissure anchors.

Extending away from each of the commissure attachment points, in this instance towards the valve, are one or more of anchoring tabs. Each anchoring tab may comprise a fixed end which is in communication with a commissure attachment point, and a free end which extends towards the atrial skirt and provides an anchoring means through which the prosthetic may attach itself to the native anatomy. Anterior anchoring tabs may generally rest against the native fibrous trigones of the mitral valve, while posterior anchoring tabs may generally rest against the posterior ventricular shelf of the mitral valve. An antero-septal trigonal anchoring tab 540 (240, as shown in FIG. 2) may be connected at a fixed end to the antero-septal commissure anchor point 560, and may have a free end 545 that is brought to rest against the antero-septal fibrous trigone (480, as shown in FIG. 4). An antero-lateral trigonal anchoring tab 610 (260, as shown in FIG. 2) may be connected at a fixed end to the antero-lateral commissure anchor point 625, and may have a free end (not shown in this view) that is brought to rest against the antero-lateral fibrous trigone (490, as shown in FIG. 4). Finally, a posterior anchoring tab 630 (250, as shown in FIG. 2) may be connected at a fixed end to the posterior commissure anchor point 645, and may have a free end 635 that is brought to rest against the posterior shelf (470, as shown in FIG. 4). Although FIG. 5 shows three anchoring tabs, the prosthetic mitral valve may comprise any number of anchoring tabs. For instance, the prosthetic mitral valve may comprise 1, 2, 3, 4, 5, 6, 7, 8, 9, 10, or more than 10 anchoring tabs.

Figure 6:
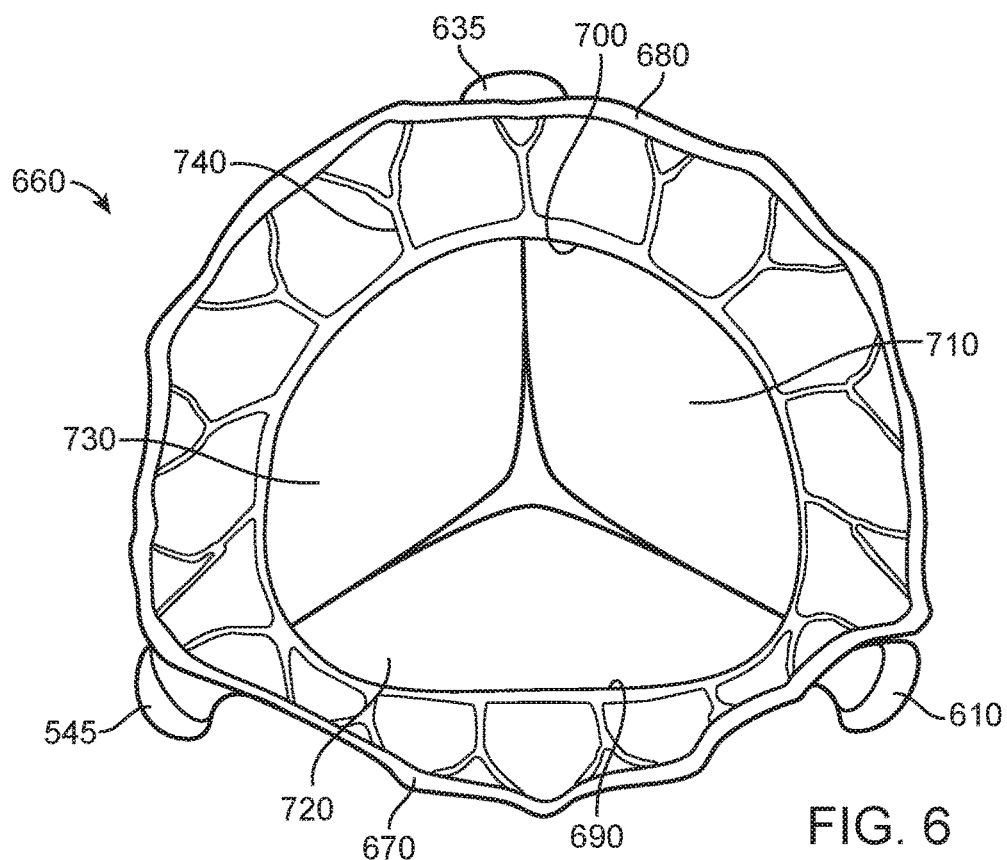
FIG. 6 depicts an inflow view of a tri-leaflet prosthetic mitral valve configured to avoid LVOT obstruction.

FIG. 6 illustrates an inflow view 660 of a prosthetic mitral valve (510, as shown in FIG. 5). The approximate "D" shape of the prosthetic mitral valve may be fully appreciated by tracing a path from the anterior aspect 690 of the valve inflow (flat side of the D shape) in a clockwise direction until the posterior aspect 700 of the valve inflow (curved portion of the D shape) is reached, and then back again to the anterior aspect 690 of the valve inflow. Adjacent the anterior aspect 690 of the valve inflow is the anterior portion 670 of the atrial skirt (520, as shown in FIG. 5). Adjacent the posterior aspect 700 of the valve inflow is the posterior portion 680 of the atrial skirt. A plurality of frame struts 740 may encircle the valve inflow circumferentially. The frame struts 740 may provide structural support and attachment means for both the anterior 670 and posterior 680 portions of the atrial skirt to the annular region of the prosthetic mitral valve (530, as shown in FIG. 5). The postero-lateral leaflet inflow surface 710 (corresponding to the postero-lateral leaflet 590, as shown in FIG. 5), anterior leaflet inflow surface 720 (corresponding to the anterior leaflet 580, as shown in FIG. 5), and postero-septal leaflet inflow surface 730 (corresponding to the postero-septal leaflet 570, as shown in FIG. 5) are also depicted. Also show are the posterior anchoring tab free end 635, antero-lateral trigonal anchoring tab free end 610, and antero-septal trigonal anchoring tab free end 545.

Figure 7:
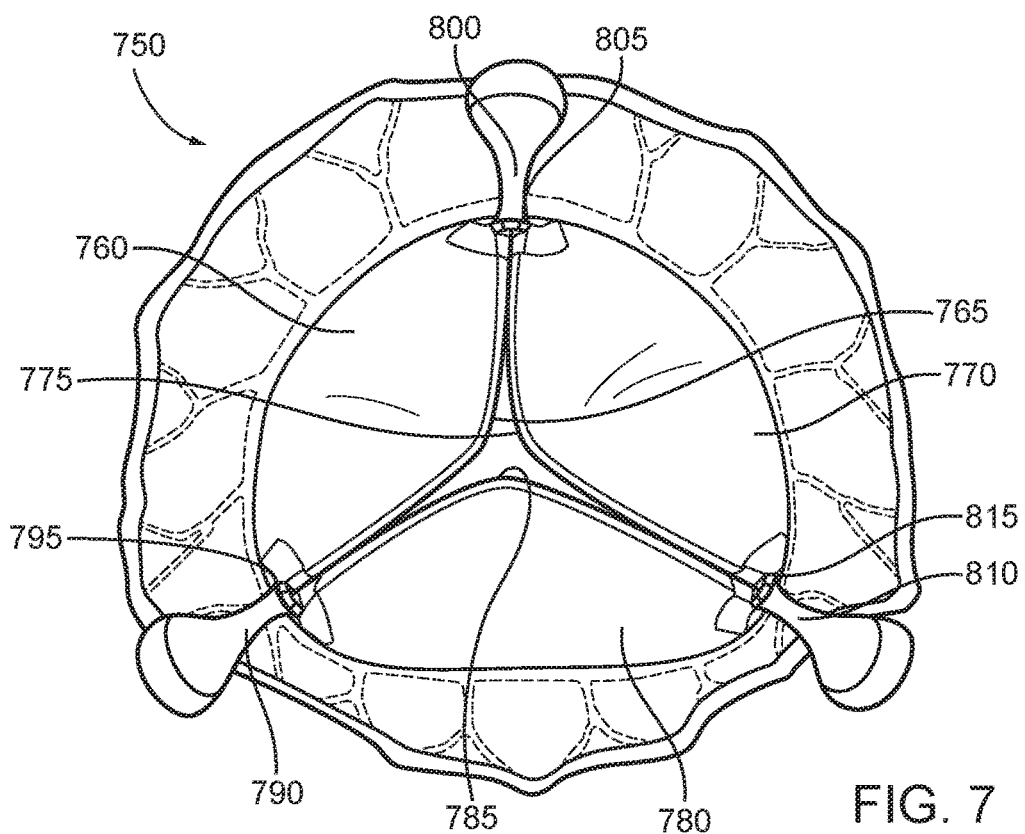
FIG. 7 depicts an outflow view of a tri-leaflet prosthetic mitral valve configured to avoid LVOT obstruction.

FIG. 7 illustrates an outflow view 750 of a prosthetic mitral valve (510, as shown in FIG. 5). The triple-point of leaflet coaptation (600, as shown in FIG. 5) as previously mentioned, may be formed during systole, when a coaptation surface 775 of a postero-septal leaflet 770 (570, as shown in FIG. 5), a coaptation surface 765 of a postero-lateral leaflet 760 (590, as shown in FIG. 5), and a coaptation surface 785 of an anterior leaflet 780 (580, as shown in FIG. 5) are brought into contact with one another through valve closure. The previously described commissures and anchoring tabs are also depicted in this outflow view 750, and are identified by a posterior anchoring tab 800 (630, as shown in FIG. 5) and associated posterior commissure anchor 805 (650, as shown in FIG. 5), an antero-septal trigonal anchoring tab 810 (540, as shown in FIG. 5) and associated antero-septal commissure anchor 815 (555, as shown in FIG. 5), and an antero-lateral trigonal anchoring tab 790 (610, as shown in FIG. 5) and associated antero-lateral commissure anchor 795 (620, as shown in FIG. 5).

Figure 8A:
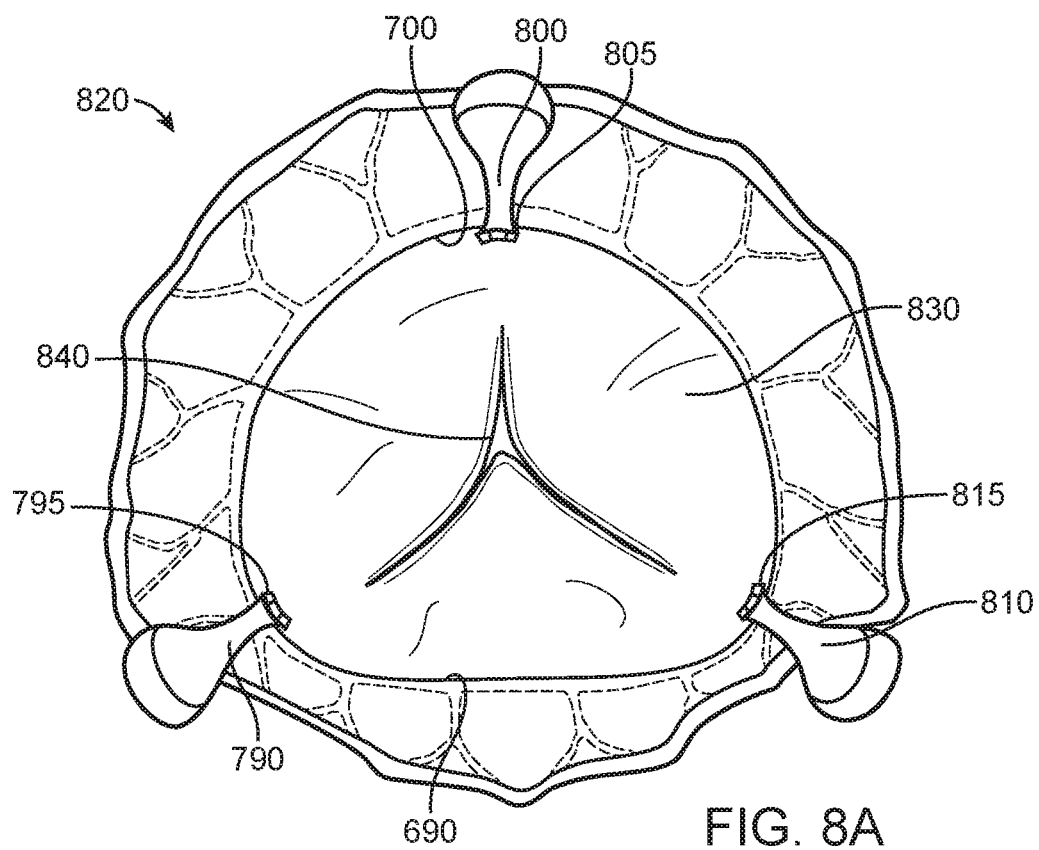
FIG. 8A shows an outflow view of a mono-leaflet prosthetic mitral valve, in the style of a duck-bill valve.

FIG. 8A illustrates an embodiment of a prosthetic mitral valve (510, as shown in FIG. 5) having a single mono-leaflet 830 that is in the style of a duckbill valve, and is presented in an outflow view 820. The duckbill style valve may be created by making an incision 840 at approximately the center of the single mono-leaflet 830, which may create a leaflet coaptation edge on which the resultant valve may function. The prosthetic mitral valve may further comprise one or more of the anterior aspect 690 of the valve inflow, posterior aspect 700 of the valve inflow, the antero-lateral trigonal anchoring tab 790 and associated antero-lateral commissure anchor 795, the posterior anchoring tab 800 and associated posterior commissure anchor 805, or the antero-septal trigonal anchoring tab 810 and associated antero-septal commissure anchor 815.

Figure 8B:
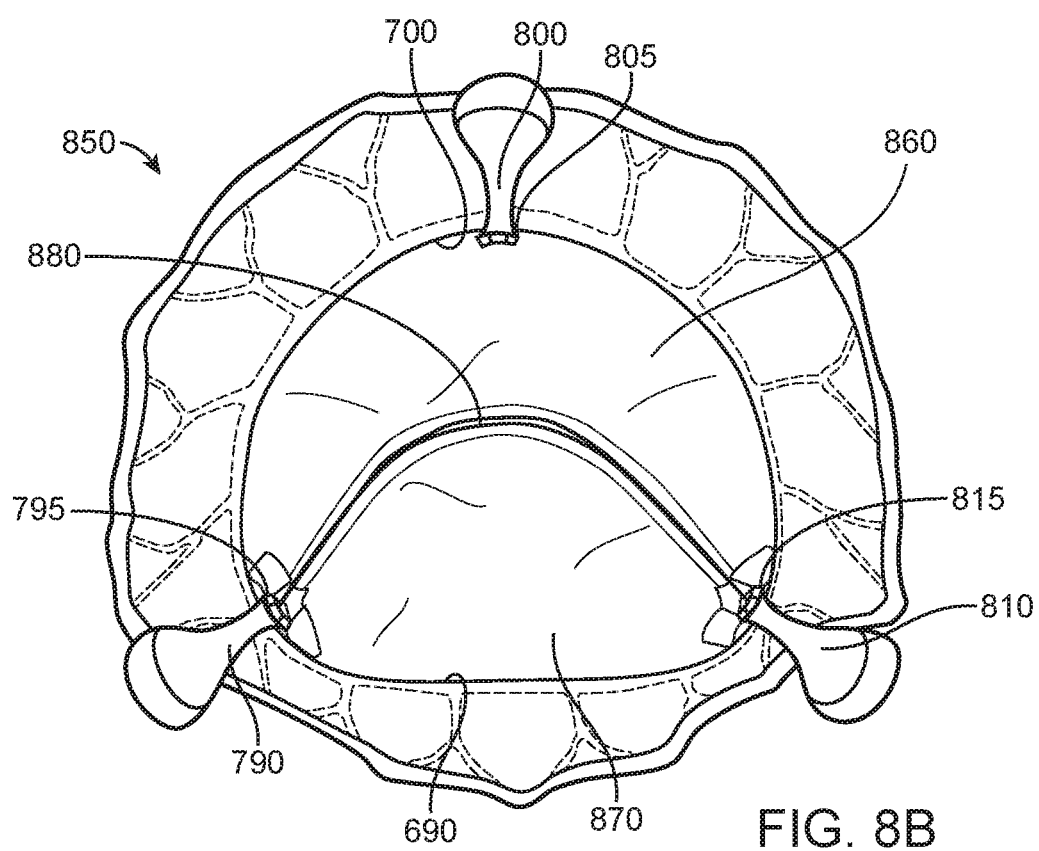
FIG. 8B shows an outflow view of a bi-leaflet prosthetic mitral valve.

FIG. 8B illustrates an embodiment of a prosthetic mitral valve (510, as shown in FIG. 5) comprising a dual or bi-leaflet configuration, again shown in an outflow view 850. The bi-leaflet configuration may be realized by way of a pair of leaflets, comprising an anterior leaflet 870 and a posterior leaflet 860, which may be brought together during systole at a leaflet coaptation edge 880. The prosthetic mitral valve may further comprise one or more of the anterior aspect 690 of the valve inflow, posterior aspect 700 of the valve inflow, the antero-lateral trigonal anchoring tab 790 and associated antero-lateral commissure anchor 795, the posterior anchoring tab 800 and associated posterior commissure anchor 805, and/or the antero-septal trigonal anchoring tab 810 and associated antero-septal commissure anchor 815.

Figure 8C:
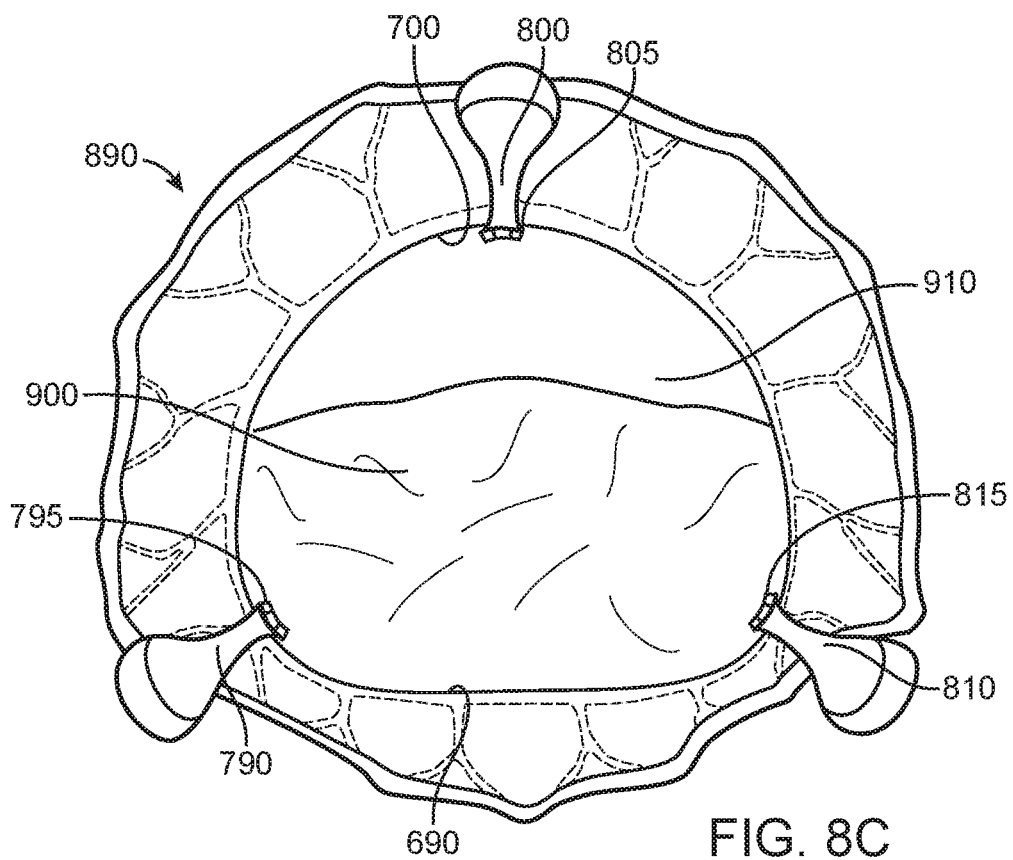
FIG. 8C depicts an outflow view of an anterior mono-leaflet prosthetic mitral valve, in the open position.
Figure 8D:
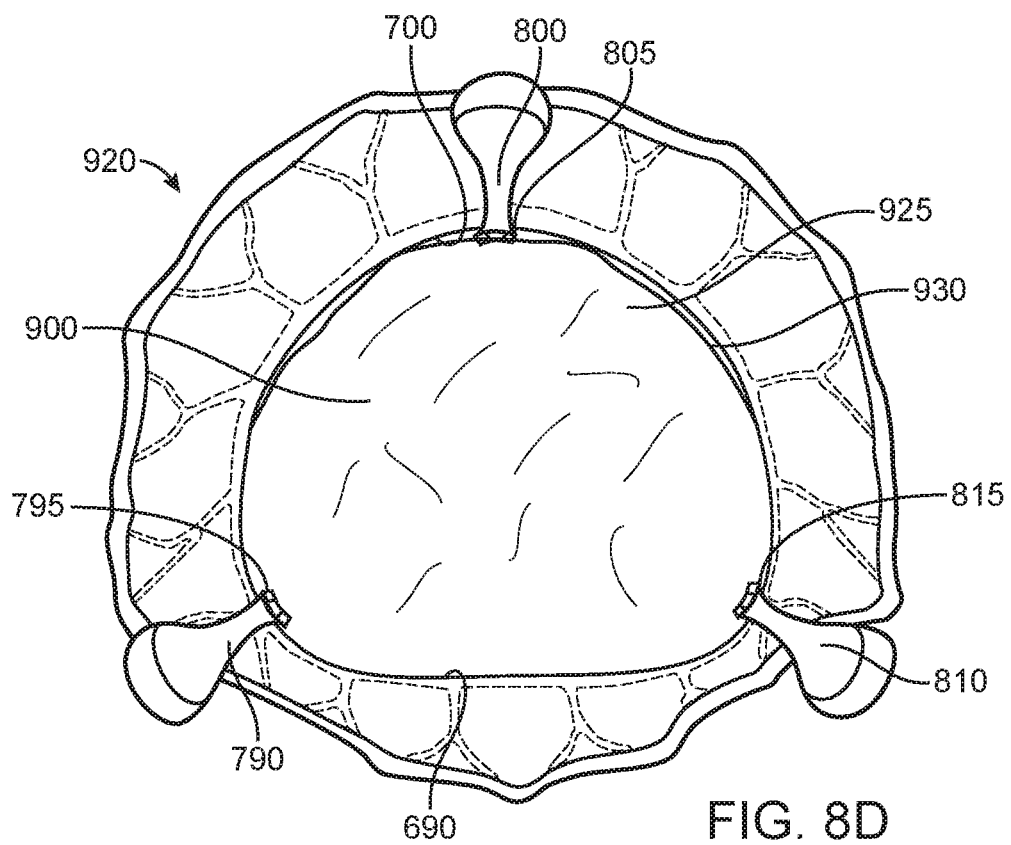
FIG. 8D shows an outflow view of an anterior mono-leaflet prosthetic mitral valve, in the closed position.

FIGS. 8C and 8D show an embodiment of a mono-leaflet prosthetic mitral valve (510, as shown in FIG. 5) seen from the outflow view 890 comprising one large anterior leaflet 900 that may be able to span the entire valve orifice during systole, and seal against the posterior aspect of 700 of the valve inflow. In the open configuration, a posterior outflow region 910 may allow antegrade blood flow through the valve and into the left ventricle, from the left atrium. The prosthetic mitral valve may further comprise one or more of the anterior aspect 690 of the valve inflow, posterior aspect 700 of the valve inflow, the antero-lateral trigonal anchoring tab 790 and associated antero-lateral commissure anchor 795, the posterior anchoring tab 800 and associated posterior commissure anchor 805, or the antero-septal trigonal anchoring tab 810 and associated antero-septal commissure anchor 815.

FIG. 8D shows that in the closed configuration 920, the large anterior leaflet 900 has closed and that a posterior covering region 925 of said anterior leaflet 900 has sealed against a leaflet coaptation edge 930 that appears on the posterior aspect 700 of the valve inflow. The prosthetic mitral valve may further comprise one or more of the anterior aspect 690 of the valve inflow, posterior aspect 700 of the valve inflow, the antero-lateral trigonal anchoring tab 790 and associated antero-lateral commissure anchor 795, the posterior anchoring tab 800 and associated posterior commissure anchor 805, or the antero-septal trigonal anchoring tab 810 and associated antero-septal commissure anchor 815.

Figure 8E:
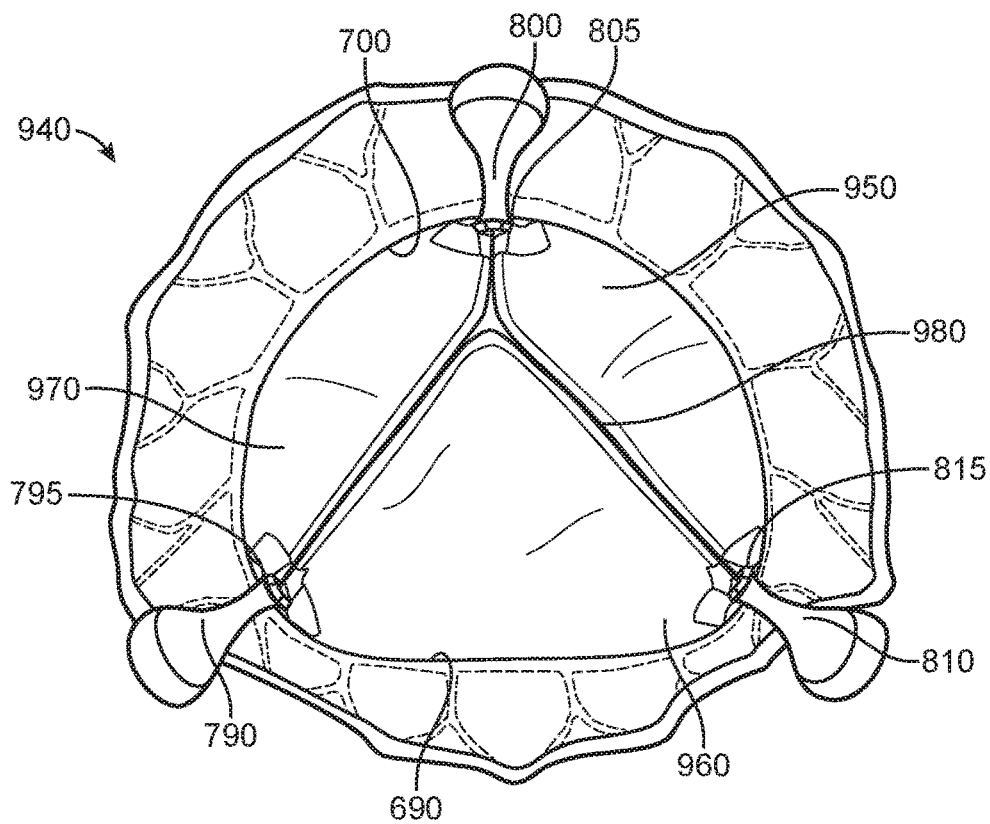
FIG. 8E shows an outflow view of a tri-leaflet prosthetic mitral valve, with a large anterior leaflet.

FIG. 8E illustrates an embodiment of a prosthetic mitral valve (510, as shown in FIG. 5) comprising a tri-leaflet configuration 940, and formed from the plurality of leaflets that are herein described as the large anterior leaflet 960, the small postero-lateral leaflet 970, and the small postero-septal leaflet 950. During systole, said leaflets are forced to close and contact each other along a leaflet coaptation edge 980. The prosthetic mitral valve may further comprise one or more of the anterior aspect 690 of the valve inflow, posterior aspect 700 of the valve inflow, the antero-lateral trigonal anchoring tab 790 and associated antero-lateral commissure anchor 795, the posterior anchoring tab 800 and associated posterior commissure anchor 805, or the antero-septal trigonal anchoring tab 810 and associated antero-septal commissure anchor 815.

Figure 8F:
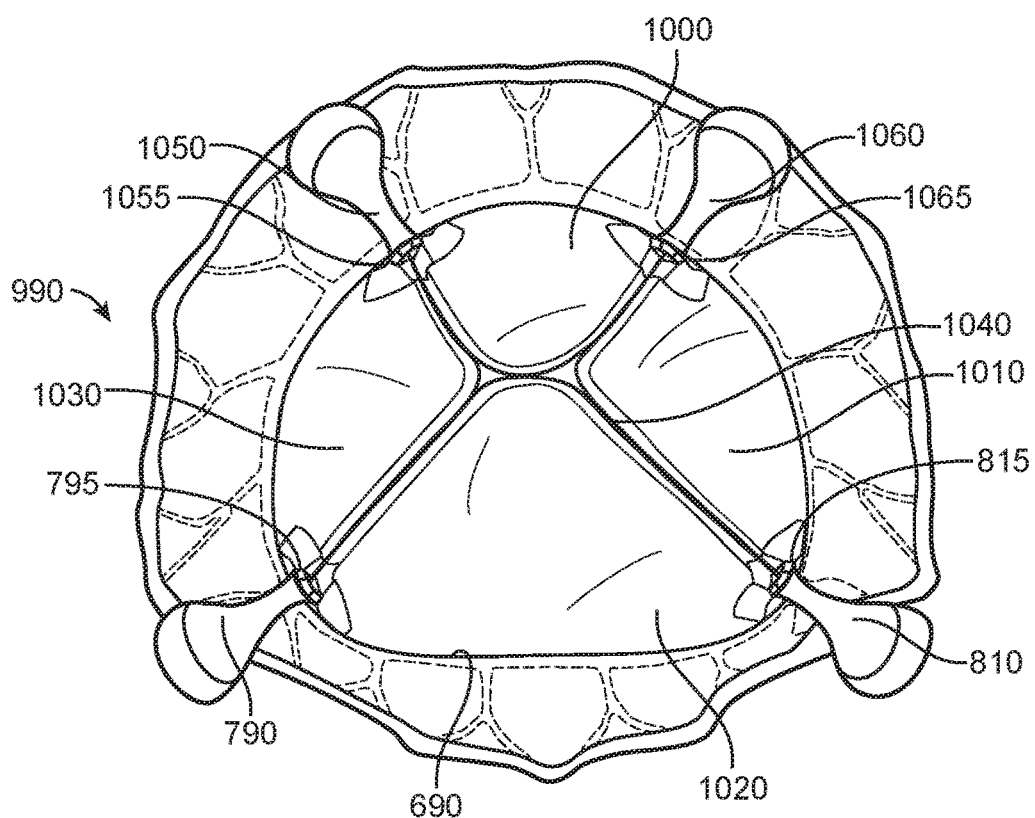
FIG. 8F shows an outflow view of a tetra-leaflet prosthetic mitral valve.

FIG. 8F depicts an embodiment of a prosthetic mitral valve (510, as shown in FIG. 5), seen from the outflow view and comprising a tetra-leaflet configuration 990. The valve may be formed from the plurality of leaflets that are herein described as a posterior leaflet 1000, a septal leaflet 1010, an anterior leaflet 1020, and a lateral leaflet 1030. During systole, the leaflets may be forced to close and contact each other along a leaflet coaptation edge 1040. of the prosthetic mitral valve may comprise one or more anchoring tabs and commissure anchors. Along with the antero-septal 810, and antero-lateral trigonal anchoring tabs and corresponding commissure anchors (815 antero-septal, and 795 antero-lateral), a postero-septal 1060 and a postero-lateral 1050 anchoring tab may be present, as well as the corresponding postero-septal 1065 and postero-lateral 1055 commissure anchors. The prosthetic mitral valve may further comprise one or more of the anterior aspect 690 of the valve inflow, posterior aspect 700 of the valve inflow, the antero-lateral trigonal anchoring tab 790 and associated antero-lateral commissure anchor 795, the posterior anchoring tab 800 and associated posterior commissure anchor 805, or the antero-septal trigonal anchoring tab 810 and associated antero-septal commissure anchor 815.

Figure 9:
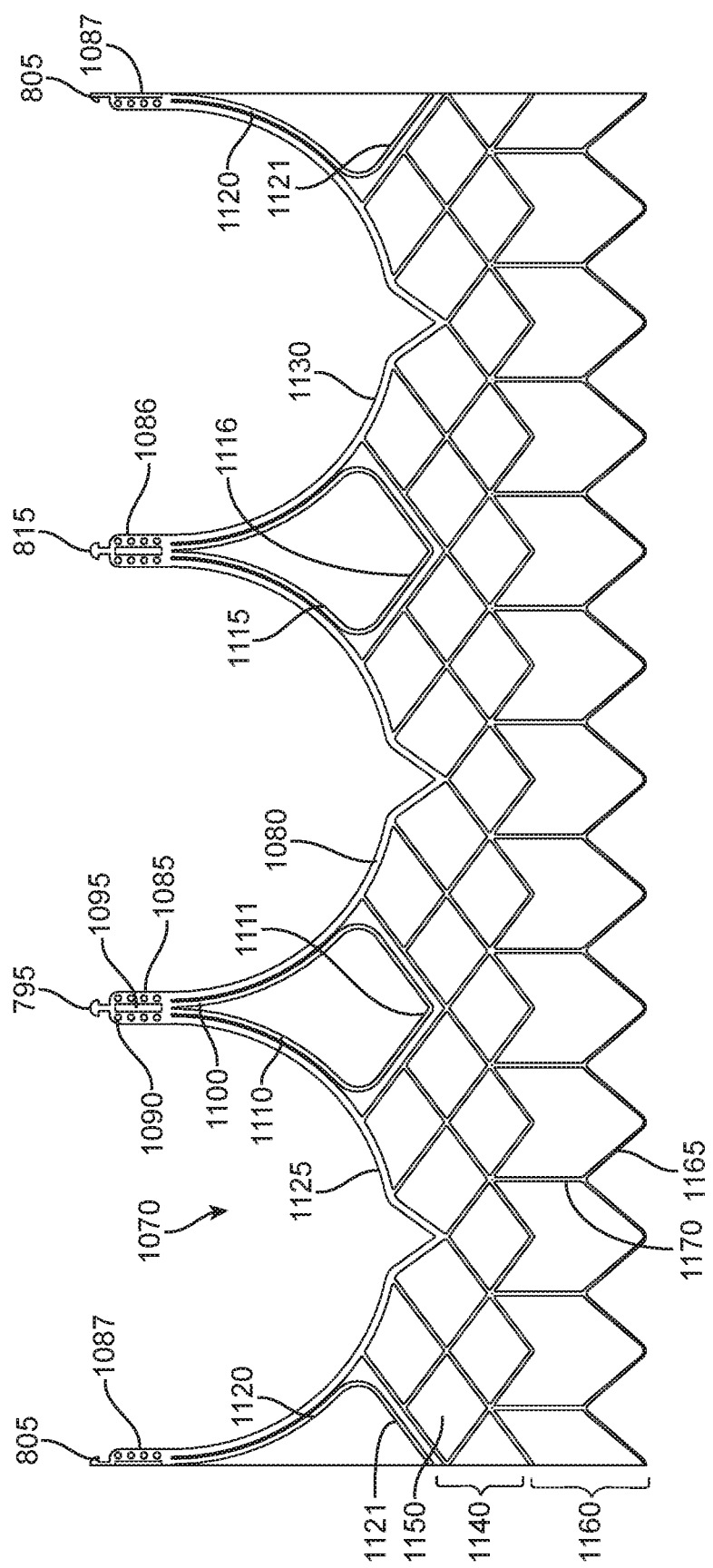
FIG. 9 shows a frame flat-pattern of a prosthetic mitral valve frame.

FIG. 9 depicts a frame flat pattern 1070, which is a representation of a toolpath that a machine-tool (such as a focused laser, router, end mill, or any other machine-tool as is known to one having skill in the art) may follow during the fashioning of a prosthetic valve (510, as shown in FIG. 5). The frame may be cut from a tubular stock of material. For instance, the frame may be cut from a tubular stock of nitinol. The device may include several features discussed previously (introduced in FIG. 5), such as an antero-lateral commissure anchor 795 (element 620 of FIG. 5), an antero-septal commissure anchor 815 (element 555 of FIG. 5), and a posterior commissure anchor 805 (element 650 of FIG. 5). The phrase "strut format" refers to the elements illustrated in a frame flat pattern, whereupon the elements of the frame may be undeformed (i.e., shapeset through metallurgical heat-treatments that are known to those skilled in the art) and generally resemble rectangular members or "struts." Additional details regarding the commissure structures and their spatial relationships with the anchoring tabs are depicted in FIG. 9. This flat pattern represents an embodiment of the prosthetic mitral valve depicted in FIG. 5.

The prosthetic mitral valve may comprise one or more attachment rails, one or more commissures, one or more commissure attachment holes, one or more commissure slots, and one or more commissure junctions. The prosthetic mitral valve may comprise 1, 2, 3, 4, 5, 6, 7, 8, 9, 10, or more than 10 attachment rails, 1, 2, 3, 4, 5, 6, 7, 8, 9, 10, or more than 10 commissures, 1, 2, 3, 4, 5, 6, 7, 8, 9, 10, or more than 10 commissure attachment holes, 1, 2, 3, 4, 5, 6, 7, 8, 9, 10, or more than 10 commissure slots, and 1, 2, 3, 4, 5, 6, 7, 8, 9, 10, or more than 10 commissure junctions.

The antero-lateral commissure anchor 795 may protrude directly from the antero-lateral commissure 1085. The antero-lateral commissure may be the origin and insertion of the antero-lateral anchoring tab 1110 (610, as shown in FIG. 5) via an antero-lateral commissural junction 1100. One or more rows of antero-lateral commissure attachment holes 1090 may be located adjacent to an antero-lateral commissure attachment slot 1095 within the structure of the antero-lateral commissure 1085. The attachment holes 1090 may provide a location for suture that may be used to sew the antero-lateral commissure suture pads (615, as shown in FIG. 5) into place. The antero-lateral commissure suture pads may work in conjunction with the antero-lateral commissure attachment holes to help fasten the valve leaflets of the prosthetic mitral valve to the frame. A free end 1111 of the antero-lateral anchoring tab 1110 is also shown, as are a free end 1116 of the antero-septal anchoring tab 1115 and a free end 1121 of the posterior anchoring tab 1120. A plurality of struts or attachment rails may be used to locate and fasten leaflets onto the frame. Each strut may space a space between successive adjacent commissures. Each strut may have a "u" or arc-shaped form. Specifically, an anterior leaflet attachment rail 1080 may span the space between the antero-lateral commissure 1085 and the antero-septal commissure 1086. The anterior leaflet attachment-rail 1080 may be used to attach the anterior leaflet (not shown) to the frame. A postero-septal leaflet attachment rail 1130 may span the space between the antero-septal commissure 1086 and the posterior commissure 1087. The postero-septal leaflet attachment rail 1130 may be used to attach the postero-septal leaflet (not shown) to the frame. The postero-lateral leaflet attachment rail 1125 may span the space between the posterior commissure 1087 and the antero-lateral commissure 1085. A postero-lateral leaflet attachment rail 1125 may be used to attach the postero-lateral leaflet (not shown). The posterior commissure anchor 805, posterior commissure 1087, posterior anchoring tab 1120, and the free end 1121 of the posterior anchoring tab 1120 are shown on both sides of FIG. 9 to emphasize how the prosthetic mitral valve may be laid out in a frame flat configuration.

Additional structures may support radial compression against the native mitral annulus and/or help to seal the valve inflow against the left atrial floor. A plurality of rows of annular rhomboids 1150 may be located at the annular region 1140 of the frame, traversing the circumference of the frame. A plurality of atrial skirt support struts 1170 may emanate from the annular region 1140 and may act as support beams for a plurality of atrial skirt circumferential struts 1165. The atrial skirt support struts may be substantially parallel to one another and may extend longitudinally. The atrial skirt circumferential struts may be substantially parallel to one another and may be substantially "v-shaped". Each atrial skirt support struts may be connected at top and bottom to atrial skirt circumferential struts. The combination of atrial skirt support struts 1170 and atrial skirt circumferential struts 1165 may form the atrial region 1160 of the valve frame and may provide a location for the atrial skirt to be sutured onto the valve frame.

Figure 10:
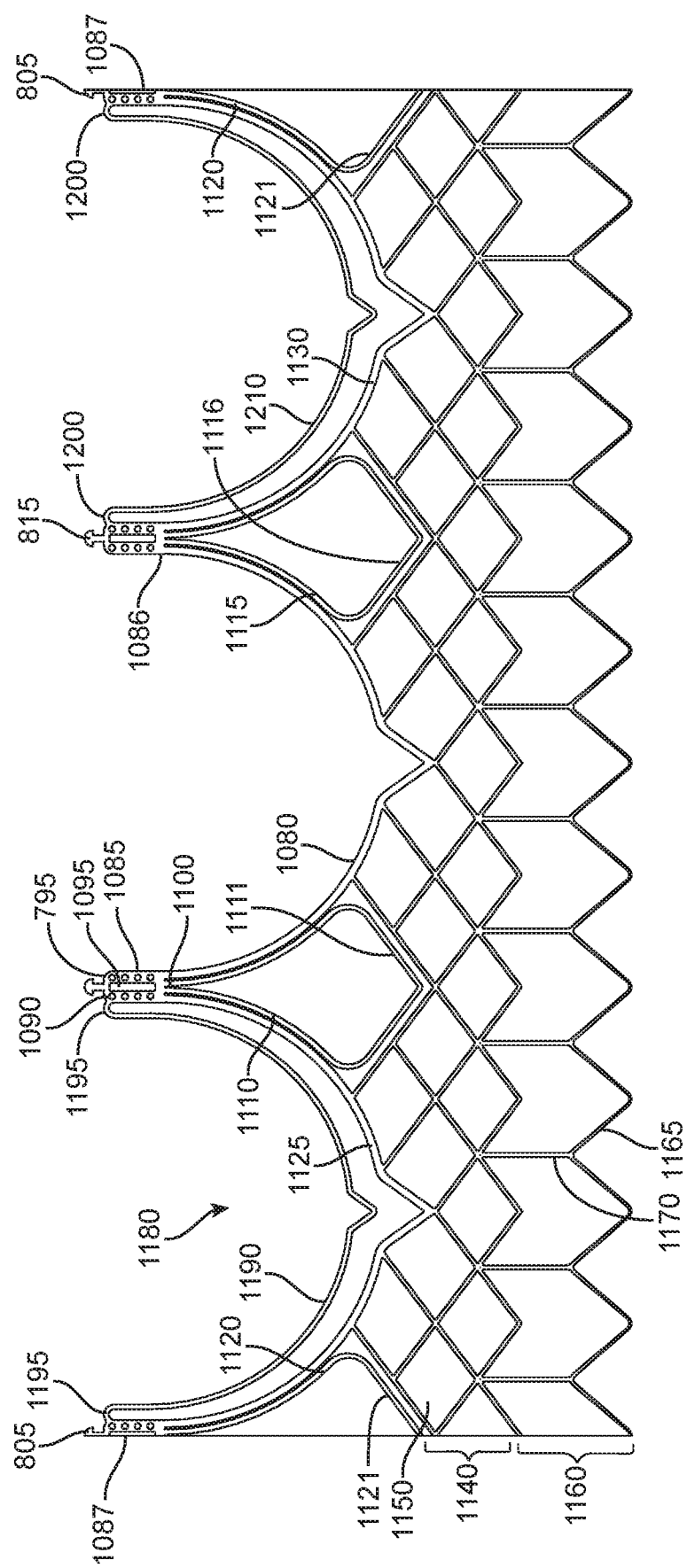
FIG. 10 shows a frame flat-pattern of a prosthetic mitral valve frame, with chordal bumper struts.

FIG. 10 illustrates an embodiment of a frame flat pattern 1180. The frame flat configuration 1180 may comprise any or all of the elements of FIG. 9, with further modifications. The frame flat configuration 1180 may additionally comprise one or more strut features. The configuration may comprise 1, 2, 3, 4, 5, 6, 7, 8, 9, 10, or more than 10 strut features. For instance, one or more strut features may be added, each adjacent to two of the leaflet attachment rails. A postero-lateral chordal bumper strut 1190 may run approximately parallel to the postero-lateral leaflet attachment rail 1125. The postero-lateral chordal bumper strut 1190 may aid in valvular operation by pushing the native chordae away from the prosthetic valve. This may further prevent obstruction in the sub-valvular space and LVOT. The configuration may comprise one or more bumper strut attachment points. The configuration may comprise 1, 2, 3, 4, 5, 6, 7, 8, 9, 10, or more than 10 bumper strut attachment points. One or more postero-lateral chordal bumper strut attachment points 1195 may be located at each end of the postero-lateral chordal bumper strut 1190. Each postero-lateral chordal bumper strut attachment point 1195 may effectively connect an end of the postero-lateral chordal bumper strut 1190 to the adjacent commissure. A postero-septal chordal bumper strut 1210 may run approximately parallel to the postero-septal leaflet attachment rail 1130. One or more postero-septal chordal bumper strut attachment points 1200 may be located at each end of the postero-septal chordal bumper strut 1210. Each postero-septal chordal bumper strut attachment point 1200 may effectively connect and end of the postero-septal chordal bumper strut 1210 to the adjacent commissure. The postero-septal chordal bumper strut 1210 may be functionally equivalent to the postero-lateral chordal bumper strut 1190. The postero-septal choral bumper strut attachment points 1200 may be functionally equivalent to the postero-lateral choral bumper strut attachment points 1195.

Figure 11:
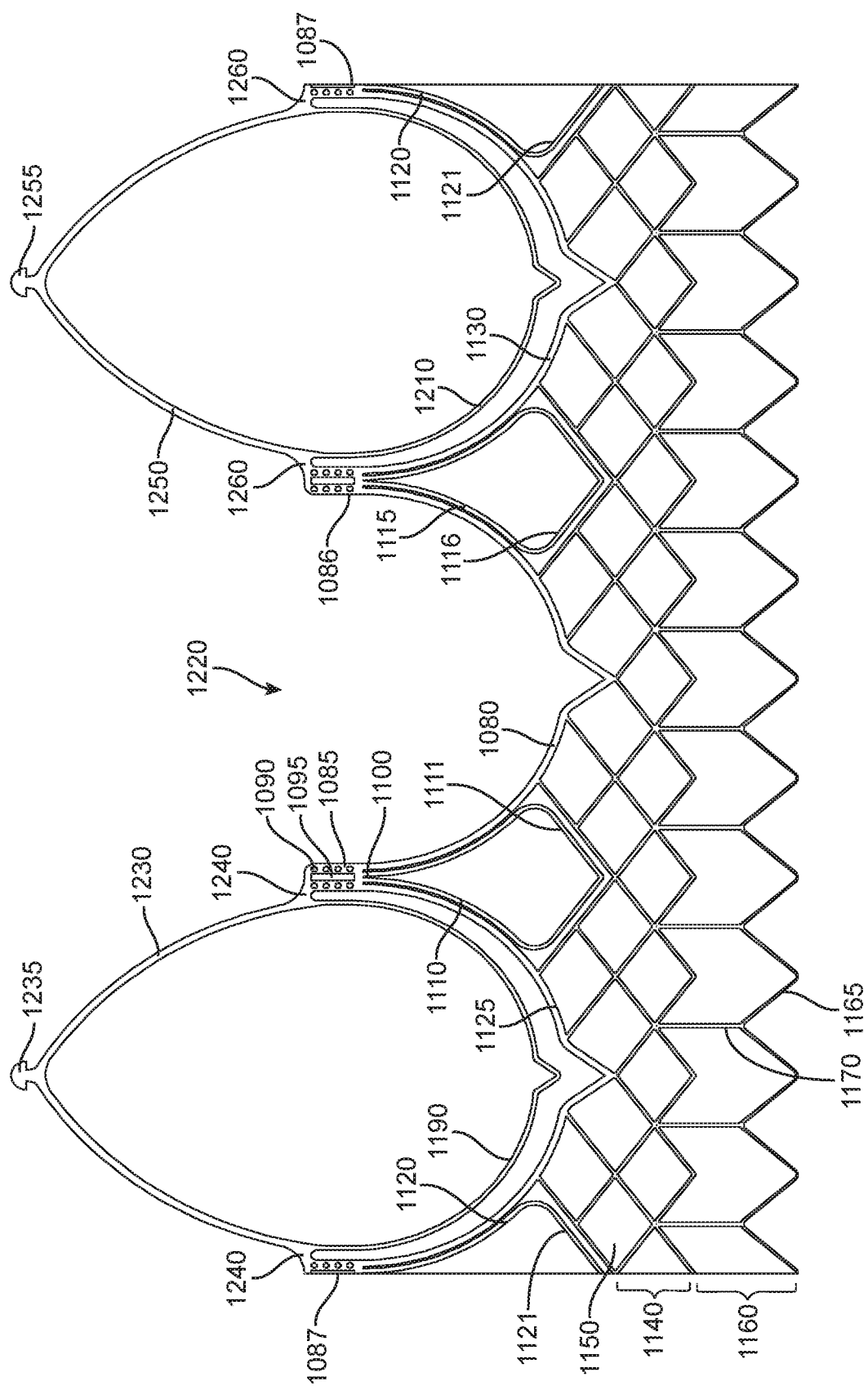
FIG. 11 shows a frame flat-pattern of a prosthetic mitral valve frame, with chordal bumper struts and wishbone shaped struts.
Figure 12:
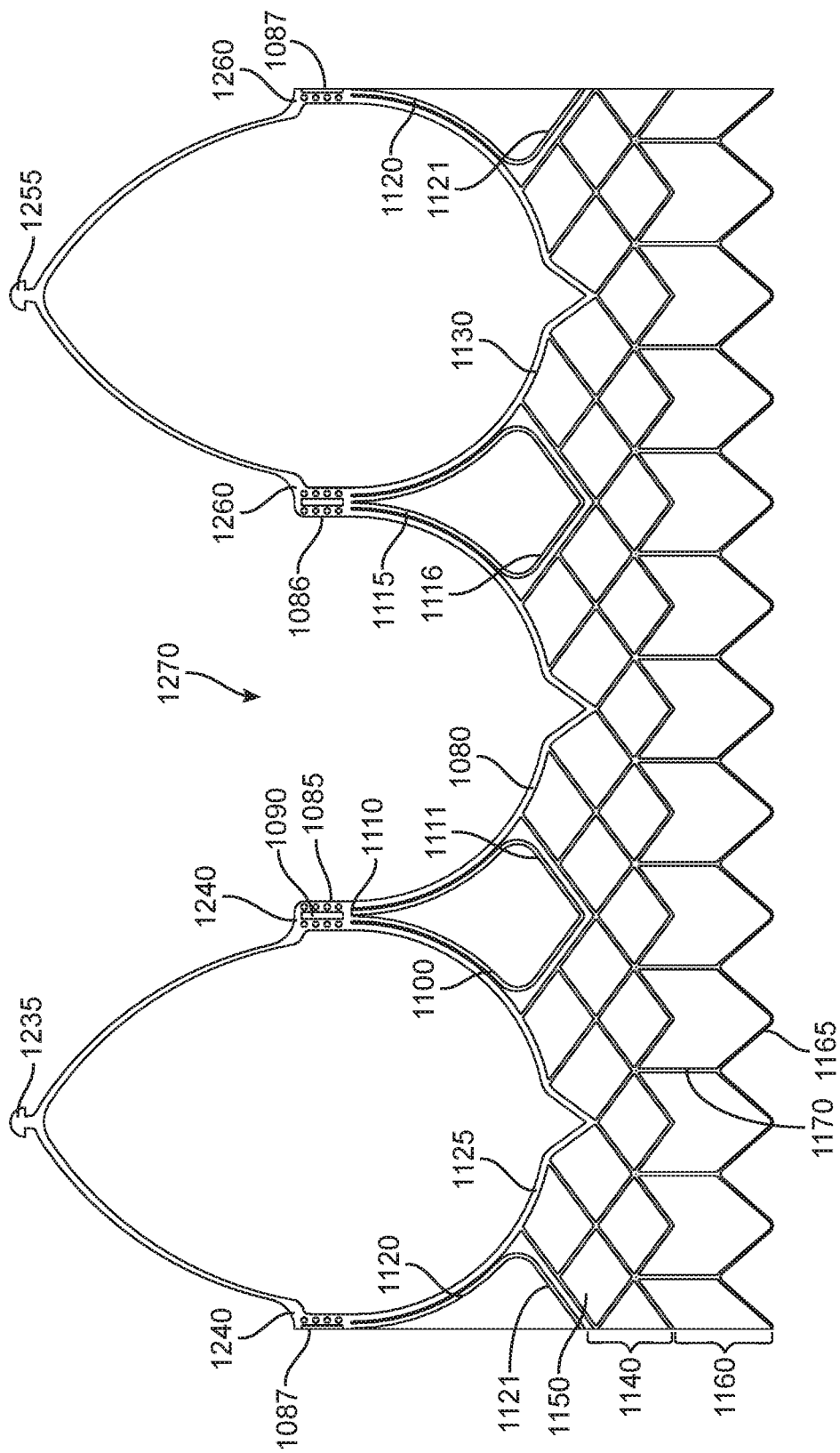
FIG. 12 shows a frame flat-pattern of a prosthetic mitral valve frame, with wishbone shaped struts.

FIG. 11 shows an embodiment of a frame flat pattern 1220. The frame flat configuration 1220 may comprise any or all of the elements of FIG. 10, with further modifications. The frame flat configuration 1220 may further comprise one or more wishbone-shaped members and an absence of the previously described commissure anchors. These alterations may provide an alternative method of anchoring the valve frame to a delivery system, as described herein. The configuration may comprise one or more wishbone struts, one or more wishbone anchors, and one or more wishbone attachment points. The configuration may comprise 1, 2, 3, 4, 5, 6, 7, 8, 9, 10, or more than 10 wishbone struts, 1, 2, 3, 4, 5, 6, 7, 8, 9, 10, or more than 10 wishbone anchors, and 1, 2, 3, 4, 5, 6, 7, 8, 9, 10, or more than 10 wishbone attachment points. A postero-lateral wishbone shaped strut 1230 may emanate from a first strut attachment point 1240 on the antero-lateral commissure 1085. The postero-lateral wishbone shaped strut 1230 may arc upwardly and across the postero-lateral leaflet space until it meets a second strut attachment point 1240 located on the posterior commissure 1087. At the apex of the postero-lateral wishbone shaped strut 1230 may be a postero-lateral wishbone anchor 1235 which may replace the previously depicted antero-lateral and posterior commissure anchors (795 and 805 of FIG. 10, respectively). The postero-lateral wishbone anchor 1235 may be functionally and structurally equivalent to the antero-lateral and posterior commissure anchors. Additionally, a postero-septal wishbone shaped strut 1250 may emanate from a first strut attachment point 1260 on the antero-septal commissure 1086. The postero-septal wishbone shaped strut may arc upwardly and across the postero-septal leaflet space until it meets a second strut attachment point 1260 located on the posterior commissure 1087. At the apex of the postero-septal wishbone shaped strut 1250 may be a postero-septal wishbone anchor 1255 which may replace the previously depicted antero-septal and posterior commissure anchors (815 and 805 of FIG. 10, respectively). The postero-septal wishbone anchor may be functionally and structurally equivalent to the antero-septal and posterior commissure anchors. The wishbone shaped struts may allow the prosthetic mitral valve to be forced into an easily compressible configuration for delivery with a catheter, as described herein. This may result in a more easily retractable and/or repositionable prosthesis. wishbone shaped strut FIG. 12 shows yet an embodiment of a frame flat pattern 1270. The frame flat configuration 1220 may comprise any or all of the elements of FIG. 11, with further modification. The frame flat configuration 1270 may lack certain elements of FIG. 11. For instance, the postero-lateral chordal bumper struts (1190, as shown in FIG. 11) and/or postero-septal chordal bumper struts (1210, as shown in FIG. 11) may be excluded from the frame flat configuration 1270. Save for the absence of said bumper struts, the frame flat configuration 1270 may be functionally equivalent to the frame flat configuration 1220 of FIG. 11. A perspective view of the prosthetic mitral valve of FIG. 12 can be seen in FIG. 13.

Figure 13:
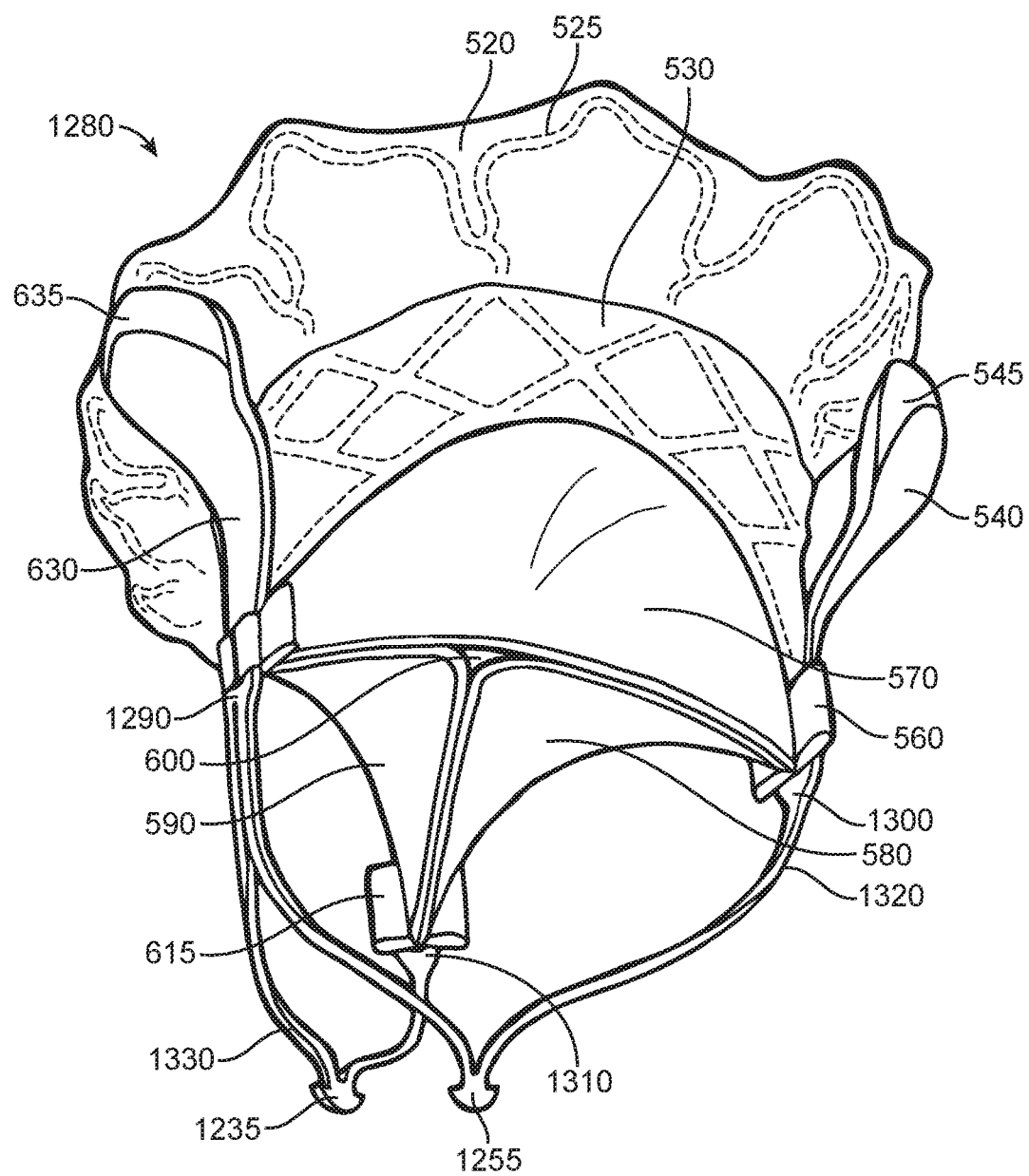
FIG. 13 illustrates an embodiment of a prosthetic mitral valve with wishbone shaped struts, and fashioned to avoid LVOT obstruction.

FIG. 13 shows a perspective view of the prosthetic mitral valve shown as the frame flat configuration 1270 in FIG. 12. Any or all of the features and elements previously described in FIG. 5 may be present in the embodiment of FIG. 13. The embodiment of FIG. 13 may be functionally and structurally equivalent to the embodiment of FIG. 5, save for the addition of one or more wishbone shaped struts and one or more wishbone attachment regions. The embodiment of FIG. 13 may comprise 1, 2, 3, 4, 5, 6, 7, 8, 9, 10, or more than 10 wishbone shaped struts and 1, 2, 3, 4, 5, 6, 7, 8, 9, 10, or more than 10 wishbone attachment regions. 1330. A postero-septal wishbone shaped strut 1320 may find a first insertion with the frame at an antero-septal tab wishbone attachment region 1300, which may be located adjacent to the antero-septal commissure. The postero-septal wishbone shaped strut 1320 may find a second insertion with the frame at a posterior tab wishbone attachment region 1290, which may be located adjacent to the posterior commissure. A postero-septal wishbone anchor 1255 may be located at the apex of the wishbone, allowing for attachment to a delivery system, as described herein. A postero-lateral wishbone shaped strut 1330 may find a first insertion with the frame at an antero-lateral tab wishbone attachment region 1310, which may be located adjacent to the antero-lateral commissure. The postero-lateral wishbone shaped strut 1330 may find a second insertion with the frame at a posterior tab wishbone attachment region 1290, which may be located adjacent to the posterior commissure. A postero-lateral wishbone anchor 1235 may be located at the apex of the wishbone, allowing for attachment to a delivery system, as described herein.

Prior minimally invasive procedures have been developed to deliver a prosthetic heart valve percutaneously over a delivery catheter through the patient's vasculature to the heart, or through the use of a transapical procedure to introduce the prosthesis through the chest wall and through the apex of the heart (330 as shown in FIG. 3). An exemplary prosthesis includes that described in U.S. Pat. No. 8,579,964, the entire contents of which are incorporated herein by reference in their entirety for all purposes. Further embodiments of exemplary delivery catheters and delivery systems are described and illustrated in the following figures.

Figure 14:
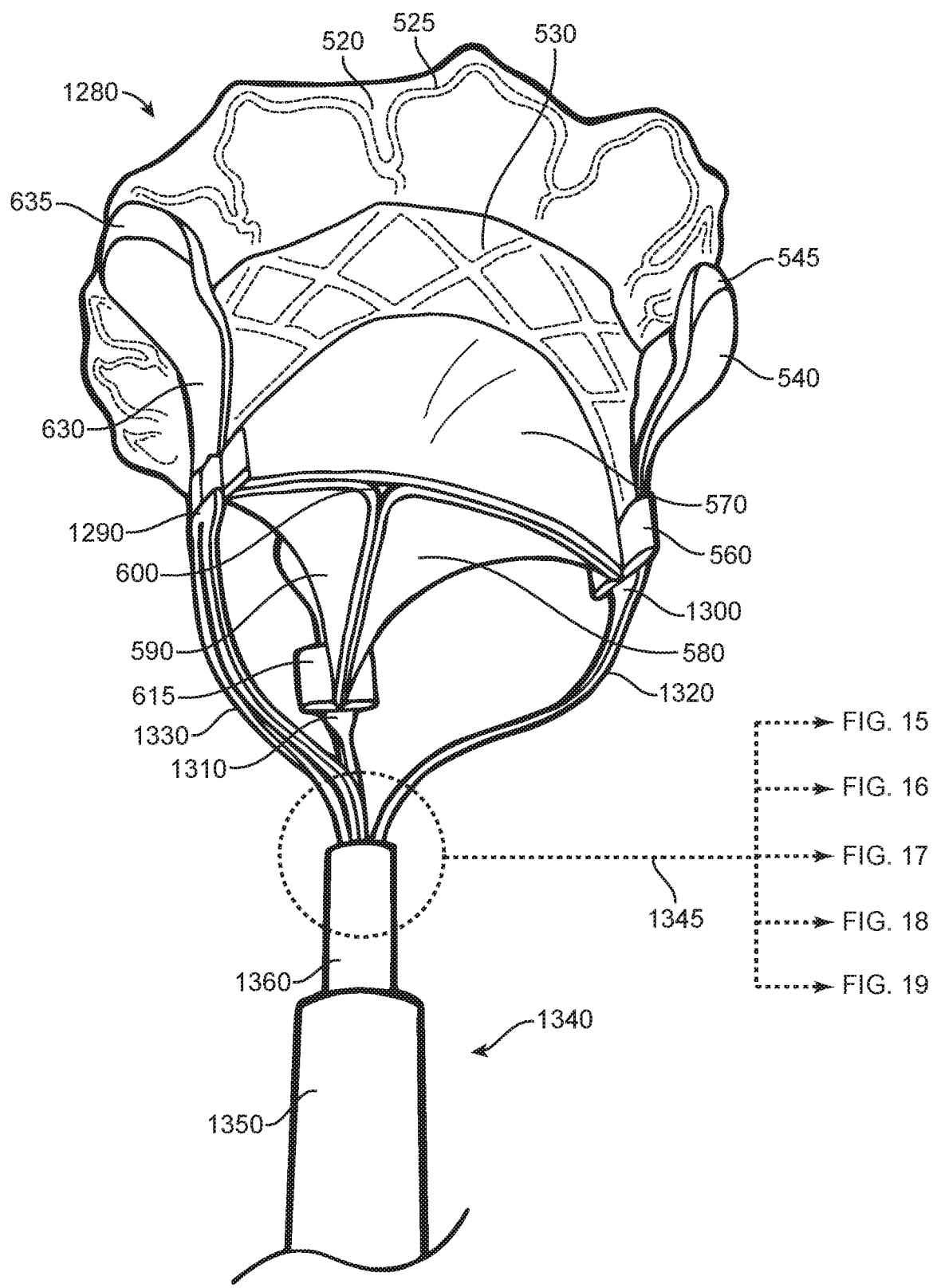
FIG. 14 illustrates an embodiment of a prosthetic mitral valve with wishbone shaped struts, anchored to a delivery system.

FIG. 14 shows the prosthetic mitral valve with wishbone attachment of FIG. 13. The prosthetic mitral valve 1280 may comprise any or all of the elements of FIG. 13. The prosthetic mitral valve 1280 may be connected to a delivery system 1340. The delivery system 1340 may comprise a completely withdrawn delivery catheter 1350. It should be readily apparent that the aforementioned postero-septal commissure anchor (1255, as shown in FIG. 13) and postero-lateral commissure anchor (1235, as shown in FIG. 13) are presently hidden by an anchoring sleeve member 1360 in FIG. 14. The delivery system 1340 is shown in FIG. 14 as connected to a non-specific anchoring mechanism. Embodiments of the anchoring mechanism are described in FIGS. 15-19, as communicated by enlarged detail element 1345.

Figure 15B:
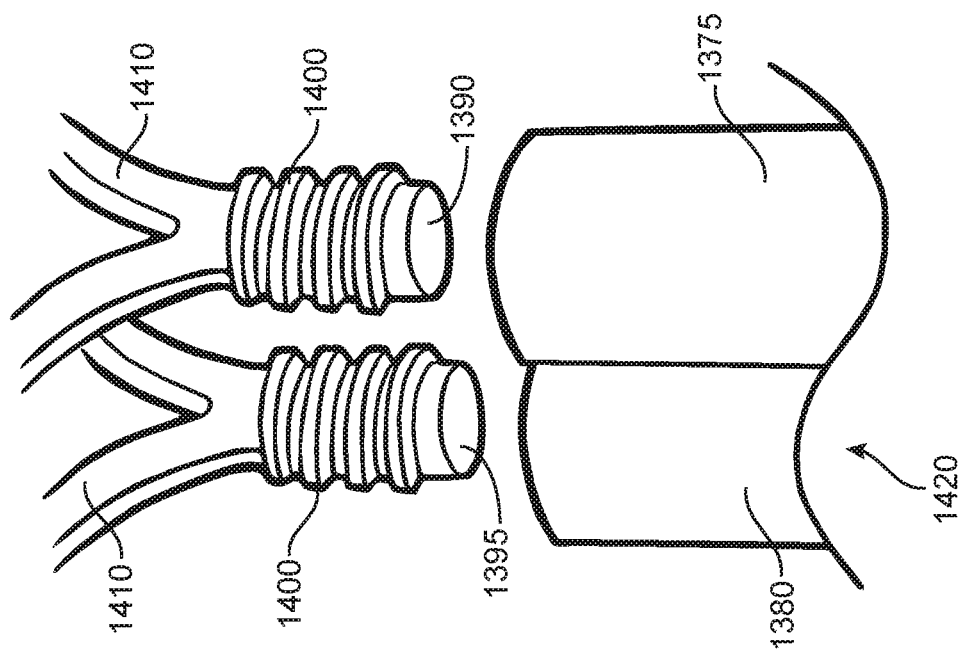
FIG. 15B shows an embodiment of a delivery system and wishbone shaped strut anchoring variation, with a plurality of threaded connectors, disconnected.
Figure 15A:
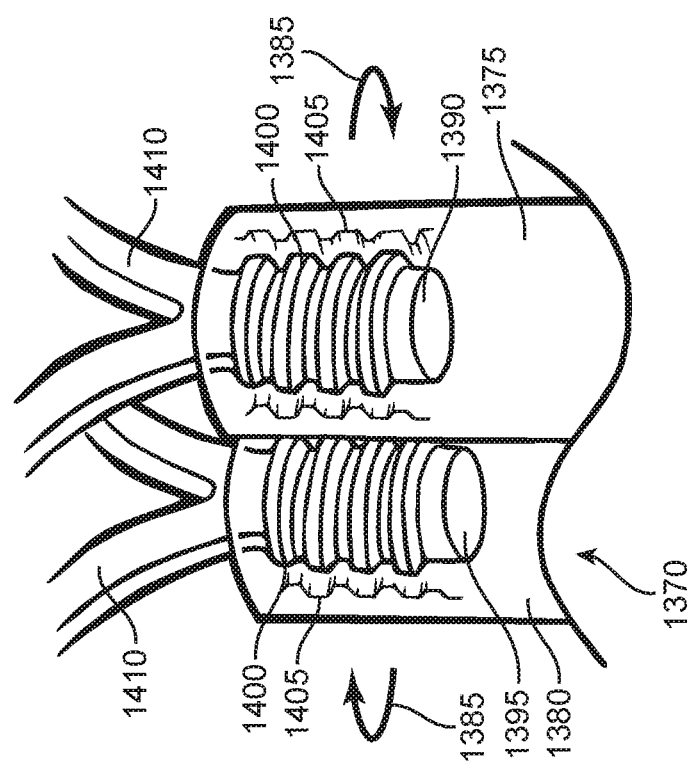
FIG. 15A shows an embodiment of a delivery system and wishbone shaped strut anchoring variation, with a plurality of threaded connectors, connected.

FIGS. 15A-B show an embodiment of an anchoring method used to anchor commissure anchors to a delivery system utilizing a plurality of threaded connectors. FIG. 15A shows a plurality of threaded connectors 1370 in a connected configuration. In the connected configuration, a first male threaded connector 1390 and a second male threaded connector 1395 may be in threaded connection with a first female threaded connector 1375 and a second female threaded connector 1380, respectively. The first and second male threaded connectors (1390 and 1395, respectively) may each comprise a segment of male threads 1400 appearing at a free end of a wishbone shaped strut 1410. The wishbone shaped strut may replace the plurality of commissure anchors (1255 and 1235, as shown in FIG. 13). The male threads may be sized to fasten and mate to similarly threaded first and second segments of female thread 1405. Arrows 1385 indicate rotation of each of the first and second female threaded connectors (1375 and 1380, respectively). Upon rotation in the direction of the arrows 1385, the connectors may be in the state depicted in FIG. 15B.

FIG. 15B shows a plurality of threaded connectors (1390 and 1395) in a disconnected configuration 1420. It should be apparent that in the state depicted in FIG. 15B, the male threaded connectors may be completely disconnected from the female threaded connectors. Upon disconnection, a prosthetic valve that was initially attached to a catheter delivery system through the wishbone connectors may be fully released from its delivery system. A further discussion of the internal mechanisms responsible for the operation of this embodiment of a delivery system begins with the description of FIG. 29.

FIGS. 16A-B show an embodiment of an anchoring method used to anchor commissure anchors to a delivery system using a single split-threaded connector. FIG. 16A shows a split-threaded connector 1430 in a connected configuration. One or more male split-threaded connectors 1450 may be in threaded connection with one or more female split-threaded connectors 1440. Each male split-threaded connector 1450 may comprise a segment of male thread 1455 appearing at a free end of a wishbone shaped strut 1460. The wishbone shaped strut may replace the plurality of commissure anchors (1255 and 1235, as shown in FIG. 13). The male threads may be sized to fasten and mate to similar threaded segments of female thread 1445 within the female threaded connector 1440. Arrows 1435 indicate rotation of the individual female threaded connector 1440. Upon rotation, the connectors may be in the state depicted in FIG. 16B.

FIG. 16B shows the split-threaded connector 1455 in a disconnected configuration 1470. It should be apparent that in the state depicted in FIG. 16B, the male split-threaded connector may be completely disconnected from the female threaded connector. Upon disconnection, a prosthetic valve that was initially attached to a catheter delivery system through the wishbone connectors may be fully released from its delivery system. A further discussion of the internal mechanisms responsible for the operation of this embodiment of a delivery system begins with the description of FIG. 27.

Figure 17B:
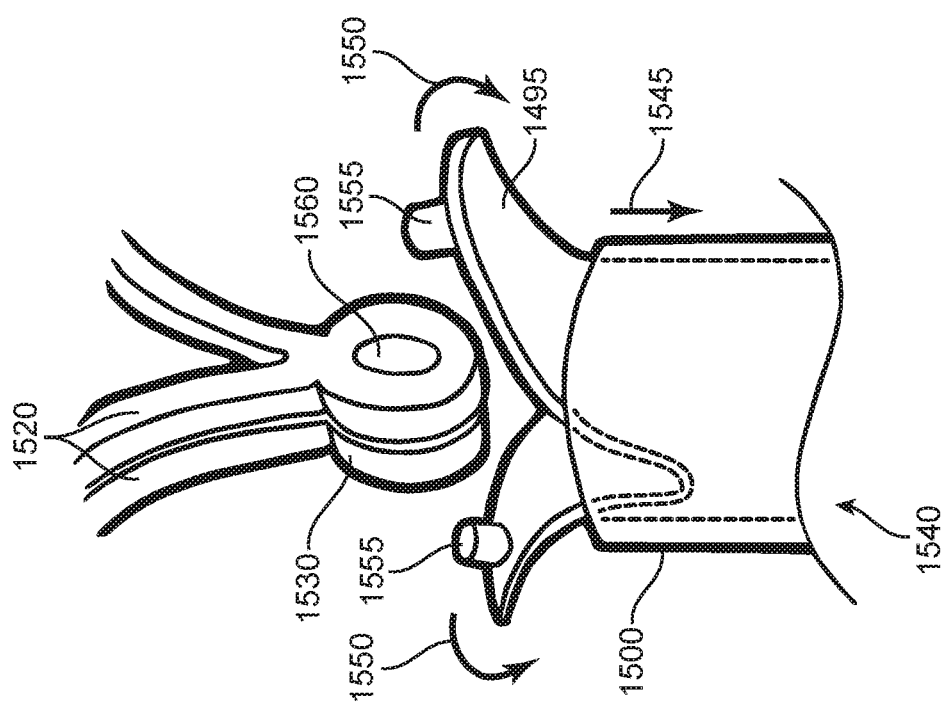
FIG. 17B shows an embodiment of a delivery system and wishbone shaped strut anchoring method, with a flexing pin connector, disconnected.
Figure 17A:
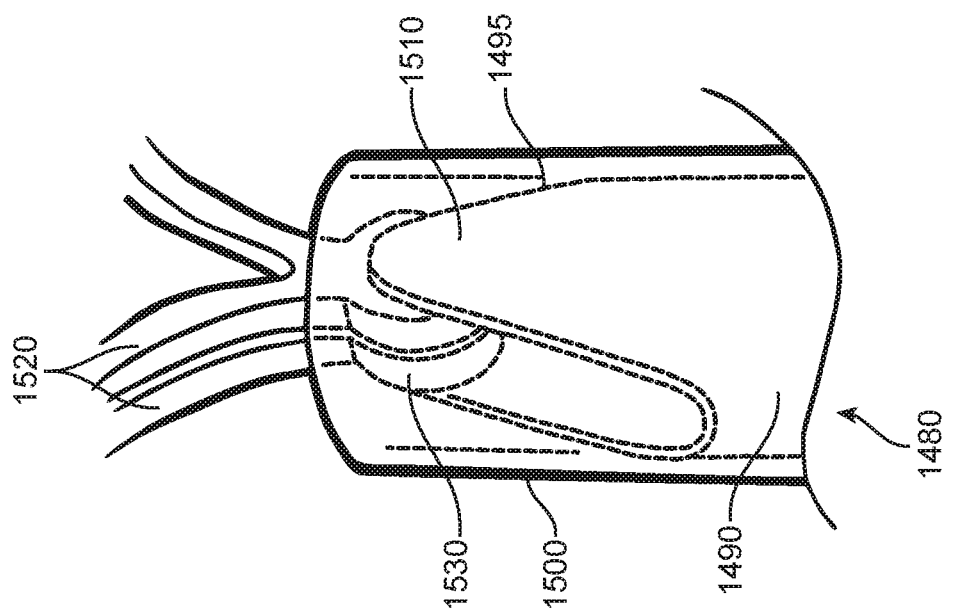
FIG. 17A shows an embodiment of a delivery system and wishbone shaped strut anchoring method, with a flexing pin connector, connected.

FIGS. 17A-B show an embodiment of an anchoring method used to anchor commissure anchors to a delivery using a flexing pin-connector type anchoring mechanism. FIG. 17A shows a flexing pin-connector type anchoring mechanism 1480 in a connected configuration. One or more flexible sleeves 1490 may be closed about a plurality of pinhole connectors 1530. The flexible sleeves 1490 may comprise a plurality of flexible sleeve portions 1495 that may be able to snap open and shut when a translating sleeve 1500 is drawn over or off of them. This movement of the translating sleeve may effective encapsulating the flexible sleeve portions 1495. The flexible sleeve 1490 may comprise a shape-settable and/or super-elastic nitinol material, as is known to those having skill in the art. Each flexible sleeve portion 1495 may comprise a terminal point 1510, appearing at the free end of the flexible sleeve 1490. The terminal points may allow connection of the flexing pin-connector type anchoring mechanism 1480 to wishbone shaped struts 1520.

FIG. 17B shows the flexing pin-connector type anchoring mechanism 1480 in a disconnected configuration 1540. The internal surface of each of the terminal points 1510 may comprise a connector pin 1555 which may fit into a complimentary hole for pin connection 1560. Each of the wishbone shaped struts 1520 of the prosthetic mitral valve may terminate in a pinhole connector 1530. The pinhole connectors may replace the plurality of commissure anchors (1255 and 1235, as shown in FIG. 13). Arrows 1550 indicate rotation of each of the individual flexible sleeve portions 1495. Upon rotation, the connector may be in the state depicted in FIG. 17B. Arrow 1545 indicates translation of the translating sleeve 1500 over the flexible sleeve portions 1495. It should be apparent that in the state depicted in FIG. 17B, the connector pins 1555 may be completely disconnected from the holes for pin connection 1560. Upon disconnection, a prosthetic valve that was initially attached to a catheter delivery system through the wishbone connectors may be fully released from its delivery system. A further discussion of the internal mechanisms responsible for the operation of this embodiment of a delivery system begins with the description of FIG. 24A.

FIGS. 18A-C show an embodiment of an anchoring method used to anchor commissure anchors to a delivery system using a plurality of flexible buckle type anchoring mechanisms is employed. FIG. 18A shows a plurality of flexible buckle type connectors 1570 in a connected configuration. A plurality of flexible buckles 1580 may be in captured connection with, restrained by, or disposed within an aperture 1575 that is sized to accept and retain the flexible buckles 1580 utilizing opposing tensile forces. The aperture may be fashioned in the side of a translating sleeve 1500. Each of the flexible buckles may be located adjacent to and protruding from the end of a wishbone shaped strut 1520, which may replace the plurality of commissure anchors (1255 and 1235, as shown in FIG. 13). A sheath catheter 1350 may be concentrically positioned over the top of the translating sleeve 1500. When the translating sleeve 1500 is drawn against the sheath catheter 1350, the mechanism of action may be achieved.

FIG. 18B depicts the hidden structure of the flexible buckles 1580, as the translating sleeve 1500 blocks said structure from view in FIG. 18A.

FIG. 18C shows the flexible buckle type anchoring mechanisms in a disconnected configuration. When the translating sleeve 1500 is drawn against the sheath catheter 1350, the flexible buckles 1585 may be forced closed by the inner surface of the sheath catheter 1500, and released from constraint. It should be apparent that in the state depicted in FIG. 18C, the flexible buckle type connectors may be completely disconnected from their aperture 1575 and associated translating sleeve 1500. Upon disconnection, a prosthetic valve that was initially attached to a catheter delivery system through wishbone connections may be fully released from its delivery system. A further discussion of the internal mechanisms responsible for the operation of this embodiment of a delivery system begins with the description of FIG. 26A.

FIGS. 19A-B show an embodiment of an anchoring method used to anchor commissure anchors to a delivery system using a plurality of anchor shaped commissure anchors. FIG. 19A shows a plurality of anchor shaped commissure anchors 1630, adjacent to and connected with the ends of a plurality of wishbone shaped struts 1410, in a connected configuration. The plurality of commissure anchors 1630 may rest within a complimentary plurality of slots 1615. The slots may act to retain the anchors and resist tensile forces that may be developed during operation of the delivery system. The slots 1615 may be fashioned on the anchoring end 1610 of an anchoring catheter 1600. The plurality of commissure anchors 1630 depicted in FIG. 19A-B may be identical to the plurality of commissure anchors (1255 and 1235, as shown in FIG. 13) in design, construction, and function.

FIG. 19B shows the commissure anchors 1640 in an unconstrained configuration that may allow disconnection. Arrow 1620 indicates translation of an anchoring sleeve member 1360. Upon translation, the state depicted in FIG. 19B may be realized. It should be apparent that in the state depicted in FIG. 19B, the commissure anchors 1640 may be unconstrained and capable of being disconnected from the slots 1615 of the anchoring catheter 1600. Upon disconnection, a prosthetic valve that was initially attached to a catheter delivery system may be released from its delivery system. A further discussion of the internal mechanisms responsible for the operation of this embodiment of a delivery system begins with the description of FIG. 21A.

FIGS. 20A-20F depict the successive stages of unsheathing an embodiment of a delivery system and implanting a mitral valve prosthesis. Although the resultant effects of the operation of said delivery system (such as the release of a constrained prosthetic mitral valve) are discussed with reference to the relevant elements necessary for illustration, the mechanical relationships of the various internal components necessary for the physical realization of the delivery system embodiments are not illustrated or discussed until further below, in FIGS. 21-31. The deployment process as depicted in FIGS. 20A-20F proceeds as follows. A sheath catheter which may constrain a compressed prosthetic valve comprised of tissues, fabrics, sutures and a nitinol frame may be retracted from the valve while in place within the implantation zone. The physiological temperature of the blood in a patient's heart may cause the nitinol material to expand and conform to the space in which it has been implanted. As the prosthesis expands, elements of the invention that are responsible for anchoring to the native anatomy may also expand, allowing the prosthesis to remain in place in order to function as a one-way valve and support proper circulation of blood. It shall be recognized that the relevant anatomy has been previously illustrated in FIGS. 1-4, but is not repeated in the following figures, leaving room to focus on the prosthesis and delivery system.

Figure 20C:
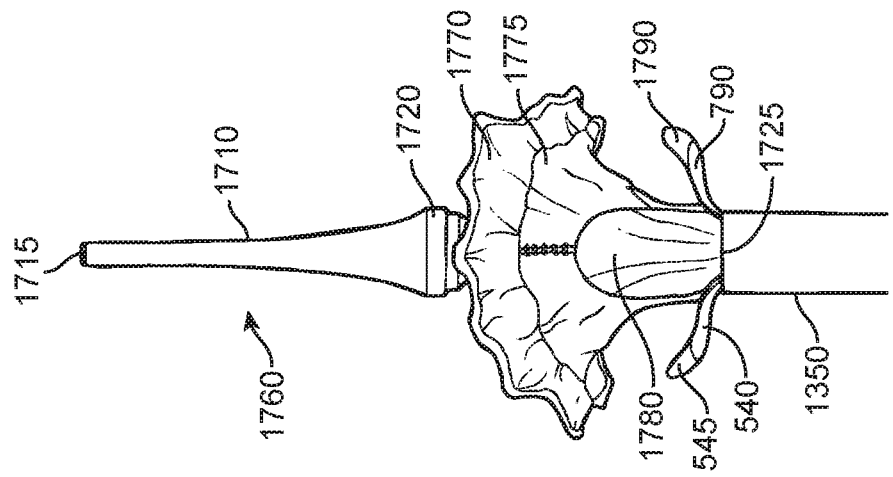
FIG. 20C depicts an embodiment of a delivery system in a substantially opened configuration, with a prosthetic mitral valve loaded internally and in mid deployment.
Figure 20B:
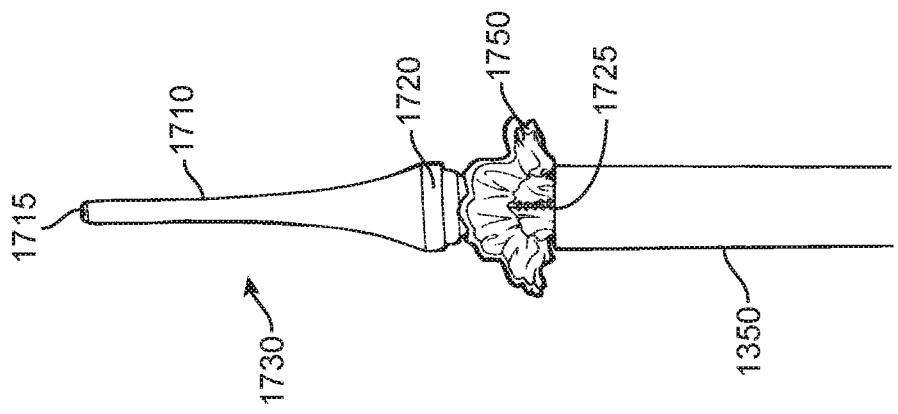
FIG. 20B depicts an embodiment of a delivery system in a partially opened configuration, with a prosthetic mitral valve loaded internally and being deployed.
Figure 20A:
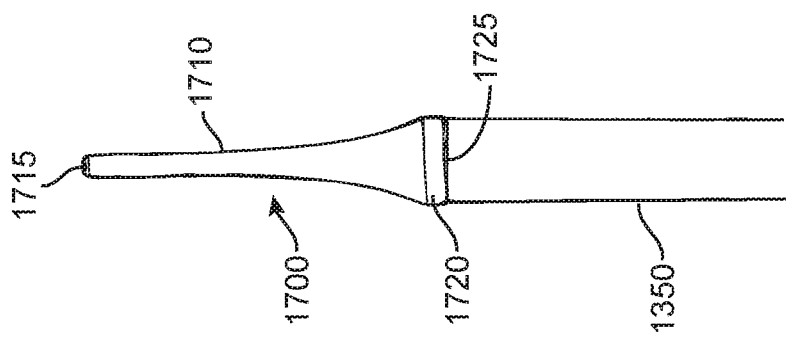
FIG. 20A depicts an embodiment of a delivery system in a closed configuration, with a prosthetic mitral valve loaded internally.

FIG. 20A depicts an embodiment of a fully loaded (sheathed and closed) delivery system 1700. The delivery system may comprise a prosthetic mitral valve (shown in FIGS. 20B-20F) that has been compressed and inserted into a sheath catheter 1350 prior to implantation. A long, tapered and flexible self-dilating dilator tip 1710 may aid the insertion of the delivery system within a small incision that is prepared in the prospective patient (not shown). The incision may be made in the thorax and may lead directly into and through the apex of the heart. The widest end of the dilator tip 1710 may be terminated by an edge 1720 that may register against and fits concentrically within a leading edge 1725 that may appear on the distal end of the sheath catheter 1350. A lumen 1715 may be formed at the distal-most portion of the dilator tip 1710, and may extend throughout the entirety of the catheter to which the dilator tip 1710 is attached.

FIG. 20B depicts an embodiment 1730 of a loaded delivery system with the atrial skirt revealed, showing the sheath catheter 1350 previously described in FIG. 20A translated a slight distance away from the dilator tip 1710. Specifically, the leading edge 1725 of the sheath catheter 1350 may be moved away from the edge 1720 of the dilator tip 1710, and may thereby reveal a partially constrained atrial skirt 1750.

FIG. 20C depicts an embodiment 1760 of a loaded delivery system with the anterior trigonal anchoring tabs revealed, showing the sheath catheter 1350 previously described in FIG. 20B translated away from the dilator tip 1710 to an even greater extent. Specifically, the leading edge 1725 of the sheath catheter 1350 may be moved further away from the edge 1720 of the dilator tip 1710, and may thereby reveal most of the structure of the encapsulated prosthetic mitral valve. An atrial skirt 1770 may now be approximately released, yet a still partially constrained annular region 1775 may remain constricted by the sheath catheter 1350. The configuration of FIG. 20C may remove a constraint that may allow the self-expansion of a portion of the prosthetic mitral valve. Adjacent to and directly beneath the constrained annular region 1775 may be a constrained anterior leaflet 1780, which may remain substantially compressed. Protruding from beneath the leading edge 1725 of the sheath catheter 1350 may be a plurality of trigonal anchoring tabs, such as an antero-lateral trigonal anchoring tab 790 (with an associated free end 1790), and an antero-septal trigonal anchoring tab 540 (with an associated free end 545).

FIG. 20D depicts an embodiment 1800 of a loaded delivery system with the anterior trigonal anchoring tabs fully open, showing the sheath catheter 1350 previously described in FIG. 20C translated away from the dilator tip 1710 to an advanced extent. Specifically, the leading edge 1725 of the sheath catheter 1350 may be moved further away from the edge 1720 of the dilator tip 1710, and may thereby reveal all of the structure of the encapsulated prosthetic mitral valve, except for the commissure attachment (not shown). The atrial skirt 1770 may now be completely unconstrained, as may an annular region 1810. Adjacent to and directly beneath annular region 1810 may be a partially constrained anterior leaflet 1825, which may be almost completely released. The anterior leaflet 1825 may be operational and able to coapt against any other leaflets present in this embodiment (not shown). The plurality of trigonal anchoring tabs (antero-lateral trigonal anchoring tab 790 and associated free end 1790, and antero-septal trigonal anchoring tab 540 and associated free end 545) may be splayed open due to the interaction between the leading edge 1725 of the sheath catheter 1350 and the still-constrained wishbone shaped struts 1820 to which the trigonal anchoring tabs may be directly connected. This opening effect may allow the trigonal anchoring tabs to reach around the native anterior mitral leaflet (460, as shown in FIG. 4) and through the anterior chordae (465, as shown in FIG. 4) in order to abut against the trigones after release. Emanating from and concentrically nested within the sheath catheter 1350 may be a guidewire catheter 1830, which may be directly connected to and provide support for the dilator tip 1710.

FIG. 20E shows an embodiment 1840 of a loaded delivery system, just prior to final release, showing the sheath catheter 1350 previously described in FIG. 20D translated away from the dilator tip 1710 to an advanced extent. Specifically, the leading edge 1725 of the sheath catheter 1350 may be moved further away from the edge 1720 of the dilator tip 1710, and may thereby reveal all of the structure of the encapsulated prosthetic mitral valve, such as the fully deployed wishbone shaped struts 1880, which may be about to be released from the delivery system. The antero-septal 1860 and antero-lateral 1870 trigonal anchoring tabs may be released from their constraint, and may now be in their final position. The anterior leaflet 1850 may be completely freed, and may be in an operable state spanning the native anterior leaflet.

FIG. 20E depicts final deployment 1890 with the delivery system removed. The wishbone shaped struts 1900 and associated commissure anchors 1910 may be entirely released and free from constraint by the delivery system. In this depiction, the prosthesis of the present invention may be fully functional, and free to operate within the native anatomy.

A thorough discussion of several relevant delivery system embodiments will now be presented, with reference to elements appearing in FIGS. 21-31.

FIGS. 21A-23 depict an embodiment of a delivery system that corresponds to the description relating to FIGS. 19A-19B and that may be compatible with the prosthetic mitral valve embodiment described in FIG. 13.

Figure 21A:
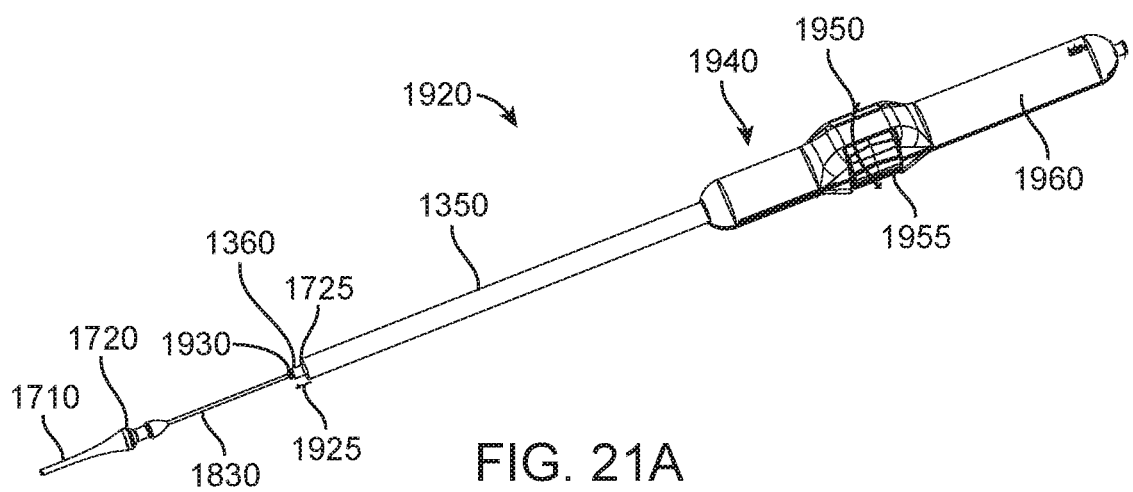
FIGS. 21A-C show an embodiment of a delivery system having a slotted anchor mechanism that may accommodate anchored wishbone shaped struts.

FIG. 21A shows an embodiment of a fully open, extended-length delivery system 1920. The delivery system may comprise a delivery system handle 1940. The delivery system handle may comprise a slender, graspable member 1960 that may allow for the housing of various mechanical components, and may provide a location for a family of concentrically nested catheters. The delivery system handle 1940 may also provide an actuation mechanism, such as in the form of a rotatable (see arrow 1950 indicating rotation) thumbwheel 1955. The thumbwheel may be substantially cylindrical and may have internal threads (not shown) that transform rotational torque applied by a user into linear force. The linear force may be used to translate certain catheters from the family of concentrically nested catheters. The previously discussed sheath catheter 1350 is again present and may be a substantially cylindrical tube with an inner lumen, extending from within the delivery system handle 1940 to a leading edge 1725 that may transit the distance between the edge 1720 of a dilator tip 1710 positioned at the distal-most extremity of the entire device and a set distance proximally away from the edge 1720 that may equate substantially to the constrained length of a prosthetic valve (not shown). An anchoring sleeve member 1360 may be concentrically nested within the sheath catheter 1350, which may itself also have an inner lumen that extends from within the delivery system handle 1940 up to and slightly beyond the tip of an anchoring catheter 1930. The anchoring catheter 1930 may itself be cylindrical and concentrically nested within the anchoring sleeve member 1360. Further detail regarding the anchoring catheter 1930 is provided in FIG. 22. The innermost concentrically nested catheter is the guidewire catheter 1830, which may be connected to the dilator tip 1710. There may be an inner lumen extending through the entire length of the delivery system, which may be appropriately sized to receive and transmit a guidewire (not shown) that may be placed within it. An arrow 1925 depicting translation shows how the sheath catheter 1350 may be brought toward the dilator tip 1710 as the thumbwheel 1955 is rotated.

Figure 21B:
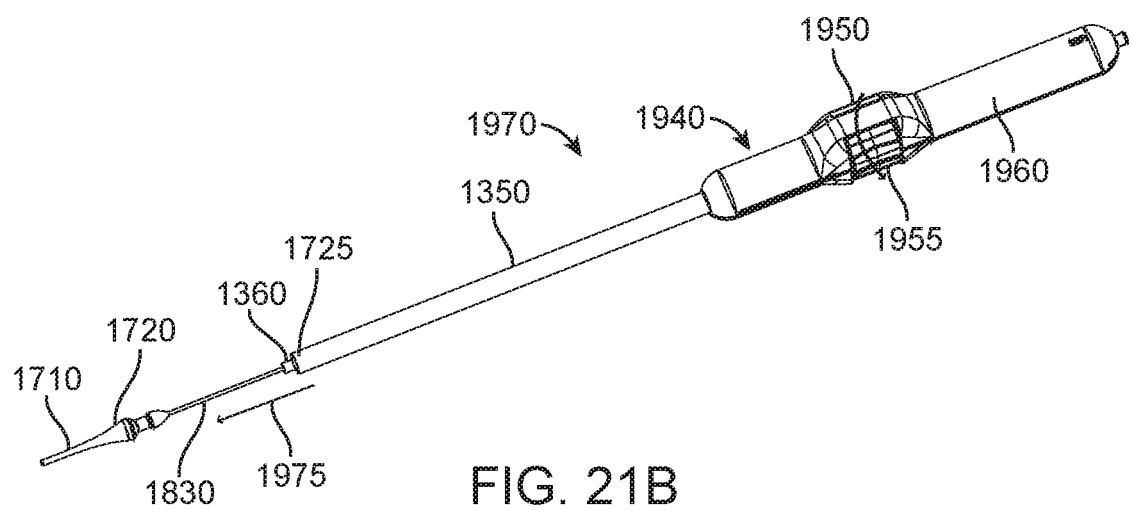

FIG. 21B shows the device introduced in FIG. 21A in a configuration 1970, with the sole differences being the position of the sheath catheter 1350 and the position of the anchoring sleeve member 1360. The sheath catheter may be translated even further toward the dilator tip 1710 (as depicted by arrow 1975 indicating translation). The anchoring sleeve member 1360 may also be translated. By translating toward the dilator tip 1710, the anchoring sleeve member 1360 may effectively cover up the anchoring catheter 1930, FIG. 21A. This is the same mechanical relationship depicted in FIGS. 19A and 19B, although in the reverse order.

Figure 21C:
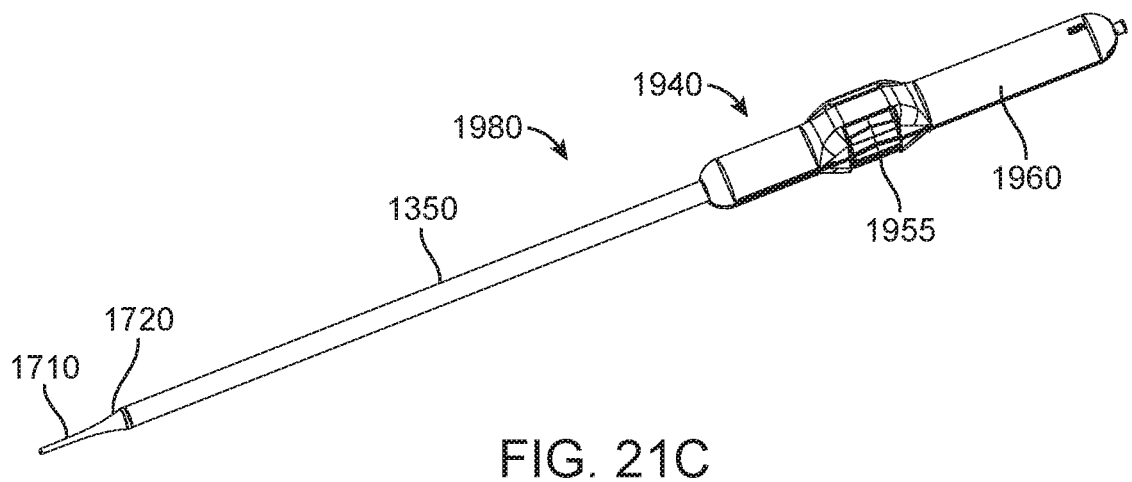

FIG. 21C shows a closed delivery system 1980, wherein the thumbwheel 1955 may be rotated to its full extent, and the sheath catheter 1350 may be brought to close against the dilator tip 1710.

Figure 22:
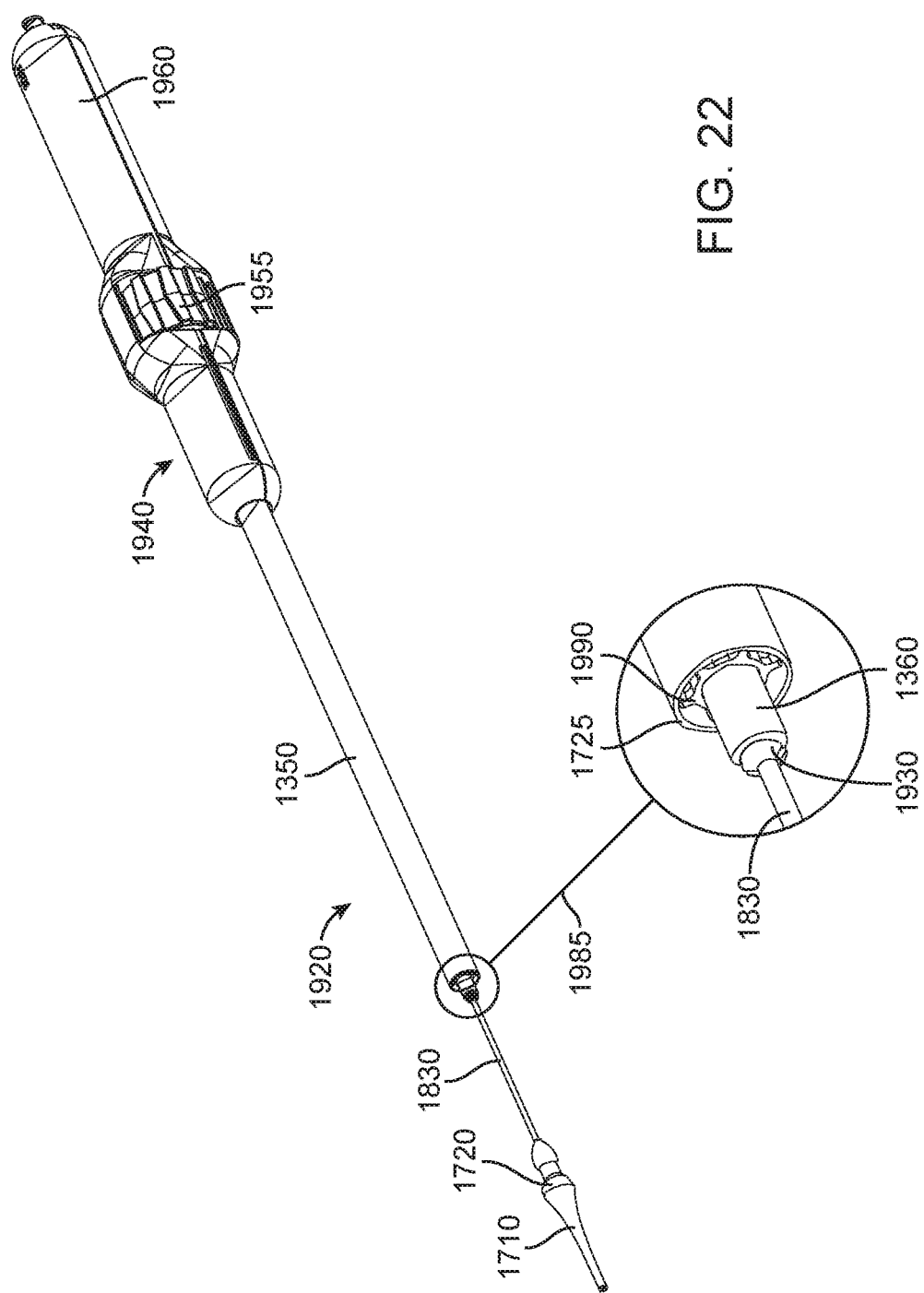
FIG. 22 shows an enlarged view of an embodiment of a delivery system having a slotted anchor mechanism that may accommodate anchored wishbone shaped struts.

FIG. 22 shows the embodiment and configuration of the device as illustrated in FIG. 21A with additional detail in the form of an enlarged view 1985. Specifically, a stabilizer member 1990 may be located between the inner surface of the sheath catheter 1350 and the outer surface of the anchoring sleeve member 1360. The stabilizer member may take the form of a star shaped cylindrical prism. The stabilizer member may force concentricity between said catheters while still allowing blood and/or saline to flow past. The slotted end of the anchoring catheter 1930 is also portrayed. It may be seen that the anchoring sleeve member 1360 may be positioned concentrically around and in slidable communication with the anchoring catheter 1930. The guidewire catheter 1830 is again shown exiting the anchoring catheter 1930.

Figure 23:
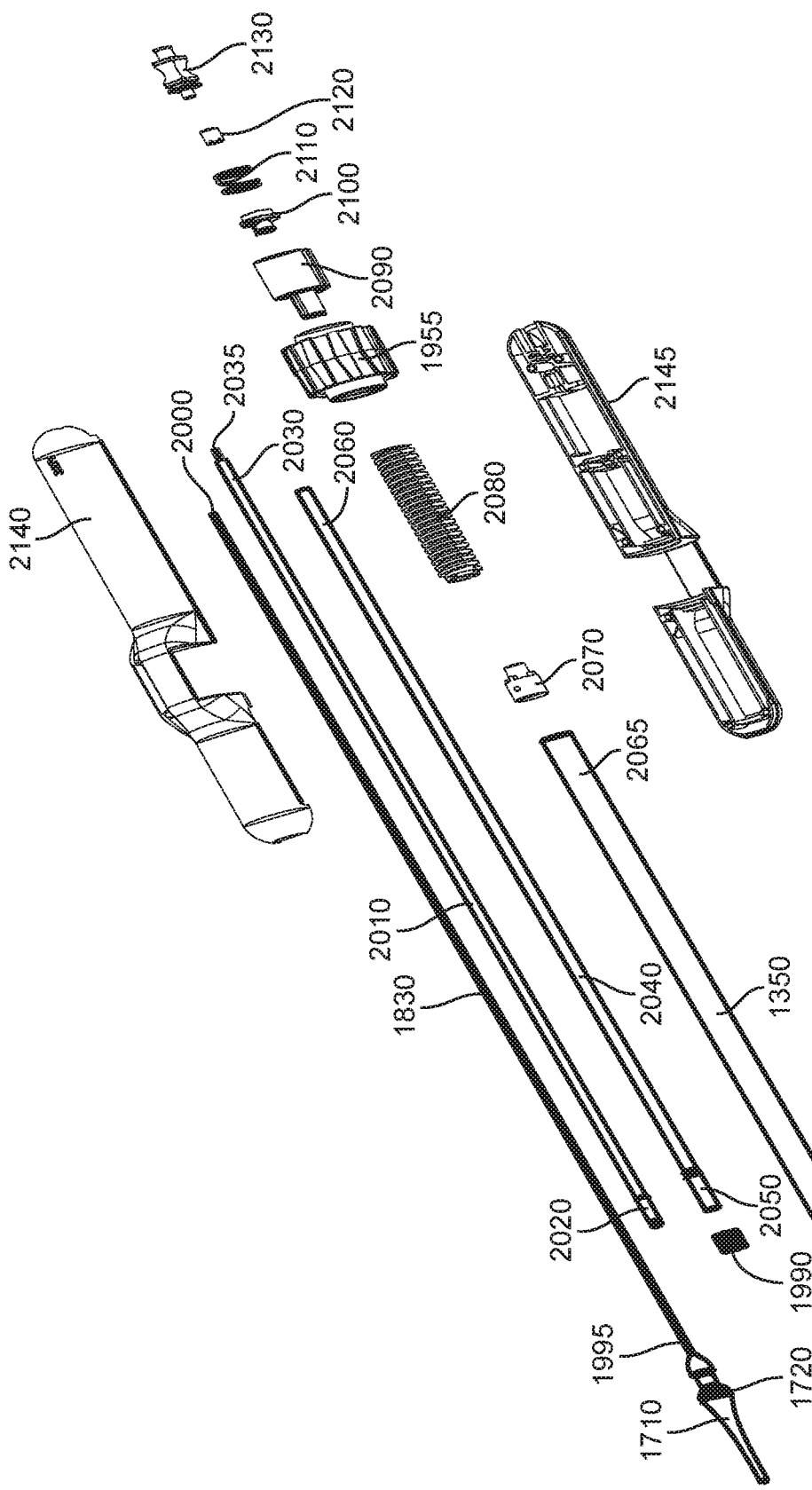
FIG. 23 shows an exploded view of a delivery system having a slotted anchor mechanism that may accommodate anchored wishbone shaped struts.

FIG. 23 illustrates an exploded view of the exemplary device of FIGS. 21A-22B. The device may comprise a delivery system handle A-side 2140 that may be in mated connection with a delivery system handle B-side 2145. The device may effectively provide a housing and location for the family of concentrically nested catheters seen to the left side of the handle elements (and described in FIGS. 22-22), and the various elements seen to the right side of the handle elements. The device may comprise a needle hub 2130, which may be in mated connection with the proximal end 2000 of the guidewire catheter 1830. The mated connection may be formed using adhesives. The needle hub 2130 may act as a connecting port, through which a syringe (not shown) may be attached to the device and used to flush sterile saline through the innermost lumen to remove air prior to insertion into a patient. A cylindrical anchoring nut 2120 may be in threaded connection with threads on the proximal end 2035 of the anchoring catheter 2010. The cylindrical anchoring nut may be located within the plurality of handle halves 2140 and 2145 so as to fasten the anchoring catheter 2010 to the delivery system. An inner lumen may run the entirety of the length of the anchoring catheter 2010 and may allow for the concentric nesting of the guidewire catheter 1830 within. A spring 2110 may be mated to and press against a bell slider cap 2100, which may itself mated to a bell slider 2090. The spring 2110 may provide a bias force with which the bell slider 2090 may be moved when a leadscrew 2080 is brought out of contact with it. In other words, by rotating the thumbwheel 1955, the leadscrew 2080 may be translated linearly and may be brought into contact with the distal portion of the bell slider 2090, which may in turn be biased against the spring 2110. The bell slider 2090 may act as a carriage for the proximal end 2060 of the bell catheter 2040 (previously referred to as an anchoring sleeve member 1360) and may allow the distal end 2050 of said bell catheter 2040 to be brought away from the distal end 2020 of the anchoring catheter 2010, which may be the mechanism responsible for final valve commissure release. The leadscrew 2080 may also be translated in an opposite direction by turning the thumbwheel 1955, in order to close the delivery system and seal the valve inside. This may be achieved by way of the leadscrew's 2080 connection to a leadscrew cap 2070, which may itself be mated to the proximal end 2065 of the sheath catheter 1350. Thus, rotating the thumbwheel 1955 in a first direction may move the leadscrew 2080 towards the dilator tip 1710, and by extension may also move the sheath catheter 1350 towards said dilator tip 1710 in order to close the device. Rotating the thumbwheel 1955 in a second opposite direction may move the leadscrew 2080 towards the bell slider 2090 and by extension may move both the sheath catheter 1350 and the bell catheter 2040 away from the dilator tip 1710 to open the device and release the prosthetic valve contained within. It should be understood that while both the sheath catheter 1350 and bell catheter 2040 may move synchronously by way of thumbwheel 1955 rotation, there may be a delay in contact provided by the dimensions of the relevant catheters and leadscrew 2080. The delay may allow some portions of the prosthesis to be uncovered before other portions as the deployment progresses. It should also be understood that the prosthetic valve may ultimately be recaptured or obtained for repositioning or removal by simply closing the sheath catheter 1350 until the leading edge 1725 of said sheath catheter 1350 again contacts the edge 1720 of the dilator tip

1710. Finally, a distal end 1995 of the guidewire catheter 1830 may be in mated connection with and anchored to the dilator tip 1710.

Figure 24A:
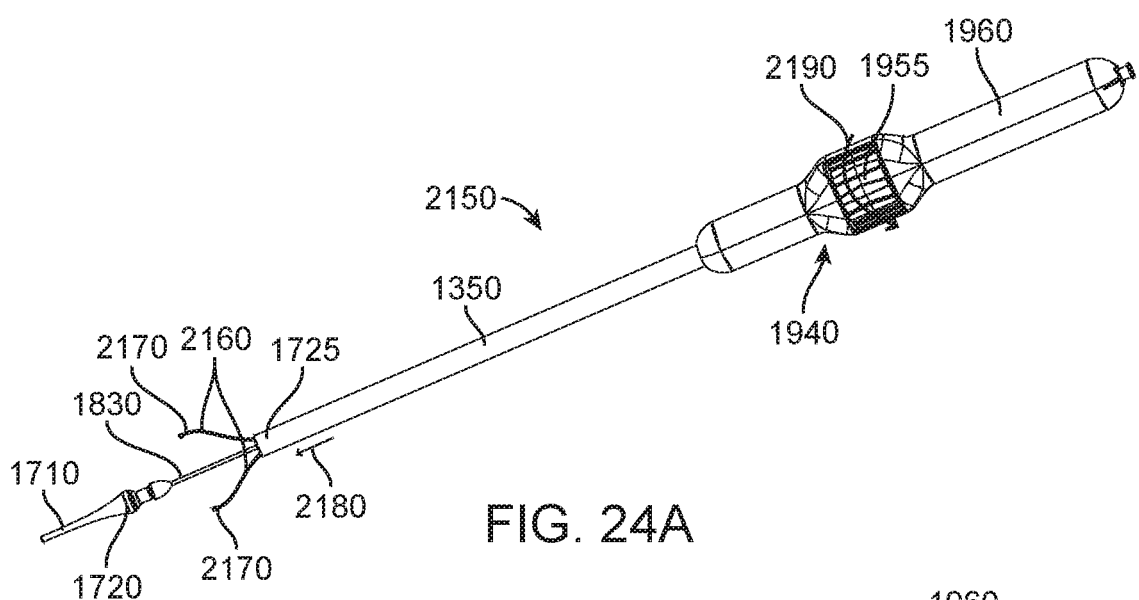
FIGS. 24A-C show an embodiment of a delivery system having a flexible connector anchor mechanism that may accommodate pinned wishbone shaped struts.
Figure 24B:
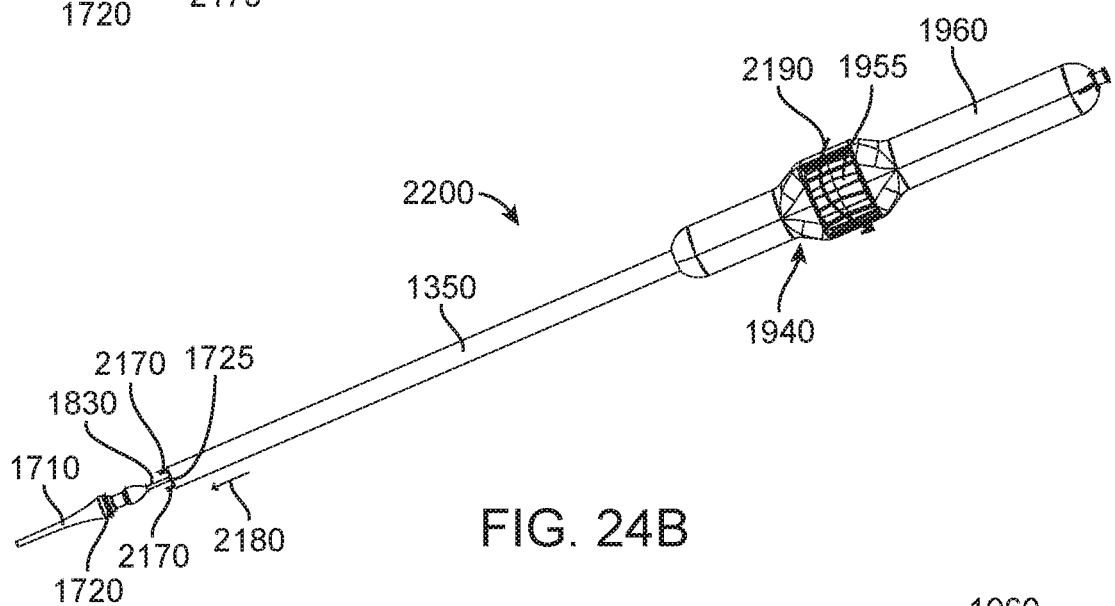
Figure 24C:
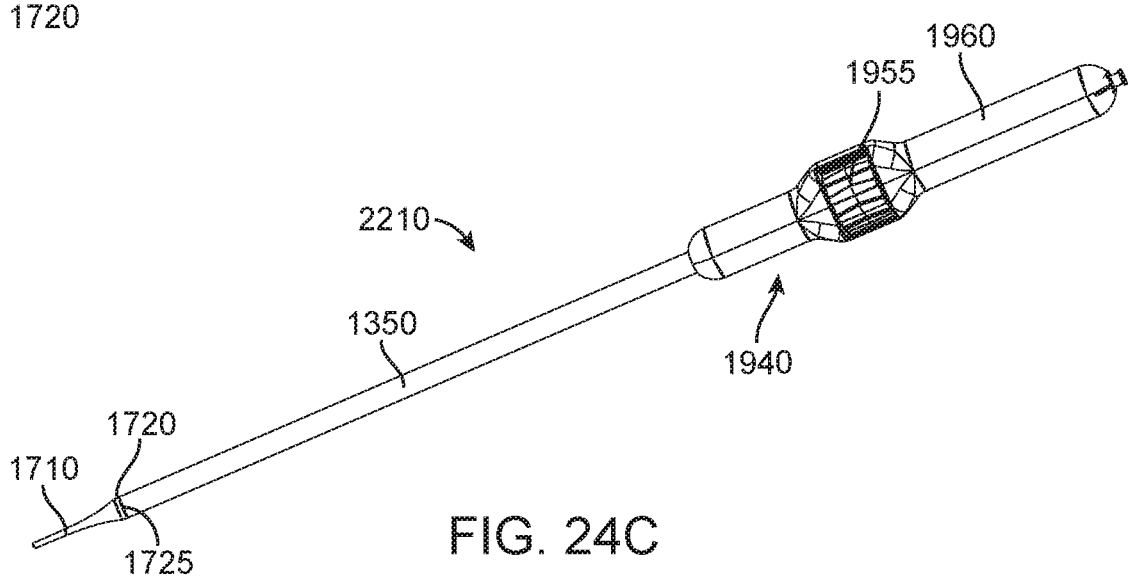
Figure 25:
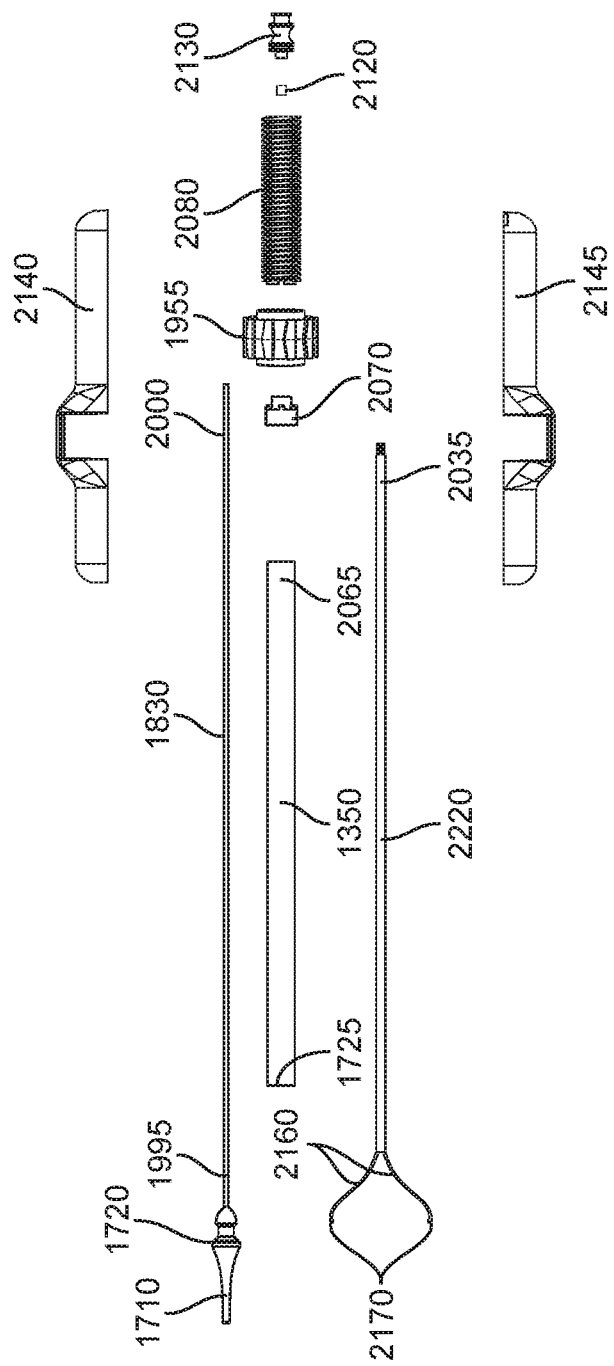
FIG. 25 depicts an exploded view of an embodiment of a delivery system having a flexible connector anchor mechanism that may accommodate pinned wishbone shaped struts.

FIGS. 24A-25 depict an embodiment of a delivery system corresponding to the description relating to FIGS. 17A-17B. In the same manner as the illustrations depicted in FIGS. 24A-24C, the relationship between thumbwheel 1955 rotation and sheath catheter 1350 translation is also depicted here. In FIG. 24A, a fully open delivery system 2150 may be designed for a flexible connection type of attachment to a prosthetic valve (not shown). An arrow 2190 indicating rotation shows that as the thumbwheel 1955 is rotated, the sheath catheter 1350 may again translate (see arrow 2180 indicating translation) toward the dilator tip 1710. In this embodiment, a plurality of flexible connector prongs 2160 may be subjected to a camming action due to their inherent arcuate profile and the gradually increasing level of contact between said flexible connector prongs 2160 and the leading edge 1725 of the sheath catheter 1350. This may bring the flexible connector prongs 2160 into close contact with one another. At the distal tip of each flexible connector prong 2160 may be a connecting element 2170, which may be a substantially cylindrical boss that may mate with a substantially cylindrical hole or cavity within the commissure element of an associated prosthetic valve (elements 1530, 1555, and 1560 show in FIG. 17B). FIGS. 24B and 24C show the logical continuation of the sheathing process (2200 partially open, FIG. 24B, and 2210 fully closed, FIG. 24C) whereby the leading edge 1725 of the sheath catheter 1350 may be eventually brought into contact with the edge 1720 of the dilator tip 1710.

FIG. 25 shows an exploded view of the delivery system introduced in FIG. 24A-24C. The components set forth in this depiction may differ only slightly from the components set forth in FIG. 23. The embodiment of a delivery system as shown in FIG. 25 may not require a bell catheter, as the capturing mechanism may be provided by the relationship between the leading edge 1725 of the sheath catheter 1350 and the plurality of flexible connector prongs 2160. Therefore, the embodiment of FIG. 25 may not require a bell slider either. In order to operate the device, a user may only need to draw the sheath catheter 1350 back and forth with the thumbwheel 1955, directly compressing the plurality of flexible connector prongs 2160. It should be readily understood that the flexible connector prongs 2160 may be fashioned into the distal end of the flexible prong anchoring catheter 2220.

Figure 26A:
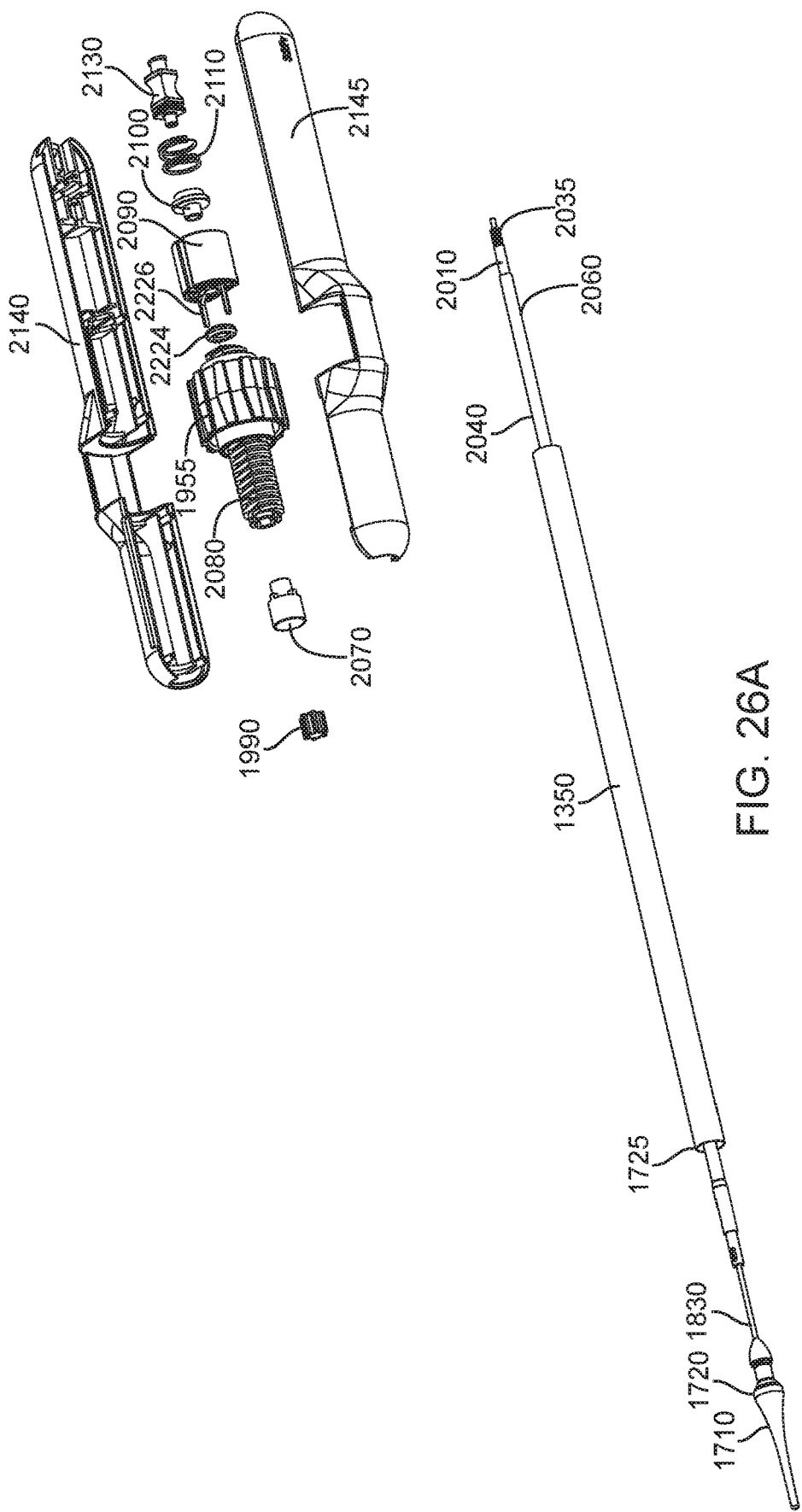
FIG. 26A depicts an exploded view of an embodiment of a delivery system having a sliding connector anchor mechanism that may accommodate flexible buckle wishbone shaped struts.
Figure 26B:
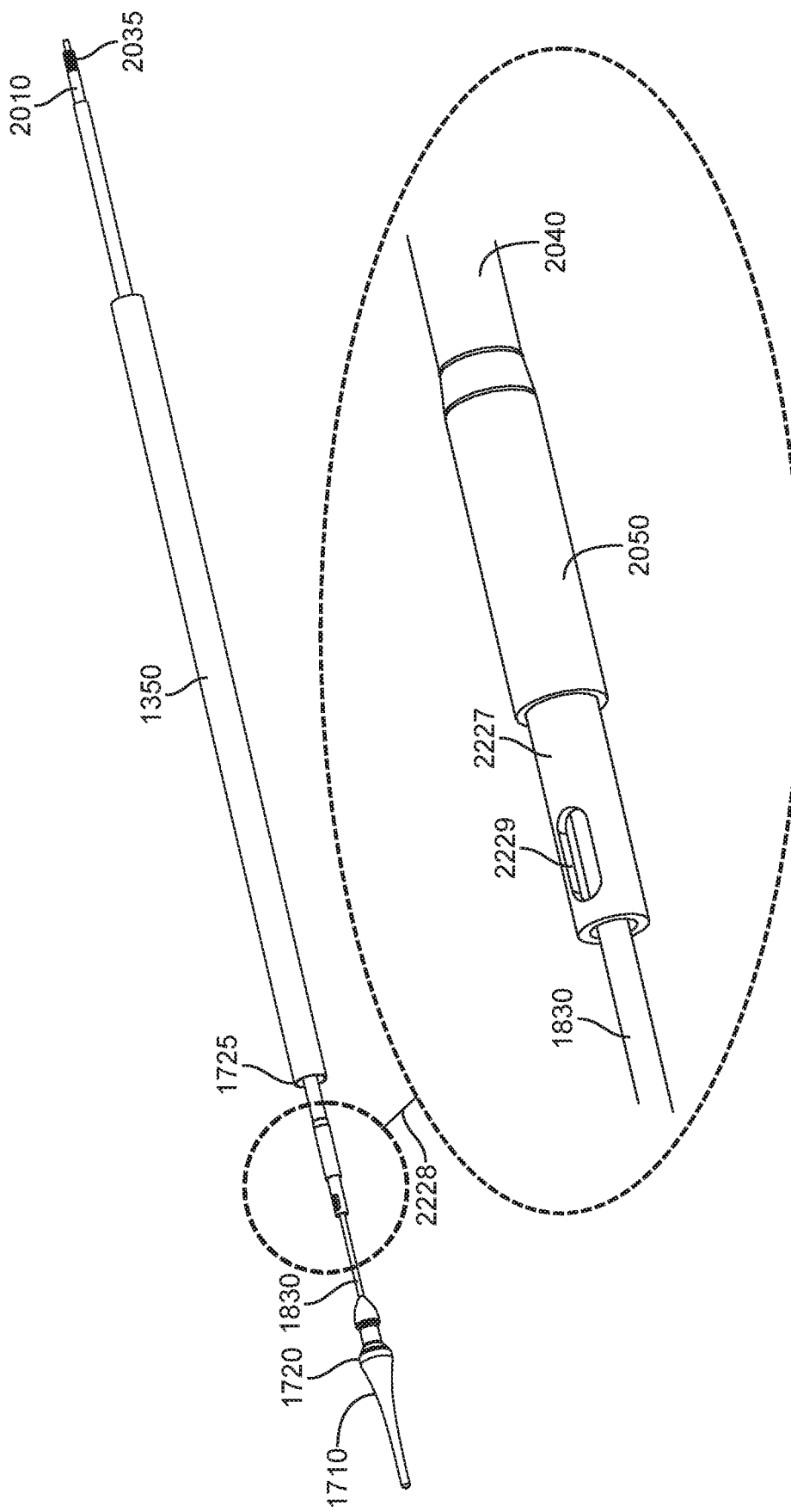
FIG. 26B depicts an enlarged view of an embodiment of a delivery system having a sliding connector anchor mechanism that may accommodate flexible buckle wishbone shaped struts.

FIGS. 26A-26B depict an embodiment of a delivery system corresponding to the description relating to FIGS. 18A-18C. FIG. 26A shows an exploded view of an embodiment of a delivery system that may be suitable for connecting with a prosthetic valve frame having flexible buckle type anchors. The components set forth in this depiction may differ only slightly from the components set forth in FIG. 23. In the embodiment of FIGS. 26A-26B, the proximal end 2035 of the anchoring catheter 2010 may be in mated connection with the bell slider 2090 instead of an anchoring nut and may be able to freely translate along with the bell slider 2090 when contacted by the leadscrew 2080. The bell slider 2090 may further comprise a plurality of pins 2226 that may transmit the force from the leadscrew 2080 to the bell slider 2090 while also providing clearance for a stationary bell catheter nut 2224 that may anchor and retain the stationary bell catheter 2040 to the delivery system. Thus, by rotating the thumbwheel 1955 the leadscrew 2080 may be brought into contact with the plurality of pins 2226, forcing the bell slider 2090 and anchoring catheter 2010 proximally away from the dilator tip 1710. This may effectively retracts the anchoring catheter 2010 into the stationary bell catheter 2040. This relationship is illustrated in greater detail in FIG. 26B.

In FIG. 26B, an enlarged view 2228 is provided, which shows in detail the elements that may be present at the distal most end of the translating anchoring catheter 2010 and stationary bell catheter 2040. When the distal end 2227 of the anchoring catheter 2010 is brought into the distal end 2050 of the bell catheter 2040, an aperture 2229 that may be formed within the distal end 2227 of the anchoring catheter 2010 may also brought into said bell catheter distal end 2050. This action effectively may provide the mechanism behind the embodiment illustrated in FIGS. 18A-18C.

Figure 27:
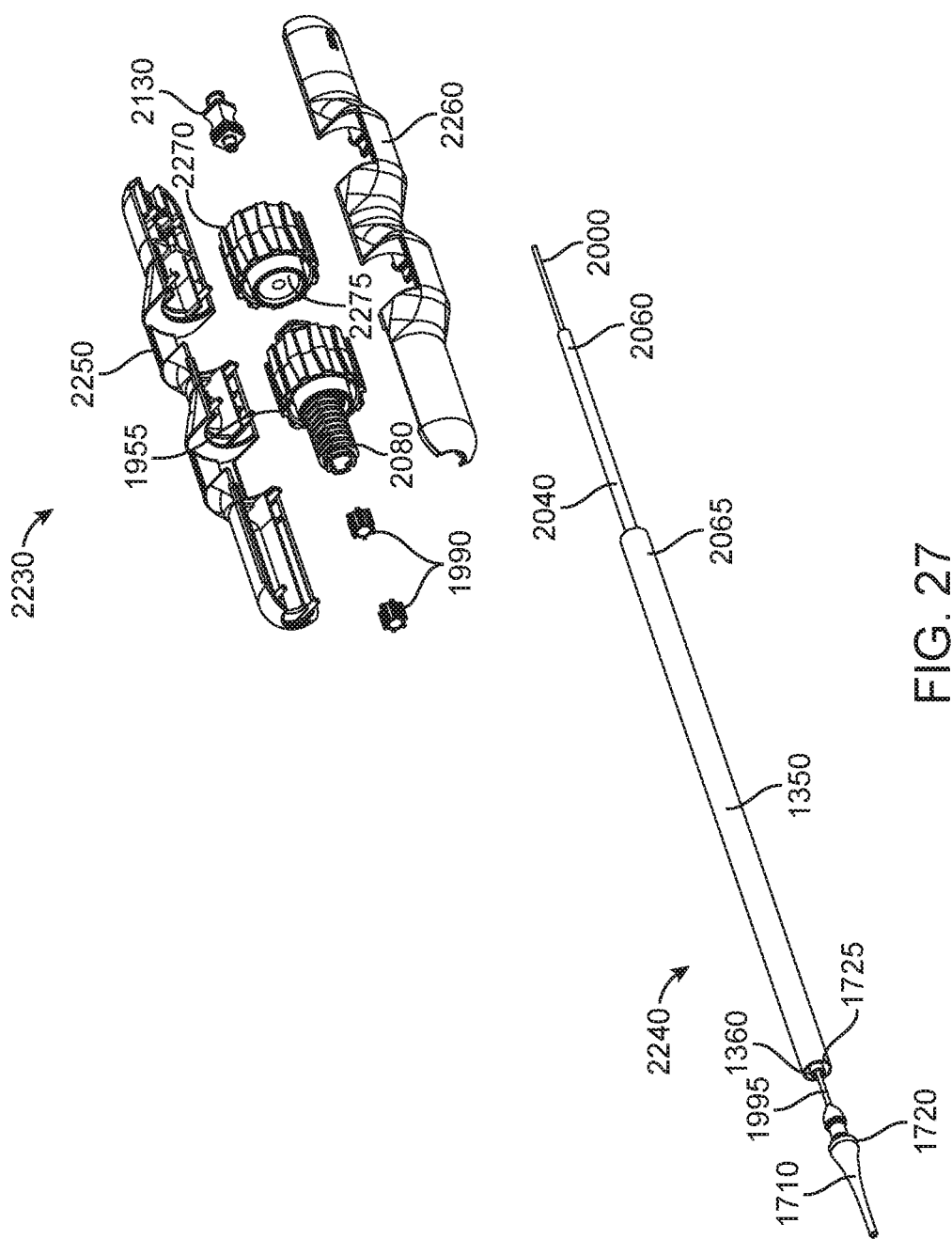
FIG. 27 depicts an exploded view of an embodiment of a delivery system with a singular screw connector anchor mechanism that may accommodate split-threaded wishbone shaped struts.
Figure 28:
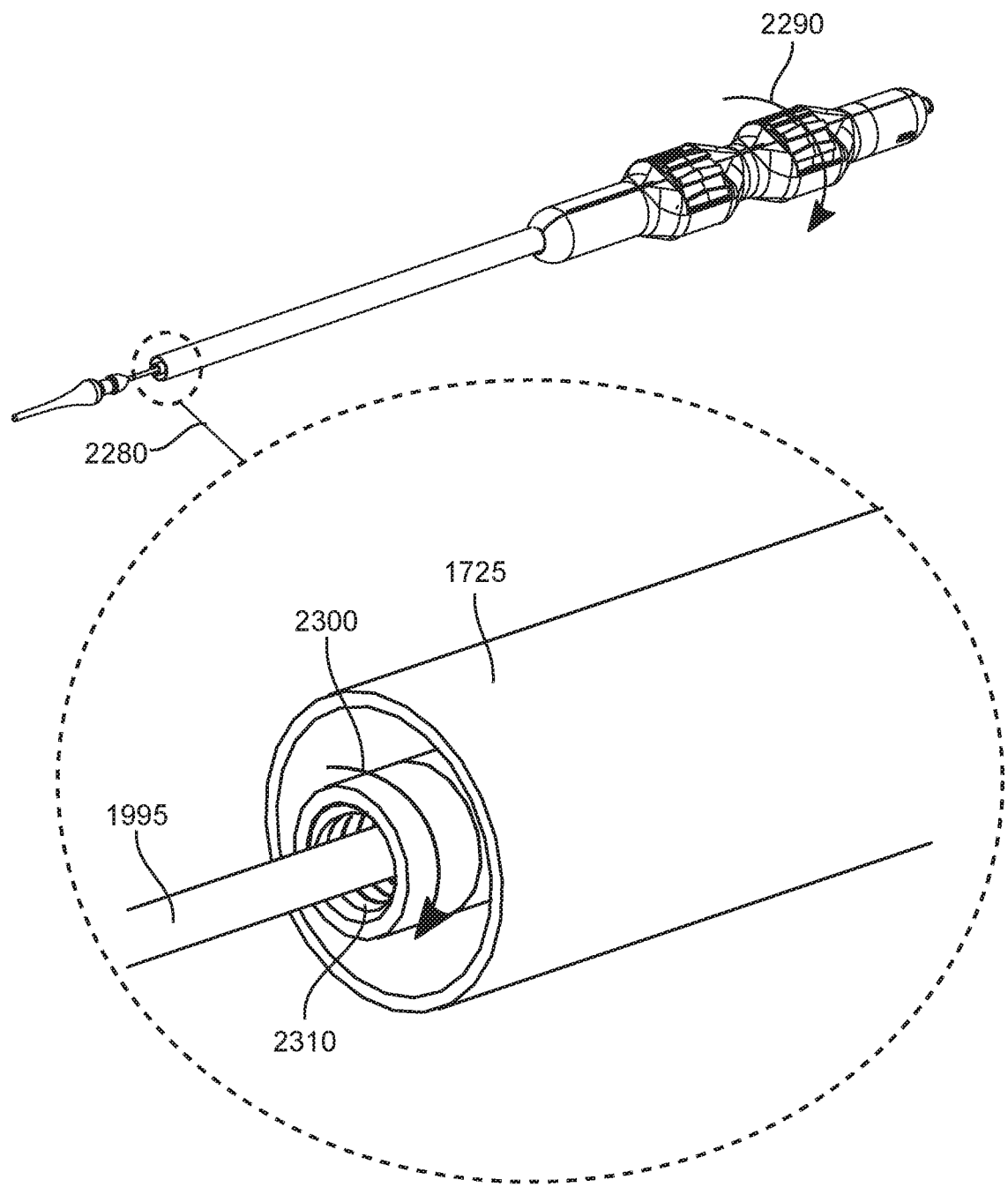
FIG. 28 shows an enlarged view of an embodiment of a delivery system with a singular screw connector anchor mechanism that may accommodate split-threaded wishbone shaped struts.

FIGS. 27 and 28 depict an embodiment of a delivery system corresponding to the description relating to FIGS. 16A-16B. FIG. 27 shows an exploded view 2230 of an embodiment of a delivery system that may suitable for connecting with a prosthetic valve frame having a single threaded connector anchor. The components set forth in this depiction may differ only slightly from the components set forth in FIG. 23. The embodiment may comprise a plurality of stabilizers 1990. The stabilizers may improve concentricity of the concentrically nested catheters. Again, a plurality of handle halves (A-side 2250, and B-side 2260) may provide a location for the various internal components. The delivery system may also comprise a plurality of thumbwheels, such as a first thumbwheel 1955 for actuating the sheath catheter 1350 and a second thumbwheel 2270 for rotating the threaded bell catheter 2040. The first and second thumbwheels may allow the catheter to connect and disconnect from the related prosthetic valve. Further, the second thumbwheel 2270 may contain a hole 2275 through which the proximal end 2060 of the rotating bell catheter 2040 may be fastened to said second thumbwheel 2270. An exploded view 2240 of the family of concentrically nested catheters is provided, and further detail regarding the threaded mechanism at the distal end of the family of catheters is provided in FIG. 28.

FIG. 28 shows an exploded view 2280 focusing on the distal end of the family of nested catheters. Arrow 2300 indicates rotation, which corresponds to the rotation of the threaded and distal end of the bell catheter 2310 in order to connect or disconnect from threaded fasteners that may be present in a valve prosthesis.

Figure 29:
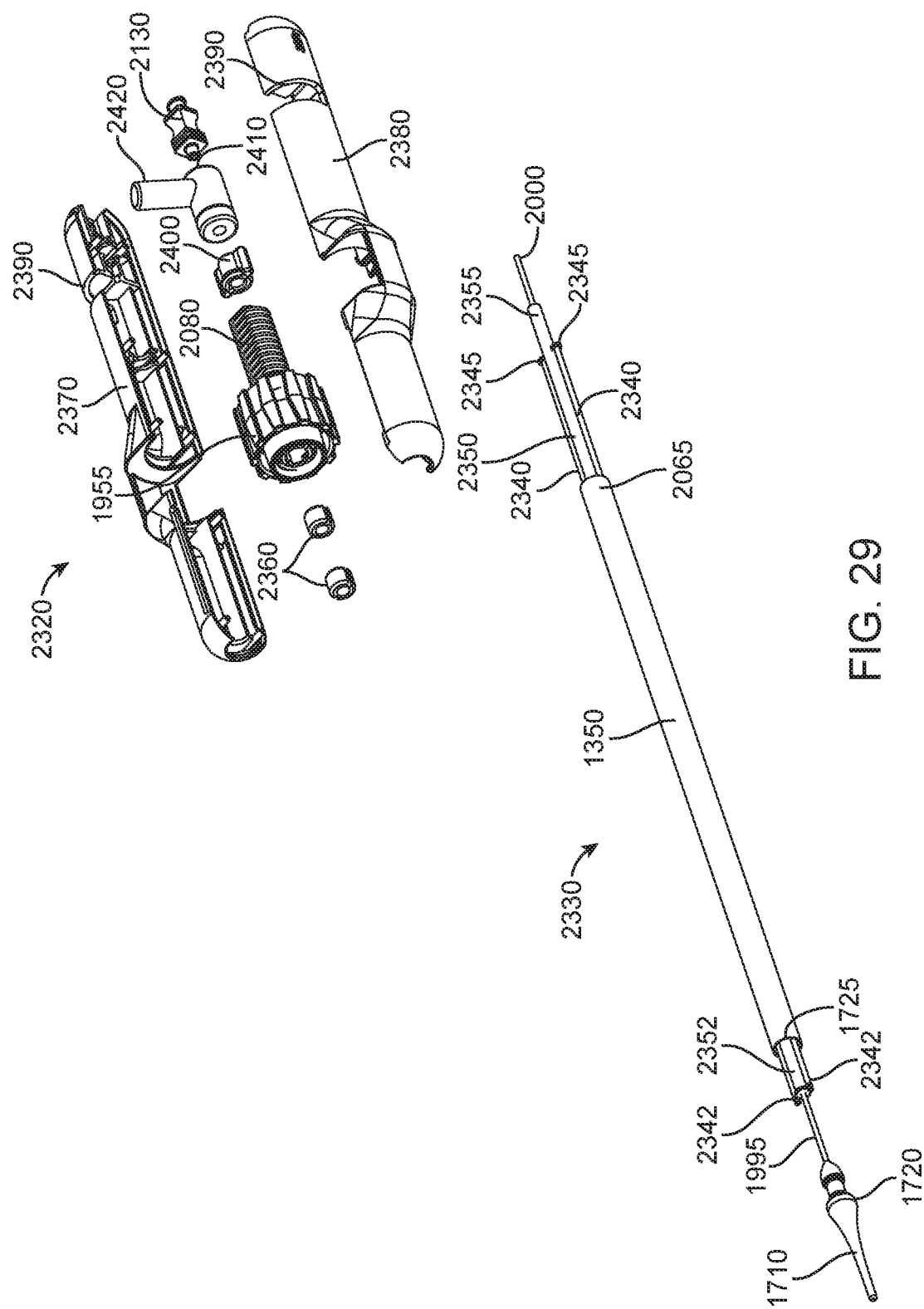
FIG. 29 shows an exploded view of an embodiment of a delivery system with a plurality of screw connector anchor mechanisms that may accommodate threaded wishbone shaped struts.
Figure 30:
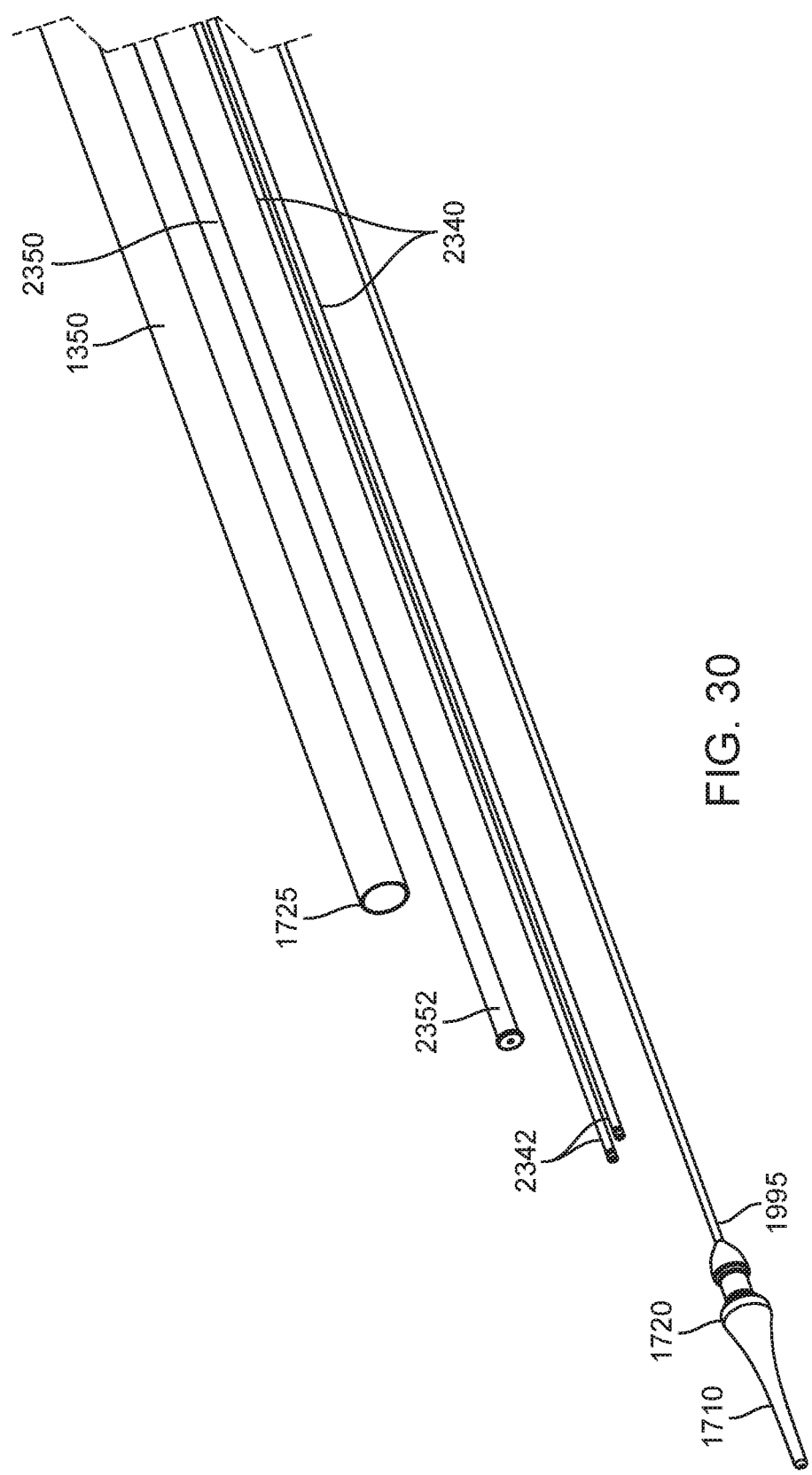
FIG. 30 shows an exploded view of the concentric catheters of an embodiment of a delivery system with a plurality of screw connector anchor mechanisms that may accommodate threaded wishbone shaped struts.
Figure 31:
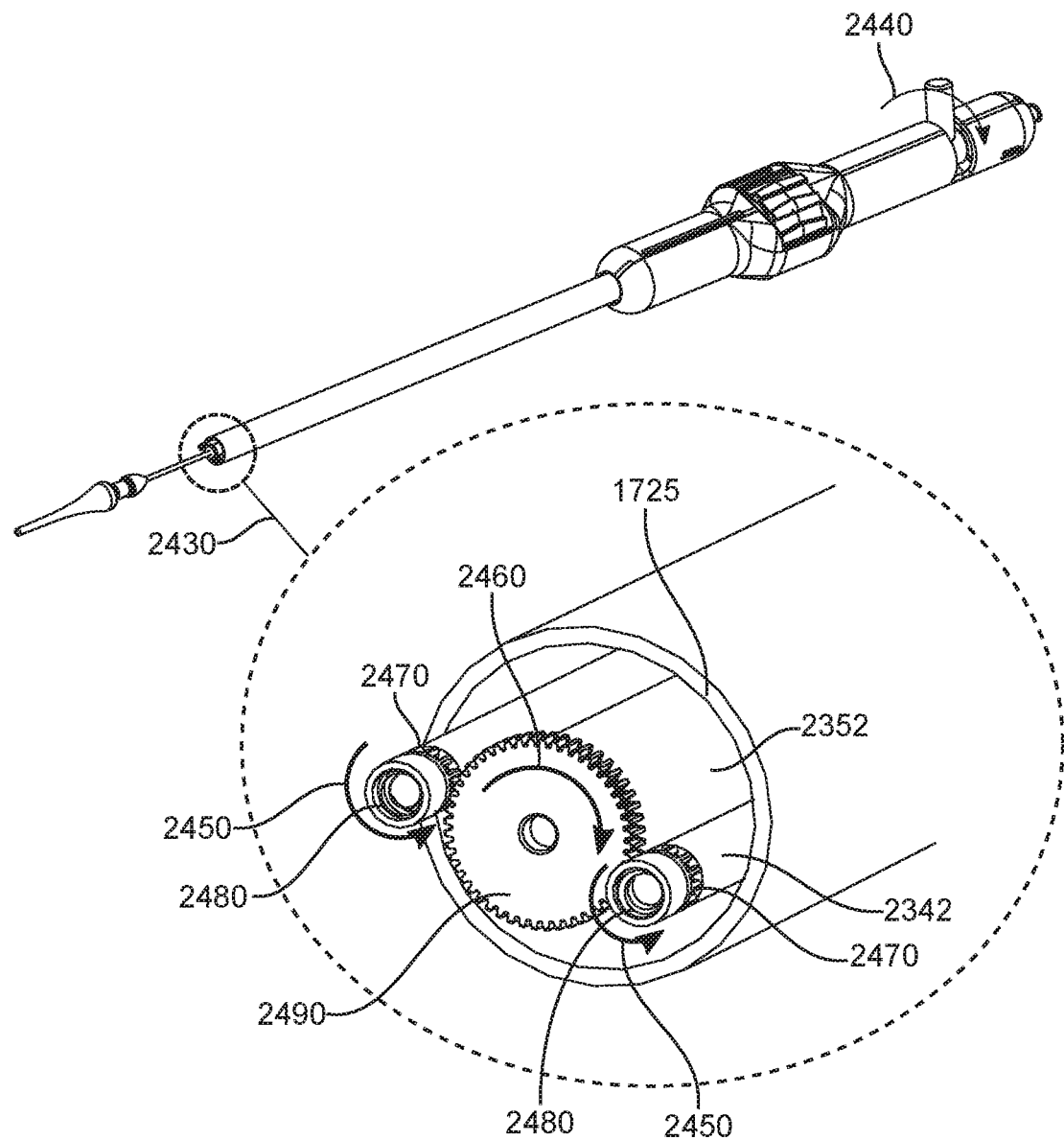
FIG. 31 shows an enlarged view of the sun-gear and plurality of screw connector anchor mechanisms at the end of an embodiment of a delivery system that may accommodate threaded wishbone shaped struts.

FIGS. 29-31 depict an embodiment of a delivery system corresponding to the description relating to FIGS. 15A-15B. FIG. 29 shows an exploded view of an embodiment of a delivery system that may be suitable for connecting with a prosthetic valve frame having a plurality of threaded type connector anchors (1400, as shown in FIG. 15A). The components set forth in this depiction may be substantially similar to the components set forth in FIG. 23. FIG. 29 shows an exploded view of the delivery handle portion of the delivery system 2320 and an exploded view of the concentrically nested catheters 2330. A slot 2390 may be formed at the proximal end of both delivery system handle A-side 2370, and B-side 2380. The slots may allow for rotational displacement of a level 2420 that may be orthogonal to and originates from a cylindrical torque transmitting member 2410. The torque transmitting member 2410 may be in mated connection with the proximal or driving end 2355 of a torque catheter 2350, and may travel concentrically through a catheter mount 2400, a leadscrew 2080, a plurality of stabilizers 2360, and a sheath catheter 1350 before terminating in a distal or driven end 2352 that may further transmit torque through a geared relationship and that is further described in FIG. 31. The catheter mount 2400 may provide a lateral location and fixation for fixed ends 2345 of a plurality of twisting thread-connector catheters 2340. The thread-connector catheters 2340 may be long, thin, flexible members which may be structurally rigid in compression. The thread-connector catheters may be able to be twisted about their axes when an appropriate torque is applied. In order to maintain the adjacency between the torque catheter 2350 and the plurality of thread-connector catheters 2340, a plurality of stabilizers 2360 may act as journal bearings to both internally retain the placement of the torque catheter 2350 and to externally retain the placement of the plurality of thread-connector catheters 2340. The plurality of thread-connector catheters may be concentrically nested within the sheath catheter 1350. As previously described, by rotating the thumbwheel 1955 the leadscrew 2080 and by extension sheath catheter 1350 may be made to translate, which in turn may cause the leading edge 1725 of the sheath catheter 1350 to advance towards or retreat from the dilator tip 1710.

FIG. 30 shows the exploded view 2330 of FIG. 29 in greater detail and shows the nesting configuration of the family of catheters.

FIG. 31 shows an enlarged view 2430, which illustrates in detail the mechanical interaction at the distal end of the delivery system of FIG. 29. As previously described, actuating the lever (2400, as shown in FIG. 29), which may be operably coupled to the driven end 2352 of the torque catheter (2350, as shown in FIG. 29) may cause the torque catheter to rotate, and may further cause a driving gear 2490 to rotate and transmit torque to a plurality of driven gears 2470 that are adjacent to the distal ends 2342 of the plurality of thread-connector catheters 2340 and by extension also adjacent to the threaded socket 2480 of each thread-connector catheter 2340. It should be apparent that rotation of the driving gear 2490 in a first direction (as shown by arrow 2460 indicating rotation) may cause a rotation of each of the driven gears 2470 in a second direction, opposite the first (as shown by arrows 2450 indicating rotation). A mechanical advantage may exist between the driving 2490 and driven 2470 gears. The mechanical advantage may result in an increase in rotational displacement of the driven gears with respect to the driving gears. The mechanical advantage may provide a 4:1 increase in rotational displacement of the driven gears with respect to the driving gears. At the distal end 2342 of each thread-connector catheter 2340 may be a threaded socket (2480, as shown in FIG. 31) which may be used to connectedly mate to a threaded fastener that may be anchored to an embodiment of the prosthetic valve (1390 and 1395, as shown in FIG. 15A).

Figure 32:
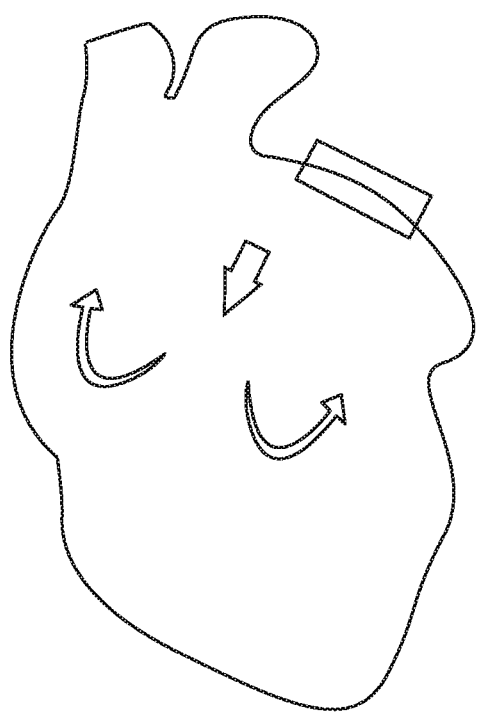
FIG. 32 shows turbulent blood flow in a heart.

FIG. 32 illustrates a prosthetic valve implanted in a mitral valve of a patient's heart. With traditional methods of implantation and traditional devices, the natural blood flow path may be disrupted and blood flow may become turbulent. The blood may flow toward the apex of the heart and towards the septal wall creating turbulence.

Figure 33:
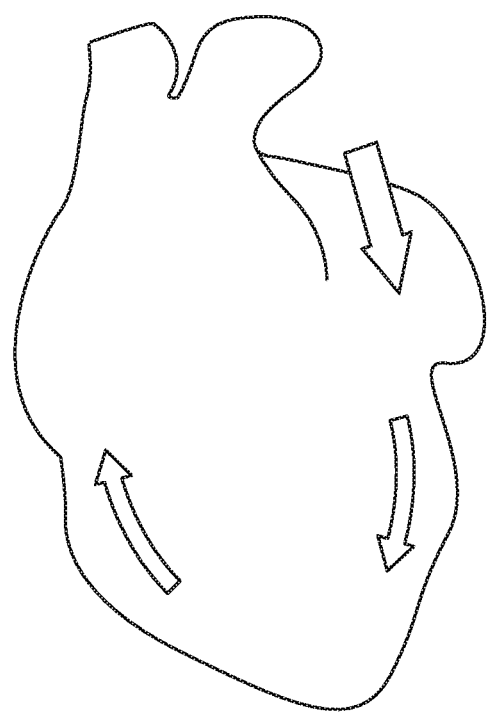
FIG. 33 shows non-turbulent blood flow in a heart.

FIG. 33 illustrates the desired blood flow path through the mitral valve and out the ventricle. The native mitral valve directs the blood to flow along the posterior wall of the ventricle towards the apex of the heart where the blood then continues to flow in a non-turbulent manner up the septal wall and then during heart systole the blood is ejected out of the left ventricular outflow tract (LVOT) and through the aorta to the rest of the body. In this configuration, the blood flow maintains its momentum and conserves its energy resulting in the most efficient flow.

Figure 34:
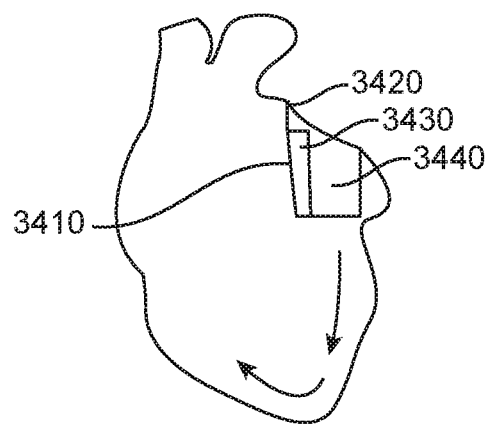
FIG. 34 illustrates a prosthetic mitral valve directing blood in the heart in a non-turbulent manner.

FIG. 34 illustrates a prosthetic valve implanted in a native mitral valve. The prosthetic mitral valve has features which preferably avoid obstructing the left ventricular outflow tract and also may help maintain the natural blood flow path so as to conserve momentum of the blood flow and avoid turbulence. For example, the prosthetic valve preferably has a large anterior prosthetic valve leaflet 3410 that spans the width of the native anterior valve leaflet. This will help mimic the size and motion of the native valve leaflet thereby avoiding obstruction of the LVOT. Additionally, the prosthesis has a low profile so that it does not extend too far in to the ventricle, and an atrial flange or skirt helps anchor the prosthesis to the atrial floor. The atrial skirt 3420 also preferably has a low profile. The prosthesis may also include one or preferably two anterior anchoring tabs 3430 that extend behind (anterior of the native leaflet) the native valve leaflets and anchor the prosthesis to the fibrous trigones on the anterior portion of the valve, or anchor on tissue adjacent and anterior of the anterior leaflet. The body 3440 of the valve may direct blood flow to the posterior. Additional details of the anchoring tabs may be found in U.S. Pat. No. 8,579,964, the entire contents of which have been previously been incorporated herein by reference. The body of the prosthesis may be designed to avoid LVOT obstruction and this may help direct blood flow downward along the posterior wall of the heart in a circular manner toward the apex, and then upward along the septum toward the LVOT, thereby maintaining a substantially normal blood flow path that avoids turbulence and maintains momentum of the blood flow. Additional details about these and other features of the prosthesis are discussed in greater detail in this specification.

Figure 35:
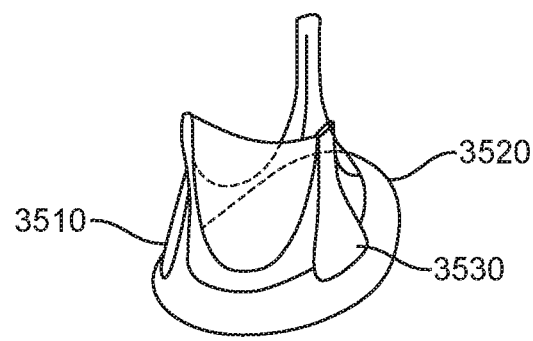
FIG. 35 illustrates a perspective view of a prosthetic valve.

FIG. 35 illustrates a ventricular view of the prosthesis which preferably has a large anterior prosthetic leaflet, and two posterior leaflets. Preferably, three commissure posts are used to support the prosthetic valve leaflets and form a tricuspid prosthetic valve. The prosthesis may comprise an atrial skirt 3520. Additionally, the prosthesis preferably includes two anterior anchor tabs 3510 and optionally one or more posterior anchor tabs 3530. The anterior anchor tabs may anchor to the fibrous trigones of the valve or they may anchor to tissue that is anterior of the anterior leaflet and adjacent thereto, and in order to avoid interfering with movement of the anterior prosthetic leaflet, the anterior anchor tabs are also preferably at the same circumferential position as the commissure posts. In this exemplary embodiment, the anterior anchor tabs are located approximately at the 10 o'clock and 2 o'clock positions along with two of the commissure posts. The prosthesis is preferably D-shaped in order to conform to the native valve anatomy. Therefore, the anterior portion of the valve is preferably flat and linear so that it does not impinge on the LVOT, and the posterior of the prosthesis is preferably cylindrical so that it conforms to the native valve. In some embodiments, instead of a flat and linear anterior portion, the anterior portion may be concave or slightly convex.

Figure 36A:
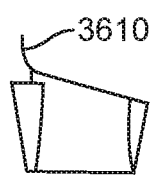
FIG. 36A illustrates the atrial skirt of a prosthetic valve.

FIG. 36A illustrates more clearly the two anterior anchor tabs which extend upward toward the atrium and away from the commissure posts which extend toward the ventricle, and similarly the posterior anchor also extends upward toward the atrium while the adjacent commissure post extends downward toward the ventricle. Note that in this view, only one of the anterior anchor tabs is visible. The prosthesis may comprise an atrial skirt 3610.

Figure 36B:
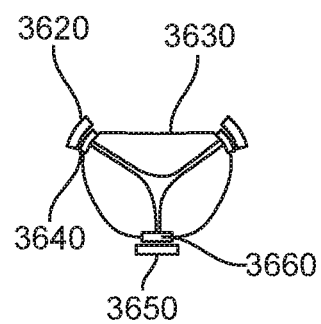
FIG. 36B illustrates a top view of a prosthetic valve.

FIG. 36B illustrates an outflow view of the prosthesis of FIG. 36A, whereby both anterior trigonal anchoring tabs are present, as well as the posterior anchoring tab, and the commissures associated with each of said tabs. It should be apparent that the commissure posts and anchoring tabs are adjacent each other. The prosthesis may comprise an anterior anchor 3620, an anterior leaflet 3630, an anterior commissure 3640, a posterior anchor 3650, and a posterior commissure 3660.

Figure 37:
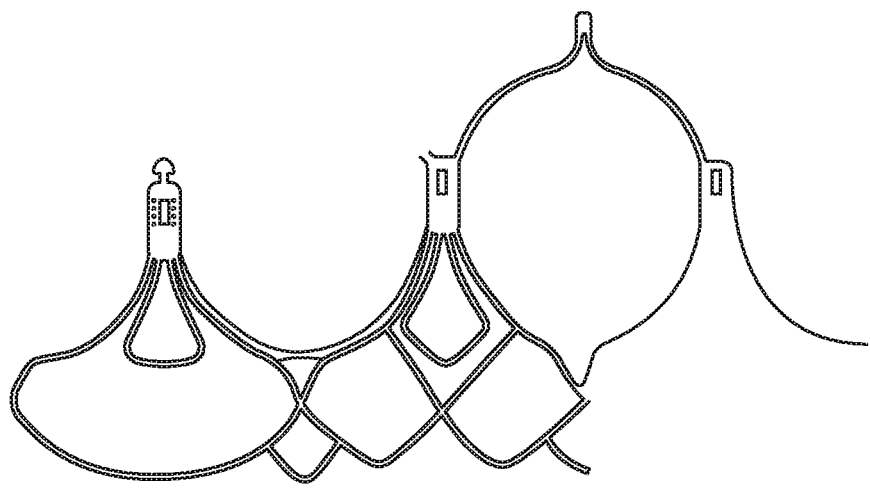
FIG. 37 illustrates a flat pattern of a prosthetic valve.

FIG. 37 illustrates two embodiments of structure on the prosthesis for coupling it to a delivery catheter. The figure shows a pattern of the anchor frame after it has been flattened and unrolled. It is formed from numerous interconnected struts which form open or closed cells that can self-expand or that may be balloon expandable. On the left side of FIG. 37, a first exemplary embodiment shows a single arcuate strut that forms a closed single cell on the atrial portion of the device. This strut may be folded radially outward to form a flanged region or atrial skirt which can anchor to the atrial floor. A commissure post with a D-shaped or mushroom head shaped, or anchor shaped portion on the opposite end of the prosthesis may be used to couple and uncouple the device from a delivery catheter as described previously in this specification and in U.S. Pat. No. 8,579,964 previously incorporated by reference, and is generally on a ventricular portion of the device. A triangular anchor tab is nested in the single cell between the commissure post and the atrial flange. Thus, the anchor tab is superior to the commissure post. The anchor tab may be formed to flare radially outward during deployment so that the anchor tab may be disposed behind a native leaflet (anterior to the anterior native leaflet, or posterior to a native posterior leaflet) and engage the anterior or posterior native anatomy as described in this specification. The commissure may have suture holes disposed therein in order to allow sutures to attach tissue or other material to the commissure posts. Nesting of the anchor tab adjacent the commissure post helps reduce overall device profile.

The right-hand side of FIG. 37 illustrates another exemplary embodiment of an anchor structure that allows the prosthesis to be coupled to the delivery catheter. On the right-hand side, multiple closed cells form the atrial region of the device which may be formed to flare radially outward and create a flanged region that may be secured to the atrial floor of the atrium. Two commissure posts include a slotted region for receiving sutures so that tissue or other material may be coupled to the device. The commissure posts are connected together with a wishbone shaped strut having a central tab that may be coupled to the delivery catheter. The wishbone may extend between two commissures or three commissures, or more commissures. Thus, in this embodiment, only a single connector is used to couple the prosthesis to the delivery catheter. The struts of the frame may be EDM machined or laser cut from tubing (e.g. hypo tube), laser cutting or photo etching a flat sheet and welding the ends together, or by other techniques known in the art.

FIG. 38 illustrates a perspective view of the prosthetic mitral valve. An upper portion includes an atrial skirt or atrial flange that generally takes the same form as the atrial skirt or flange described in U.S. Pat. No. 8,579,964, previously incorporated herein by reference. The prosthetic valve leaflets are also shown, and preferably include one large anterior leaflet that spans the width of the native anterior mitral valve leaflet, and may include two, or three, or more posterior prosthetic leaflets. Thus, the prosthetic valve may only have two prosthetic leaflets, or three or more prosthetic leaflets in total. Two anterior anchoring tabs also preferably share the same position as the commissure posts. This keeps the anterior commissure posts and the anterior anchor tabs out of the flow path thereby helping to avoid LVOT obstruction, and also helps keep overall profile of the device to a minimum in the collapsed configuration which is desirable during delivery.

FIG. 39A shows an anterior view of the prosthetic valve in the expanded configuration with the anchoring tabs flared outward and in the expanded configuration.

FIG. 39B shows a top view of the prosthetic valve with four prosthetic leaflets including one large anterior leaflet that spans the width of the native anterior leaflet and three posterior leaflets, all coupled together with four commissure posts that may optionally be combined with four anchor tabs. Two of these anchor tabs are preferably anterior anchoring tabs for anchoring the prosthetic valve to the fibrous trigones or any other anatomic location described herein including a region anterior of the anterior leaflet and adjacent thereto, and the two posterior tabs may anchor the prosthetic valve to the posterior shelf of the posterior annulus and posterior to the native posterior leaflet.

FIG. 40 shows deployment of the prosthesis by either a transseptal or by a transapical delivery system. In either, preferably an outer sheath catheter constrains the device from self-expanding and when the outer sheath catheter is retracted the device self-expands. Here, the sheath catheter is partially retracted and the anterior 4010 and posterior 4020 anchor tabs are partially deployed.

FIG. 41 shows a partial perspective view of the prosthetic valve with an upper saddle shaped atrial skirt for atrial anchoring along with the combined large anterior leaflet and two or three posterior leaflets and combined anchor tabs/commissure posts.

FIG. 42 shows a flat pattern of the combined anterior or posterior anchor tab that is nested in the commissure post. The anchors in alternative embodiments may be cut above the commissure posts and bent backward during heat treating and shape setting so they can anchor to the native heart valve anatomy as described in this specification. This may require the anchors to be deployed first, before other portions of the prosthesis, as seen in FIG. 40. This may also involve anchoring of the prosthesis to the delivery catheter on both the inflow end and the outflow ends of the prosthesis for successful delivery.

FIG. 43A shows the unexpanded anchor tabs which may be triangular in the collapsed configuration and have a horizontal paddle shape in the expanded configuration in order to increase the contact area and thereby minimize tissue trauma, tissue piercing during anchoring, as illustrated in FIG. 43B. Alternatively, the anchors may have pointed tips which pierce or embed in tissue to help anchor the device.

FIG. 43C shows an exemplary cut pattern of the prosthesis that provides the results seen in FIGS. 43A-43B.

FIG. 44 illustrates a top view of the prosthetic valve with a large anterior leaflet that spans the width of the native anterior leaflet, and two posterior prosthetic leaflets. The prosthetic leaflets are coupled together with three commissure posts.

FIG. 45 shows portions of the prosthesis including the upper atrial skirt, an annular region and the anchor tabs which may be combined with commissure posts. The anchor tabs are preferably 10 mm-50 mm long, more preferably 20 mm-30 mm long to allow adequate length to go under and behind the native valve leaflets to reach the fibrous trigones and/or posterior annulus or to anchor on other anatomic locations described herein including regions that are anterior of the native leaflet and adjacent thereto. Optionally, the prosthetic valve may not include a posterior anchoring tab. The annular section which is preferably D-shaped may be radially expanded into engagement with the native valve annulus and thus the radial force may be adequate to prevent the posterior portion of the prosthesis from tilting or otherwise pivoting upward into the atrium. Or teeth may be used to engage and/or penetrate the posterior annulus.

In any embodiment, the prosthesis may be recaptured and resheathed if needed in order to either abort the delivery procedure or to reposition the device.

Preferred embodiments are formed from nitinol or any other biocompatible material that is self-expanding. Preferred target sizes and profiles may be dependent on patient anatomy, but are estimated to be approximately 30 mm-50 mm×40 mm-50 mm D-shaped prosthesis that may be delivered in a delivery system that is less than 45 French in size. More preferably, the prosthesis is 35 mm-45 mm×40 mm-50 mm D-shaped and delivered with a delivery system less than 40 French in size. Smaller sizes are preferred, and nominally, the prosthesis is 40 mm×45 mm D-shaped and delivered with a delivery system less than 40 French.

In some embodiments, tethers may be used to help couple the prosthesis to the delivery system for controlling delivery.

FIG. 46 shows a top view of a prosthetic valve with four prosthetic leaflets and four commissure posts. Optionally, four anchoring tabs may also be co-located with the four commissure posts.

FIG. 47 shows a top view of prosthetic valve with three prosthetic leaflets and three commissure posts. Optionally, three anchoring tabs may also be co-located with the three commissure posts.

FIG. 48 shows the prosthesis unrolled and flattened out and having three commissure posts with three prosthetic leaflets and three anchoring tabs. The atrial skirt is also illustrated below the commissure posts and anchor tabs.

FIG. 49 shows the native anterior and posterior leaflet unrolled and flattened and superimposed over the three anchoring tabs.

FIG. 50 shows an embodiment where the anchor tabs (triangular shaped cells) are connected to the commissure posts configured for deployment as depicted in FIG. 40, where the anchor tabs are deployed first as an outer sheath when the delivery system is retracted. Alternative catheter attachment methods are depicted for this embodiment. Either the use of mushroom shaped anchor tabs at the atrial aspect of the device or a central wishbone style attachment can be used to secure the device to the catheter.

FIG. 51 shows a large anterior leaflet superimposed over two anterior anchor tabs and a posterior section of diamond shaped cells which may engage or pierce the posterior annulus in an exemplary embodiment that does not use a posterior anchor tab.

FIG. 52 illustrates another exemplary embodiment showing two anterior anchoring tabs formed and nested within the anterior commissure posts and a series of expandable diamond shaped cells which may anchor against the posterior annulus or may pierce into the posterior annulus thereby avoiding the need for a posterior anchoring tab. This embodiment includes four commissure posts.

Figure 53:
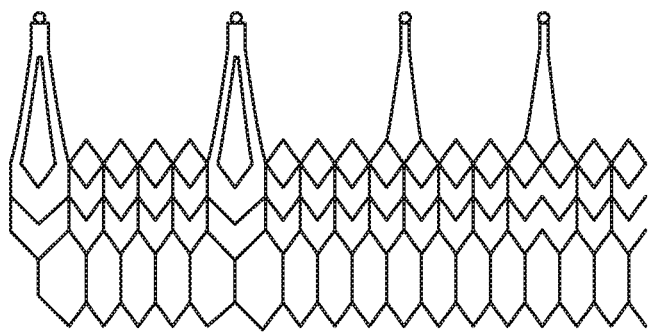
FIG. 53 shows another flat pattern of a prosthetic valve.

FIG. 53 illustrates another exemplary flat pattern of a prosthetic valve having two anterior anchor tabs nested in two anterior commissure posts and two posterior commissure posts. The atrial flange is shown below the commissure posts.

Figure 54:
FIG. 54 shows a perspective view of a prosthetic valve.

FIG. 54 shows a perspective view of a prosthetic valve with four commissure posts and a large anterior prosthetic leaflet coupled to two anterior commissure posts.

Figure 55:
FIG. 55 shows a mitral valve adjacent the aortic valve.

FIG. 55 shows a native mitral valve adjacent the aortic valve and preferably the anterior leaflet moves well away from the LVOT during systole. Preferably a prosthetic anterior leaflet would have similar motion to maintain natural flow dynamics such as maintaining blood flow momentum and reducing or eliminating turbulence.

Figure 56:
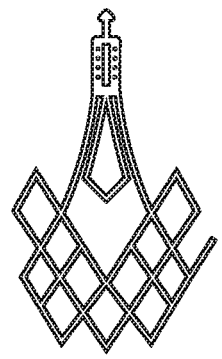
FIG. 56 shows still another anchor tab nested in a commissure post in the expanded configuration.

FIG. 56 shows another exemplary embodiment of a section of prosthetic valve having an anchoring tab nested within the commissure post and the adjacent closed cells of the frame are also shown.

Figure 57:
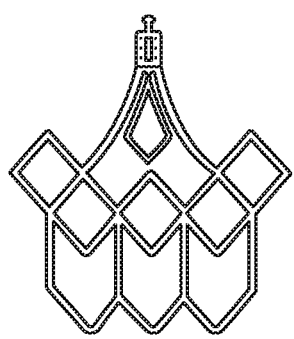
FIG. 57 shows an anchor tab nested in a commissure post in the expanded configuration.

FIG. 57 illustrates still another exemplary embodiment of a prosthetic valve having a commissure post and an anchoring tab nested with the commissure post.

Figure 58:
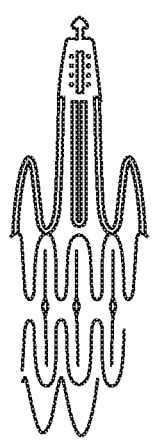
FIG. 58 shows an anchor tab nested in a commissure post in the collapsed configuration.

FIG. 58 shows yet another variation of a prosthetic valve having an anchoring tab nested within the commissure post.

Figure 59:
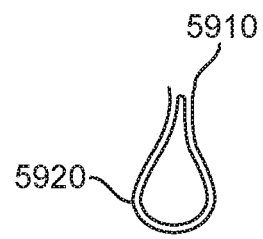
FIG. 59 shows variable strut thickness.

FIG. 59 shows how variable strut thickness (e.g. thicker 5910 and thinner 5920 regions) may be used to control the material properties of the prosthesis to create stiffer regions and less stiff regions.

While preferred embodiments of the present invention have been illustrated and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A prosthetic heart valve for implantation in a native heart valve of a patient, said prosthetic heart valve comprising:
   a radially expandable frame having an expanded configuration, a collapsed configuration, an upstream end, and a downstream end;
   a commissure post having a free end and an opposite end coupled to the frame;
   an anterior anchoring tab coupled to an anterior portion of the expandable frame adjacent the downstream end,
      wherein the anchoring tab extends radially outward from the expandable frame and the anchoring tab is configured to anchor the expandable frame to an anterior portion of the native heart valve, and
      wherein the anchoring tab is nested within the commissure post when the expandable frame is in the collapsed configuration; and
   a plurality of prosthetic valve leaflets each having a free end and a fixed end,
   wherein the fixed end is coupled to the expandable frame, and
   wherein the commissure post is coupled to at least one of the prosthetic valve leaflets.

2. The prosthetic valve of claim 1, wherein the free ends of the plurality of prosthetic valve leaflets have an open configuration and a closed configuration, wherein in the open configuration the free ends are disposed away from one another to allow antegrade flow therepast, and in the closed configuration the free ends are disposed adjacent one another to substantially prevent retrograde flow therepast.

3. The prosthetic valve of claim 1, wherein the plurality of prosthetic valve leaflets comprise an anterior prosthetic leaflet sized to span a width of a native anterior valve leaflet from a first fibrous trigone to a second fibrous trigone, and wherein in systole the anterior prosthetic leaflet is configured to deflect away from a left ventricular outflow tract (LVOT) of the native heart to provide a clear unobstructed outflow path.

4. The prosthetic valve of claim 1, further comprising a second anterior anchoring tab coupled to an anterior portion of the expandable frame adjacent the downstream end, and wherein second anchoring tab extends radially outward from the expandable frame in the expanded configuration, and the second anchoring tab is configured to anchor the frame to a second anterior portion of the native heart valve.

5. The prosthetic valve of claim 1, wherein the expandable frame comprises a D-shaped cross-section in the expanded configuration, wherein the anterior portion of the expandable frame is substantially flat to prevent impingement of the anterior portion against the left ventricular outflow tract (LVOT), and a posterior portion of the expandable frame is partially cylindrically shaped to conform with a posterior portion of the native valve.

6. The prosthetic valve of claim 1, wherein the native valve is a native mitral valve.

7. The prosthetic valve of claim 1, wherein the anterior anchoring tab comprises a fixed end and a free end, and wherein the fixed end originates from a downstream portion of the commissure post.

8. The prosthetic valve of claim 1, wherein the anterior anchoring tab originates from a circumferential position on a circumference of the expandable frame, and wherein the commissure post originates from the circumferential position.

9. The prosthetic valve of claim 1, wherein the commissure post comprises an anchoring element adjacent the free end thereof, the anchoring element configured to engage a delivery system.

\* \* \* \* \*

UNITED STATES PATENT AND TRADEMARK OFFICE
CERTIFICATE OF CORRECTION

PATENT NO. : 11,357,622 B2
APPLICATION NO. : 16/559169
DATED : June 14, 2022
INVENTOR(S) : Lane et al.

It is certified that error appears in the above-identified patent and that said Letters Patent is hereby corrected as shown below:

On the Title Page

In item (73), in "Assignee", in Column 1, Line 1, delete "Neovase" and insert --Neovasc-- therefor Signed and Sealed this
Thirty-first Day of January, 2023

Katherine Kelly Vidal
*Director of the United States Patent and Trademark Office*